(12) United States Patent
Staunton

(10) Patent No.: US 9,655,645 B2
(45) Date of Patent: May 23, 2017

(54) ASSEMBLY FOR PERCUTANEOUSLY INSERTING AN IMPLANTABLE MEDICAL DEVICE, STEERING THE DEVICE TO A TARGET LOCATION AND DEPLOYING THE DEVICE

(71) Applicant: Stryker Corporation, Kalamazoo, MI (US)

(72) Inventor: Douglas A. Staunton, Texas Township, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 436 days.

(21) Appl. No.: 14/089,015

(22) Filed: Nov. 25, 2013

(65) Prior Publication Data

US 2014/0121674 A1 May 1, 2014

Related U.S. Application Data

(63) Continuation of application No. PCT/US2012/039130, filed on May 23, 2012.
(Continued)

(51) Int. Cl.
*A61B 19/00* (2006.01)
*A61B 17/34* (2006.01)
*A61N 1/05* (2006.01)

(52) U.S. Cl.
CPC ........ *A61B 17/3468* (2013.01); *A61N 1/0558* (2013.01)

(58) Field of Classification Search
CPC ............ A61B 17/3468; A61B 17/3496; A61B 18/1492; A61B 2017/003;
(Continued)

(56) References Cited

U.S. PATENT DOCUMENTS

| 4,753,223 A | * | 6/1988 | Bremer | ................ | A61B 1/0058 |
| | | | | | 600/140 |
| 5,397,342 A | * | 3/1995 | Heil, Jr. | ............... | A61N 1/0587 |
| | | | | | 607/129 |

(Continued)

FOREIGN PATENT DOCUMENTS

WO   WO 2010114998 A1 * 10/2010 ......... A61B 17/3468

OTHER PUBLICATIONS

PCT App. No. PCT/US2012/039130 "International Search Report and Written Opinion", dated Aug. 2, 2012.

*Primary Examiner* — Elizabeth Houston
*Assistant Examiner* — Mohamed Gabr

(57) ABSTRACT

An assembly for implanting a medical device such as an electrode array. The assembly includes a sheath that is disposed over the medical device and a core that supports the device. The sheath and core are connected to, respectively, first and second slides in a handpiece. An single actuator first moves one slide, typically the slide to which the sheath is attached. Once the first slide at least partially displaced both slides are moved to simultaneously retract the sheath and core away from the implantable medical device. The assembly includes a steering assembly for steering the sheath and implantable medical device. Some of the components forming the steering assembly are disposed on at least one of the slides. Tensioners prevent the steering cables of the steering assembly from being exposed to excessive force.

26 Claims, 46 Drawing Sheets

Related U.S. Application Data

(60) Provisional application No. 61/490,876, filed on May 27, 2011.

(58) Field of Classification Search
CPC .. A61B 2017/347; A61N 1/0558; A61N 1/05; A61F 2002/9517; A61F 2/95; A61F 2/966; A61F 2/962; A61M 37/0069; A61M 25/0105; A61M 25/0113; A61M 25/0133; A61M 25/0136; A61M 25/0147; A61M 2025/015
USPC .................................................... 606/129
See application file for complete search history.

(56) References Cited

U.S. PATENT DOCUMENTS

| | | | | |
|---|---|---|---|---|
| 5,441,483 | A * | 8/1995 | Avitall | A61B 18/1492 604/95.05 |
| 5,588,964 | A * | 12/1996 | Imran | A61B 18/1492 604/528 |
| 5,611,777 | A * | 3/1997 | Bowden | A61M 25/0136 604/95.01 |
| 5,730,127 | A * | 3/1998 | Avitall | A61B 5/0422 600/374 |
| 5,810,807 | A * | 9/1998 | Ganz | A61B 18/1492 606/113 |
| 5,881,727 | A * | 3/1999 | Edwards | A61B 18/1492 600/374 |
| 5,944,690 | A * | 8/1999 | Falwell | A61M 25/0136 600/146 |
| 6,415,187 | B1 * | 7/2002 | Kuzma | A61N 1/05 607/116 |
| 6,514,261 | B1 * | 2/2003 | Randall | A61F 2/95 604/528 |
| 6,599,296 | B1 * | 7/2003 | Gillick | A61B 17/3207 606/108 |
| 6,926,669 | B1 * | 8/2005 | Stewart | A61B 18/1492 600/437 |
| 6,973,352 | B1 * | 12/2005 | Tsutsui | A61M 25/0045 607/122 |
| 6,997,939 | B2 * | 2/2006 | Linder | A61F 2/013 606/200 |
| 7,269,453 | B2 * | 9/2007 | Mogul | A61B 5/0422 600/374 |
| 7,278,998 | B2 * | 10/2007 | Gaschino | A61F 2/95 606/108 |
| 7,935,141 | B2 * | 5/2011 | Randall | A61F 2/95 606/108 |
| 7,993,384 | B2 * | 8/2011 | Wu | A61F 2/95 623/1.12 |
| 7,998,112 | B2 * | 8/2011 | Chow | A61M 25/0012 604/528 |
| 8,287,584 | B2 * | 10/2012 | Salahieh | A61F 2/2418 606/108 |
| 8,641,664 | B2 * | 2/2014 | Kirschenman | A61M 25/0067 604/95.04 |
| 8,641,752 | B1 * | 2/2014 | Holm | A61F 2/966 623/1.12 |
| 8,956,352 | B2 * | 2/2015 | Mauch | A61B 18/1492 606/27 |
| 9,144,493 | B2 * | 9/2015 | Carr | A61F 2/2436 |
| 9,271,701 | B2 * | 3/2016 | Malkowski | A61B 17/00 |
| 2002/0022873 | A1 * | 2/2002 | Erickson | A61B 5/0422 607/117 |
| 2003/0028236 | A1 * | 2/2003 | Gillick | A61F 2/95 623/1.11 |
| 2003/0069577 | A1 * | 4/2003 | Vaska | A61B 18/02 606/41 |
| 2003/0191516 | A1 * | 10/2003 | Weldon | A61F 2/95 623/1.12 |
| 2004/0006380 | A1 * | 1/2004 | Buck | A61F 2/966 623/1.11 |
| 2004/0181239 | A1 * | 9/2004 | Dorn | A61F 2/95 606/108 |
| 2004/0186543 | A1 | 9/2004 | King et al. | |
| 2006/0167416 | A1 * | 7/2006 | Mathis | A61B 10/0275 604/164.01 |
| 2006/0241717 | A1 | 10/2006 | Whitehurst et al. | |
| 2007/0055340 | A1 * | 3/2007 | Pryor | A61F 2/95 623/1.11 |
| 2007/0168014 | A1 * | 7/2007 | Jimenez | A61F 2/95 623/1.12 |
| 2007/0203503 | A1 * | 8/2007 | Salahieh | A61B 17/0644 606/108 |
| 2008/0065182 | A1 | 3/2008 | Strother et al. | |
| 2008/0294230 | A1 * | 11/2008 | Parker | A61F 2/95 623/1.11 |
| 2009/0125093 | A1 * | 5/2009 | Hansen | A61F 2/95 623/1.11 |
| 2009/0293270 | A1 * | 12/2009 | Brindley | A61N 1/05 29/829 |
| 2010/0036472 | A1 * | 2/2010 | Papp | A61F 2/95 623/1.11 |
| 2010/0076541 | A1 * | 3/2010 | Kumoyama | A61F 2/95 623/1.11 |
| 2010/0168834 | A1 * | 7/2010 | Ryan | A61F 2/95 623/1.11 |
| 2010/0331883 | A1 | 12/2010 | Schmitz et al. | |
| 2011/0034987 | A1 * | 2/2011 | Kennedy | A61F 2/95 623/1.11 |
| 2011/0077660 | A1 | 3/2011 | Janik et al. | |
| 2011/0276062 | A1 * | 11/2011 | Bolduc | A61B 17/00234 606/139 |
| 2012/0022551 | A1 * | 1/2012 | Staunton | A61B 17/3468 606/129 |
| 2012/0022632 | A1 * | 1/2012 | Hoffman | A61F 2/966 623/1.11 |
| 2012/0059448 | A1 * | 3/2012 | Parker | A61F 2/95 623/1.11 |
| 2012/0253386 | A1 * | 10/2012 | Rowe | A61B 17/0293 606/213 |
| 2012/0310316 | A1 | 12/2012 | Janik et al. | |
| 2012/0330393 | A1 | 12/2012 | Janik et al. | |
| 2013/0012966 | A1 * | 1/2013 | Park | A61F 2/0063 606/151 |
| 2013/0211493 | A1 * | 8/2013 | Wubbeling | A61F 2/95 623/1.11 |
| 2014/0121674 | A1 * | 5/2014 | Staunton | A61B 17/3468 606/129 |
| 2014/0277366 | A1 * | 9/2014 | Cummins | A61F 2/966 623/1.12 |
| 2014/0324151 | A1 * | 10/2014 | Yamashita | A61F 2/82 623/1.11 |
| 2014/0343660 | A1 * | 11/2014 | Shimoyama | A61F 2/966 623/1.11 |
| 2015/0057739 | A1 * | 2/2015 | Costello | A61F 2/966 623/1.11 |
| 2015/0148889 | A1 * | 5/2015 | Angel | A61B 17/12113 623/1.23 |
| 2016/0008575 | A1 * | 1/2016 | Kimmel | A61M 25/0127 600/417 |
| 2016/0074190 | A1 * | 3/2016 | Cummins | A61F 2/966 623/1.11 |
| 2016/0135975 | A1 * | 5/2016 | Shimoyama | A61F 2/844 623/1.12 |

* cited by examiner

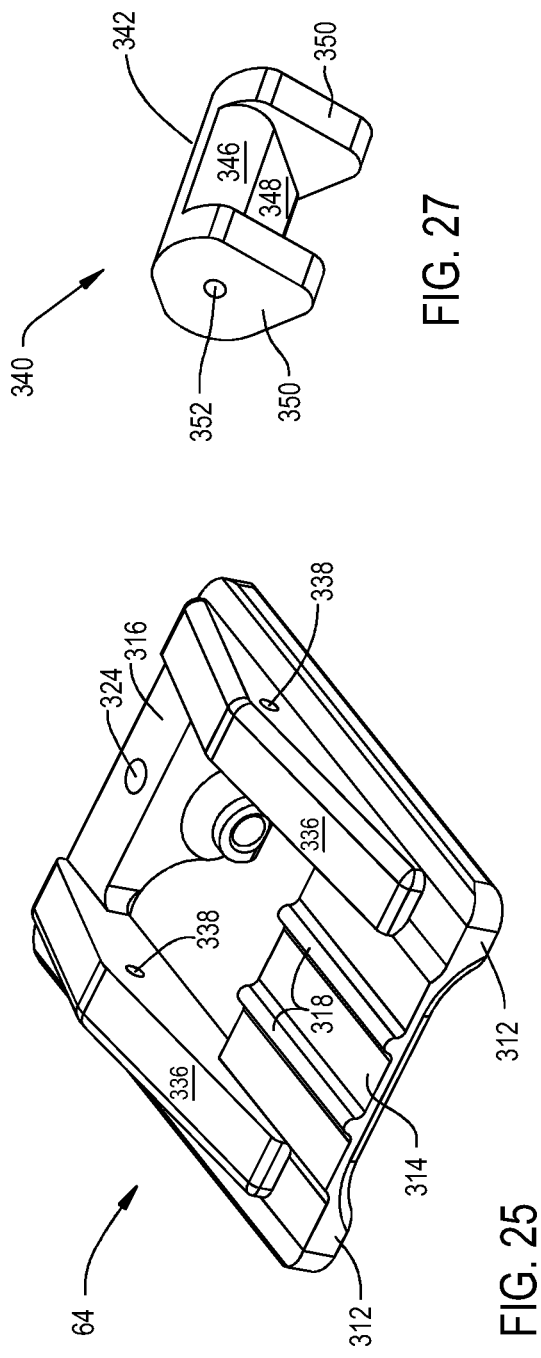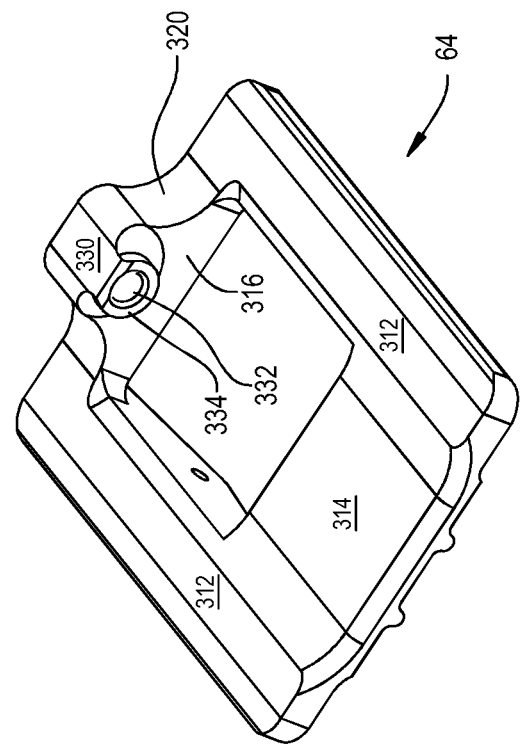

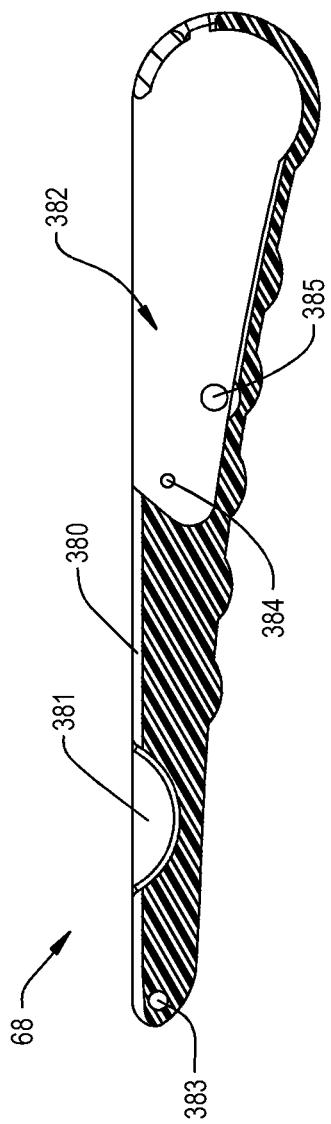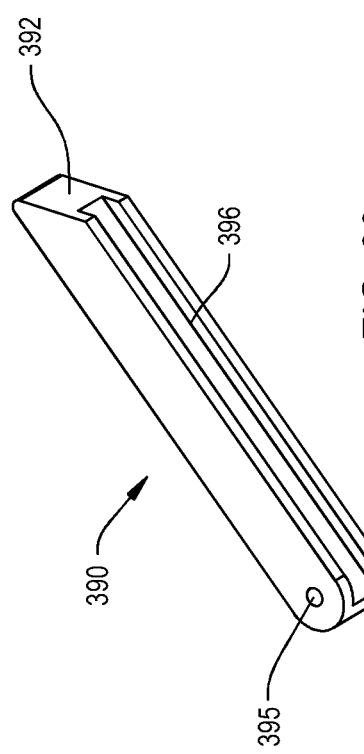

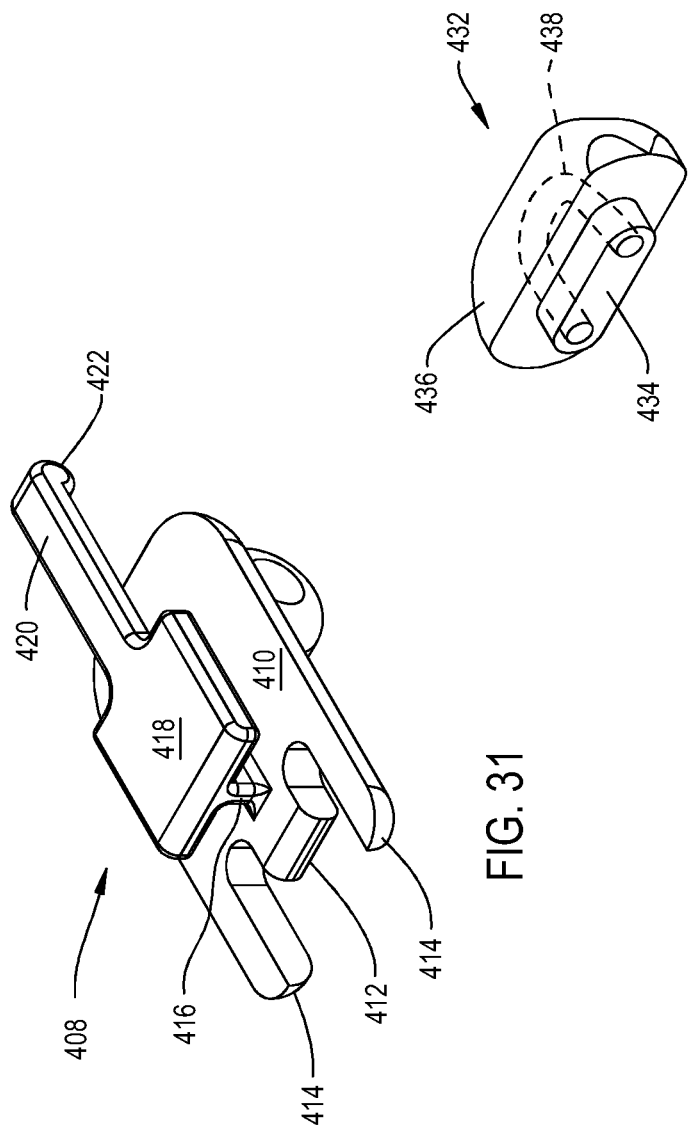

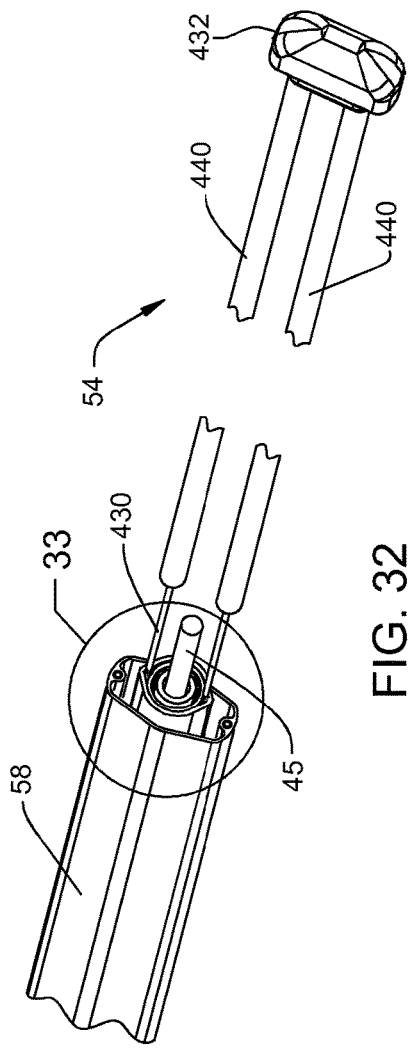
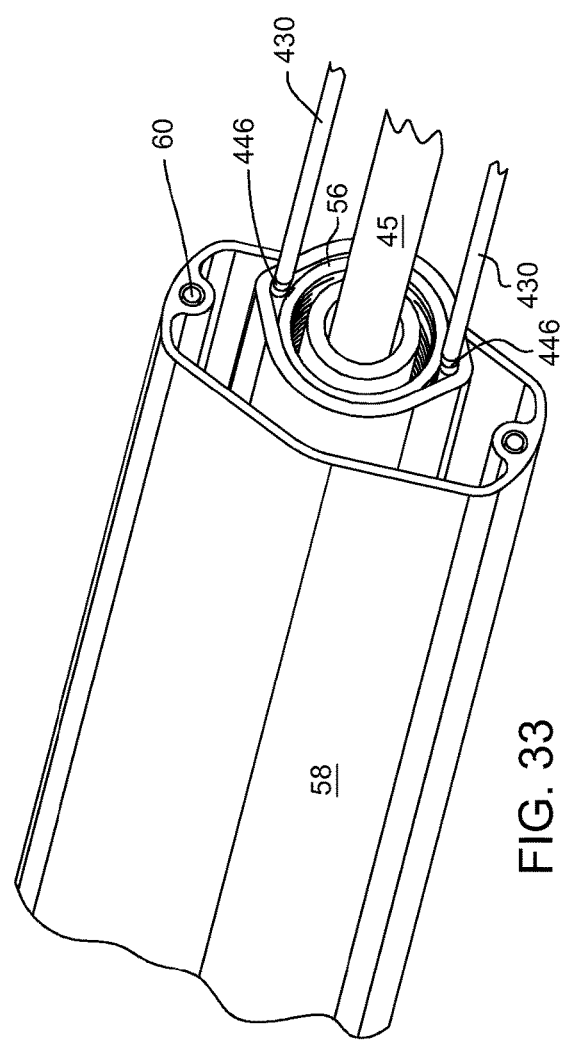
FIG. 32
FIG. 33

ASSEMBLY FOR PERCUTANEOUSLY INSERTING AN IMPLANTABLE MEDICAL DEVICE, STEERING THE DEVICE TO A TARGET LOCATION AND DEPLOYING THE DEVICE

RELATIONSHIP TO PRIORITY APPLICATIONS

This application is a continuation of PCT Pat. App. No. PCT/US2012/039130 filed 23 May 2012. PCT Pat. App. No. PCT/US2012/039130 is a non-provisional of U.S. Prov. Pat. App. No. 61/490,876 filed 27 May 2011. The priority applications are specifically incorporated herein by reference.

FIELD OF THE INVENTION

This invention relates generally to a system and method for percutaneously inserting and deploying an implantable medical device array. More particularly, the system of this invention is able to insert the device in a minimally invasive procedure, steer the device to a target location and then, if appropriate unfold the device.

BACKGROUND OF THE INVENTION

There are a number of medical conditions for which it has been found that an effective therapy involves driving current through a section of the tissue of a patient. Often, the current is driven between the electrodes of an electrode array implanted in the patient. Generally, the electrode array includes a non-conductive carrier on which typically two or more electrodes are disposed. Once the electrode array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles. There is an increasing interest in implanting electrode arrays adjacent neural tissue so that the resultant current flow induces a desired neurological or physical effect. In one known application, the current driven between the electrodes of an array placed on top of the dura in the vertebral column reduces the extent to which chronic pain signals are perceived by the brain. Alternatively, the array may be placed in a location where the current flow stimulates a feeling of stomach fullness as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

The Applicants' Patent Application No. PCT/US2009/33769, FOLDABLE, IMPLANTABLE ELECTRODE ARRAY ASSEMBLY AND TOOL FOR IMPLANTING SAME, filed 11 Feb. 2009, published as WO 2009/111142 and as U.S. Pat. Pub. No. US 2011/0077660 A1, the contents of which are explicitly incorporated herein by reference, describes an electrode array that includes a frame on which plural electrodes are arranged in a row by column matrix. An advantage of this electrode array is that it allows current to be flowed between numerous different combinations of electrodes. Depending on which electrodes are operated to function as current sources and sinks, this array can be operated so that there are two or more current flows occurring simultaneously between different sets of electrodes. Once this array is deployed, the practitioner drives current between different combinations of electrodes. Current therefore flows through different sections of tissue. This allows the practitioner to determine between which electrodes, through which tissue, the current flow offers the greatest benefit and/or tolerable side effects. Once the optimal current flow path between the electrodes is determined, the array and its associated power supply are set to operate in this state. Should the electrodes shift or the clinical needs change, the array can be reset to accommodate these changes.

In comparison to other electrode arrays with lesser numbers of electrodes, the above-described array makes it possible to flow current through more discretely targeted sections of tissue and to selectively focus/diffuse the current flow. In contrast to an electrode array with a smaller number of electrodes, use of the above-described array increases the likelihood that the current flow can be set to provide desired therapeutic effects, with tolerable side effects.

Previously, there was a disadvantage of providing an electrode array with numerous individual electrodes that collectively occupy a large surface area. Specifically, owing to the size of these arrays, it was believed that the only way to position them against the tissue through which current is to be driven was to cut a relatively large incision in the patient to provide access to the target tissue. Typically, this incision is more than 3 cm in length and, often at least 5 cm in length. Once the incision is made, it is then usually necessary to retract at least a portion of the tissue overlying the target tissue. In some insertion procedures, removal of some of the overlying tissue is required. The electrode array was passed through the incision and placed against the target tissue. Once the electrode array was positioned, the incision was closed.

The electrode array of the incorporated by reference WO 2009/111142, is designed in part to be implanted in a patient without requiring such a large sized incision, tissue removal and the attendant trauma that results from these procedures. The Applicants' array of this incorporated-by-reference document is designed so that the electrodes are disposed on a frame formed from a superelastic material. A superelastic material is one that, after being subjected to appreciable bending or folding, returns to its initial state. Once this electrode array is formed, the assembly is then folded or rolled into a form that has a side-to-side width appreciably less than its width in the unfolded/unrolled state.

The Applicant's PCT Pat. App. No. PCT No. PCT/US2010/029628, published as US 2012/0022551 A1, DELIVERY ASSEMBLY FOR PERCUTANEOUSLY DELIVERING AND DEPLOYING AN ELECTRODE ARRAY AT A TARGET LOCATION, THE ASSEMBLY CAPABLE OF STEERING THE ELECTRODE ARRAY TO THE TARGET LOCATION, filed 1 Apr. 2010, the contents of which are incorporated herein by reference, discloses how a foldable electrode array can be folded around a core. The core and folded over array are encased in a sheath. Steering cables are encased in the sheath. The assembly of this invention is designed to be advanced through a portal formed in the patient. From the portal, the assembly is advanced through a potential space in the patient to the target location where the array is to be deployed. Tensions are selectively imposed on the steering cables to steer the sheath. This steering is necessary to direct the sheath, and the components encased therein, around obstructions so the sheath and encased components can be pushed to the target location. The sheath is considered at the target location when the distal end of the sheath, the section holding the folded electrode array, is disposed over the tissue against which the array is to be deployed. Once the sheath is at the target location, the sheath is retracted away from the electrode array and the core. The retraction of the sheath allows the release of the potential energy of the material forming the array frame. The release of this energy unfolds the array from around the core so the array is disposed against the target tissue. At this stage of the deployment process, the core remains between the array and the tissue against which the array is to be deployed. The core is retracted away of the unfolded electrode array. The array therefore seats against underlying tissue. Once the array is so seated, the array is considered completely deployed and ready for use.

Applicant's PCT Pat. App. No. PCT No. PCT/US2010/029628 discloses how a folded over array can be steered to a location over the tissue against which the array is to be deployed. However, this document does not teach: how the folded over array is initially percutaneously inserted in the patient; how the array is initially positioned in the proper orientation for advancement to the target location; or the structure of tool that can be used to both advance the sheath-encased array to the target location while steering the array. Also, the prior application does not disclose tools that can be used to first retract the sheath away from the array and then retract the core from out from underneath the folded over array.

SUMMARY OF THE INVENTION

This invention relates generally to system that: advances and positions an implantable medical device over target tissue; deploys the positioned device; and retracts away from the device the components used to facilitate the positioning of the array. The system of this invention allows the device to be positioned and deployed percutaneously, that is through a relatively small portal, as opposed to a large incision, formed in the skin of the patient.

Medical devices that can be implanted using this invention include electrode arrays and stents.

The invention includes a core for supporting the device to be implanted and/or a sheath that surrounds the device. There is a handpiece dimensioned to be held in one hand. Integral with the handpiece is a steering unit. The steering unit controls one or more steering cables that extend to the device, the core or sheath. The steering unit is controlled by a manually actuated member attached to the handpiece. This manually actuated member is positioned to be controlled by thumb or fingers of the hand holding the handpiece.

Internal to the handpiece is a retraction assembly. The retraction assembly is connected to the core supporting the device or the sheath in which the device is disposed. The retraction assembly retracts the attached core or sheath away from the device. The retraction assembly is actuated by a control member. This control member is mounted to the handpiece to be actuated by the thumb or fingers of the hand holding the handpiece.

If the implanted medical device is both supported by a core and encased in a sheath, there are two retraction assemblies. A first retraction assembly retracts the sheath. This first retraction assembly includes a distal slide located internal to the handpiece which is the component of the assembly to which the sheath is attached. A second retraction assembly retracts the core. The second retraction assembly includes a proximal slide internal to the handpiece which is the component of the handpiece to which the core is attached. In some embodiments of the invention, a single control member is depressed to actuate both retraction assemblies. In some embodiments of the invention, the retraction assemblies are arranged so that the first retraction assembly at least partially retracts the sheath away from the implanted device prior to the second retraction assembly withdrawing the core away from the device.

The system of this invention also includes a guidewire and a dilating introducer sleeve.

The process of inserting and deploying an implantable device such as an electrode array of this invention begins with the insertion of the guidewire into the patient. The guidewire is steerable. The guidewire is advanced and steered toward the target tissue. Current may be sourced from or sunk to electrodes on the guidewire. These current flows provide information regarding the location of the guidewire to the target tissue. The dilating introducer sleeve is threaded over the guidewire. The introduction of the sleeve expands the surrounding tissue so as to form a portal into the potential space into which the sheath is to be inserted. The sheath is then introduced into the patient through the portal.

Once the sheath is inserted, the sheath-encased electrode array is advanced towards the target location. This process is performed by advancing the handpiece forward. Simultaneously with the handpiece advancement, the steering assembly is selectively actuated. The actuation of the steering assembly results in the off axis movement of the core and the components disposed over the core, the electrode array and the sheath. This off-axis movement of the core is what is employed to steer the electrode array to the target location. The steering assembly is actuated by depressing a control member with a finger or the thumb of the hand holding the handpiece.

Once the electrode array is at the target location, the handpiece ratchet is actuated. The ratchet is actuated using the fingers or thumb of the hand hold the handpiece. Initially, the ratchet retracts the distal slide. This movement of the distal slide results in a like retraction of the sheath away from the electrode array. As the sheath retracts away from the array, the potential energy stored in the material forming the array is released. The release of this potential energy unfolds the array. At this point in the deployment process, the core remains disposed between the electrode array and the underlying target tissue.

The practitioner continues to actuate the ratchet. This continued actuation of the retractor subsequently results in the simultaneous retraction of both the distal slide and the proximal slide. The retraction of the proximal slide retracts the core out from underneath the electrode array. Once the core is fully retracted, the electrodes of the electrode array are disposed against the target tissue, the tissue through which current is to be flowed.

As a consequence of the complete retraction of the proximal slide, the practitioner knows that the core is retracted away from the electrode array. The practitioner then withdraws the handpiece, sheath and core out of the patient to complete this portion of the insertion process.

The insertion assembly of this invention provides a means to identify the target tissue prior to the insertion of the electrode array. The assembly includes components useful for establishing a pilot path for the electrode array to the target tissue. The handpiece of the assembly is multifunctional. The handpiece allows a practitioner to perform the steering needed to: position the electrode array at the target tissue; retract the sheath so that electrode array can unfold; and retract the core so to cause the electrode array to seat over the target tissue.

BRIEF DESCRIPTION OF THE DRAWINGS

The invention is pointed out with particularity in the claims. The above and further features and benefits of this invention are understood by the following detailed description taken in conjunction with the following drawings in which:

FIG. 25 is perspective view of the proximal slide;

FIG. 26 is a perspective view of the underside of the proximal slide;

FIG. 27 is a perspective view of the cam lock;

FIG. 29 is a cross sectional view of the ratchet;

FIG. 30 is a perspective view of the pawl;

FIG. 31 is a perspective view of the ratchet release tab;

FIG. 32 is a partial perspective view of the core around which the electrode is folded;

FIG. 33 is an enlargement of the view of FIG. 32 showing how the array cable and system core extend forward from the sheath encased spring;

FIG. 34 is a perspective view of the core tip;

DETAILED DESCRIPTION

I. Overview

Figure 1:
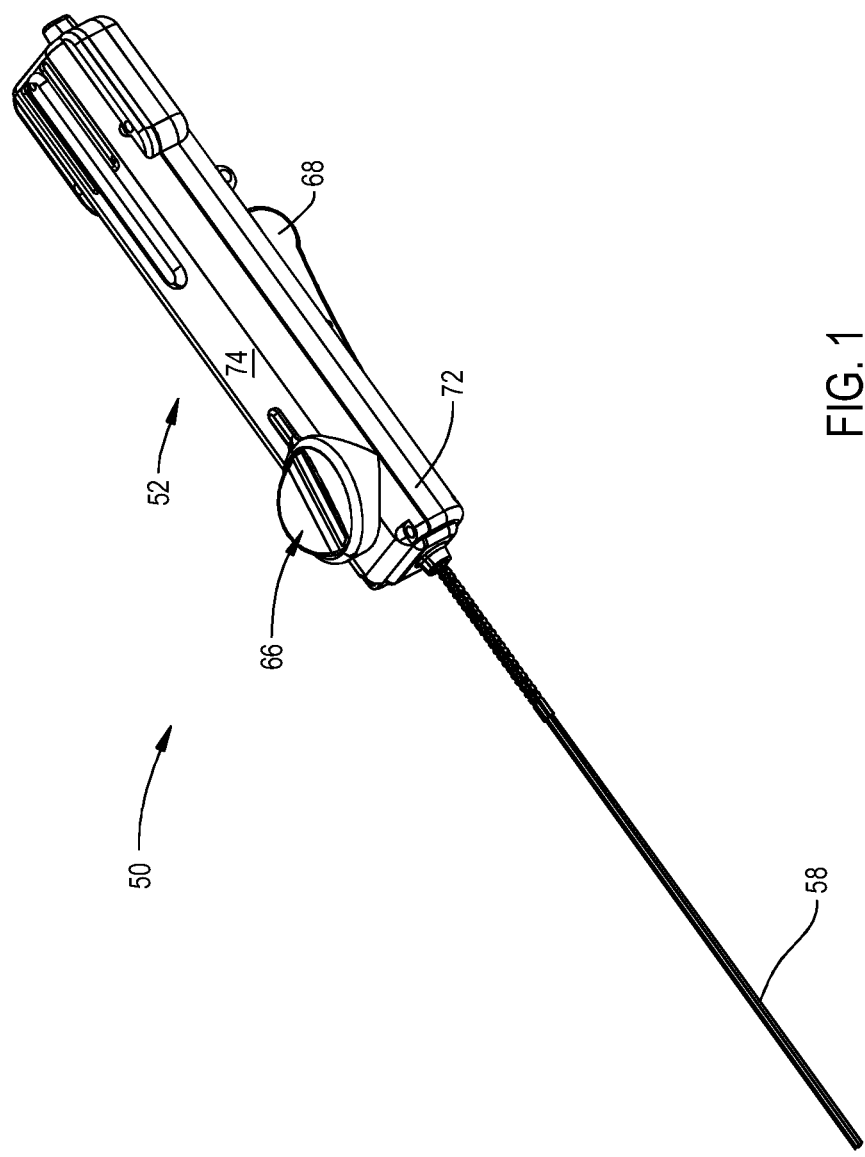
FIG. 1 is a perspective view of an insertion handle and the proximal end of a sheath of this invention.
Figure 2:
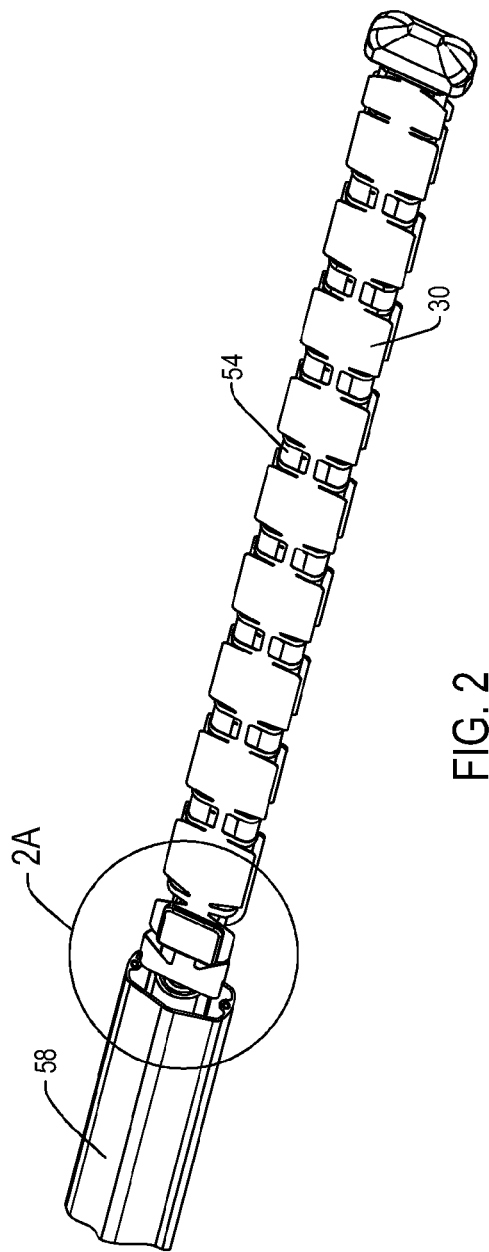
FIG. 2 is a perspective view of an electrode array disposed around a core of the insertion handpiece.

FIGS. 1 and 2 illustrate components of system 50 of this invention used to percutaneously, insert, steer and deploy an implantable medical device. This type of device provides a therapeutic benefit and/or diagnostic information. The representative implantable medical device is an electrode array 30. System 50 includes a handpiece 52. Located distally forward of the handpiece 50 is a core 54. (Here "distal" means away from the practitioner holding the handpiece/ towards the target location. "Proximal" means towards the practitioner/away from the target location.) The electrode array 30 is folded, or rolled, over the distal portion of the core 54. Proximal to where the electrode array 30 is folded\bent\wrapped over the core 54, wires forming the core are secured over the outer surface of a spring 56 (identified in FIG. 33). The wires forming core 54 and spring 56 extend proximally, into handpiece 52. Also extending forward from the handpiece 52 is a sheath 58. The sheath 58 extends over the core 54. The sheath 58 also extends over the folded over electrode array 30, core 54 and spring 56. (Only a portion of sheath 58 is shown in FIG. 2 so that the system components disposed in the sheath can be seen.) Two opposed steering cables 60 (FIG. 2A) are disposed in the sheath 58.

Figure 3:
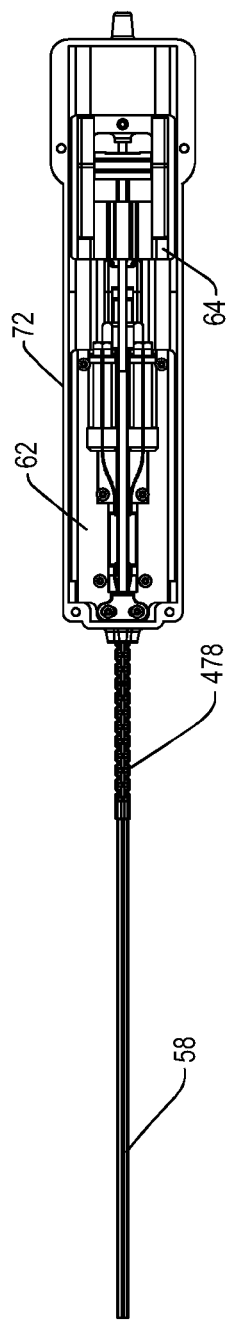
FIG. 3 is a plan view of the handpiece of this invention, looking into the base of the handpiece with the cover removed.

As seen in FIG. 3, disposed inside the handpiece 52 are a distal slide 62 and a proximal slide 64. Distal slide 62 is located forward of and initially spaced away from proximal slide 64. Both slides 62 and 64 are capable of moving longitudinally through handpiece 52. Sheath 58 is attached to the distal slide 62. Also attached to the distal slide 62 are the steering cables 60. The steering cables 60 are connected to a steering unit 66 mounted to the distal slide 62. The core 54 forming wires and spring 56 are attached to the proximal slide 64.

Also mounted to handpiece 52 is a pivoting ratchet 68. Ratchet 68 engages the distal slide 62. Actuation of ratchet 68 results in the proximally, rearwardly directed movement of both the distal slide 62 and the attached sheath 58. Once the distal slide 62 moves rearward a set distance, the continued movement of the distal slide 62 results in a like displacement of the proximal slide 64. Spring 56 moves with the distal slide 64. Since the core-forming wire is attached to spring 56, this rearward movement of the proximal slide 64 results in a like movement of core 54.

Figure 44:
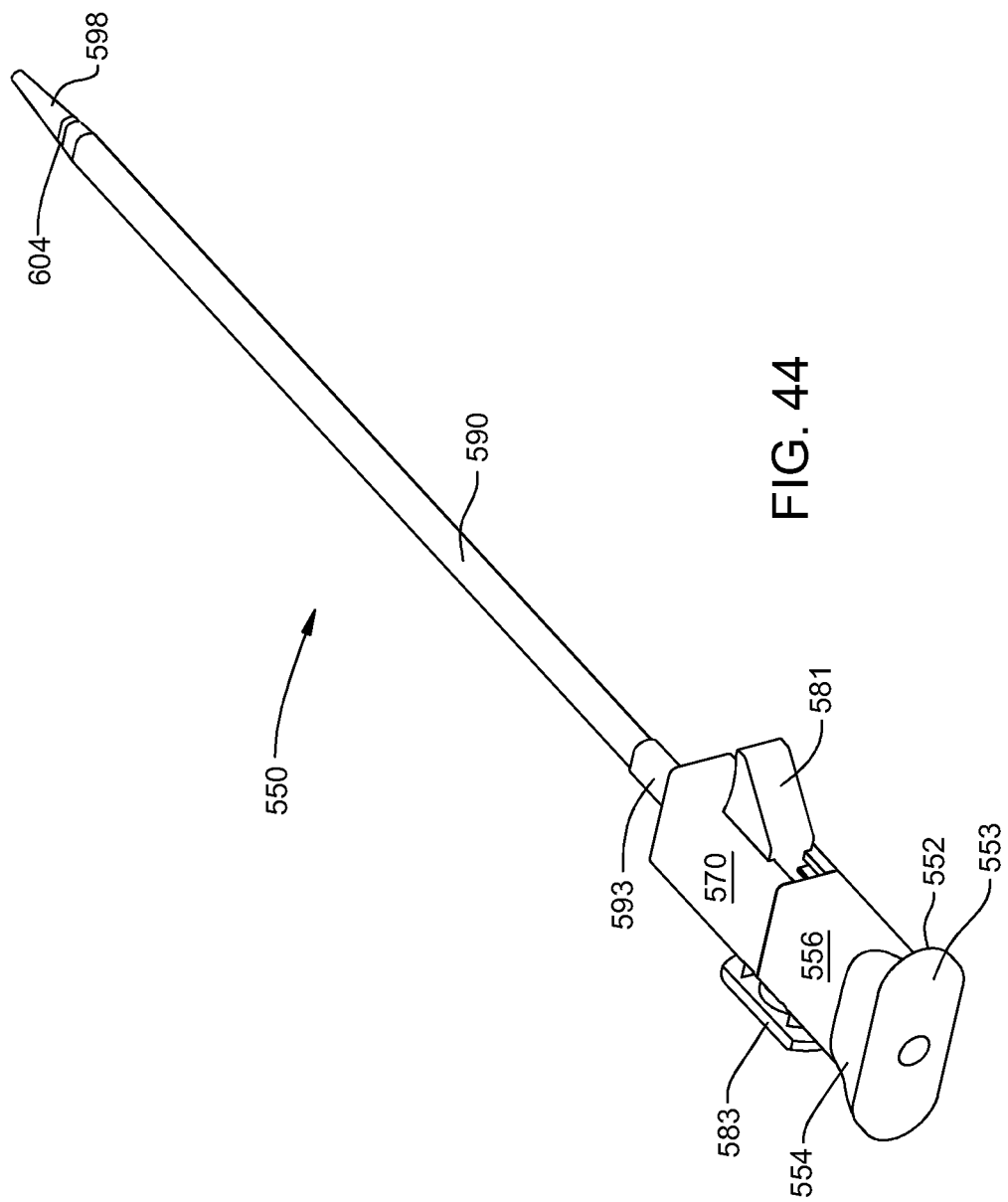
FIG. 44 is a perspective view of the introducer of this invention.

System 50 of this invention also includes a stimulating guidewire 510 (FIG. 40) and an introducer 550. (FIG. 44). At the start of the procedure for implanting the electrode array 30, guidewire 510 is used to verify the location of the target tissue, alternatively, the "target location," over which the array is to be deployed. Introducer 550 is then used to define the portal through which the sheath with encased array 30 is percutaneously inserted into the patient.

II. Electrode Array Assembly

Figure 4:
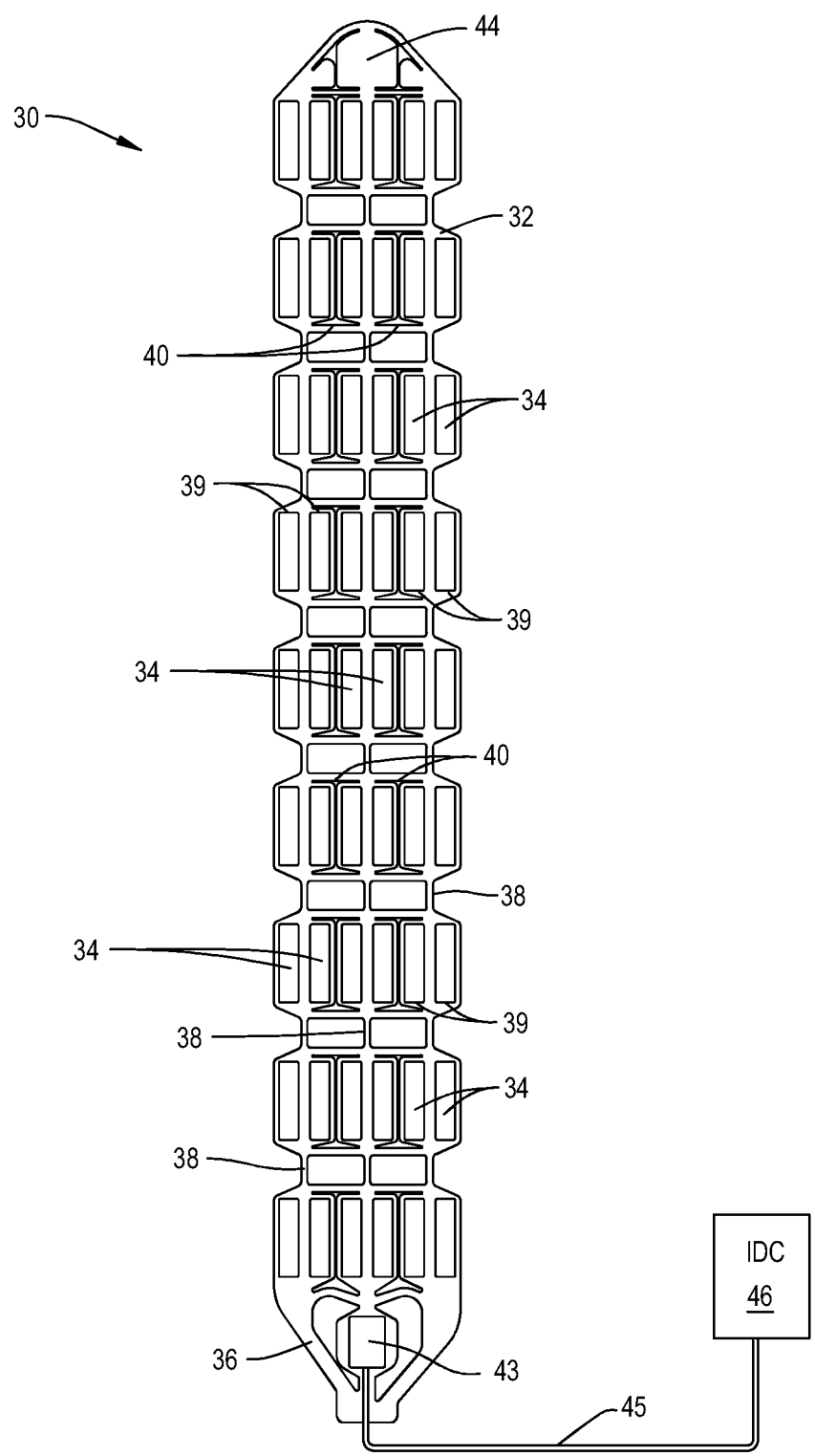
FIG. 4 is a plan view of one electrode array system of this invention with which this invention can be used.

FIG. 4 illustrates features of an electrode array 30 with which the system 50 of this invention is used. Array 30 includes a frame 32. The frame 32 is formed from material that at a minimum is flexible, is able to engage in some bending without undergoing plastic deformation. Frame 32 is typically formed from material that is elastic, which is material that, upon removal of a deforming force, returns to its initial shape. More preferably, the frame 32 is formed from material that is superelastic, material that when, subjected to an appreciable deforming force or stress and then this force/stress is removed, returns to its initial shape. One such superelastic material is a nickel titanium alloy known as Nitinol. Electrodes 34 are disposed on the frame 32. The electrodes 34 are the conductive components that abut the tissue against which the array 30 is disposed.

The illustrated frame 32 has a tail 36 and head 44 spaced longitudinally away from the tail. Three parallel, laterally spaced apart bridges 38 extend between tail 36 and the head 44. Each bridge 38 is formed to have plural pairs of tabs 39. The tabs 39 comprising a pair of tabs extend outwardly from the opposed sides of the bridge 38 with which the tabs are integral. Frame 32 is shaped so that each pair of tabs 39 that extends outwardly from one bridge 38 is laterally aligned with a pair of tabs 39 that extend outwardly from the other bridges 38. The tabs 39 that extend outwardly from adjacent bridges towards each other are spaced apart from each other. In the illustrated version of the invention, since there are three bridges 38, in each row of tabs 39 across the array 30, there are six tabs.

Frame 32 is further formed to have a number of beams 40. Each beam 40 extends from one bridge 38 to the adjacent bridge 38. In the illustrated version of the invention, beams 40 are arranged in longitudinally aligned pairs. Each beam 40 that extends inwardly from one outer bridge 38 to the center bridge 38 is aligned with a complementary beam that extends inwardly from the outer bridge 38 to the center bridge 40. Along the length of the frame 32, the beams 40 are longitudinally spaced from the tabs 39.

The electrodes 34 are disposed on frame tabs 39. A number of arrays 30 are constructed so that each electrode 34 is essentially disposed over a separate one of the tabs 39.

Also part of the electrode array 30 are application specific integrated circuits, ASICs, (not illustrated). These ASICs, which are not part of the present invention, contain current sources and current sinks. These current sources and current sinks are connected to the electrodes 34. Some electrode arrays 30 with which the present system 30 is used are constructed so that the ASICs are seated in openings formed in the frame 32. Other electrode arrays 30 are designed so that ASICs are seated on the surface of the frame 32. Conductors, again not illustrated and not part of this invention, are disposed on the frame 32. The conductors are the array components over which power and command signals are forwarded to the ASICs. The conductors serve as array components over which signals from the ASICs are transmitted off the array 30. Insulating layers, also not part of this invention and not illustrated, electrically insulate the components of array 30 and protect the array from the environment.

A cable 45 extends away from frame foot 36. Cable 46 contains wires (not illustrated) that are connected to the on-array conductors. The proximal end of cable 45 extends at least partially through the body of the patient. Cable 45 is connected to an implantable device controller (IDC) 46. The IDC 46 contains the power supply (battery pack) that powers the electrode array 30. The IDC 46 also contains a processor that both generates the instructions that regulate the operation of the electrode array and that monitor the operation of the electrode array.

It should be understood that the structure of electrode array 30 and IDC 46 is not part of the present invention. For example, the electrode array may have conductors, vias, insulating layers and membranes the structure of which, unless otherwise described, is not part of the present invention. This invention may be used with the electrode arrays that are the subject of the Applicant's Assignee's PCT App. No. PCT/US/2010/044401 published as WO 2011/017426 and US Pat. Pub. No. US 2012/0310316 A1 and PCT App. No. PCT/US2010/059691 filed 9 Dec. 2010, published as US 2012/0330393 A1, each of which is incorporated herein by reference.

III. Handpiece

Figure 6:
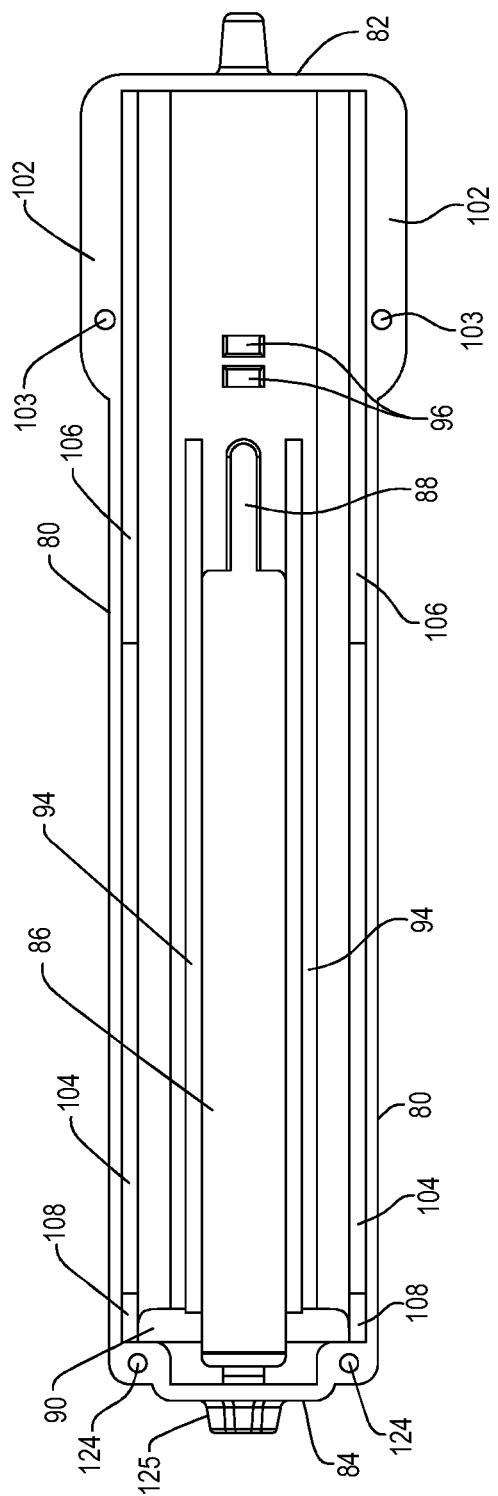
FIG. 6 is a plan view looking into the base of the handpiece.
Figure 7:
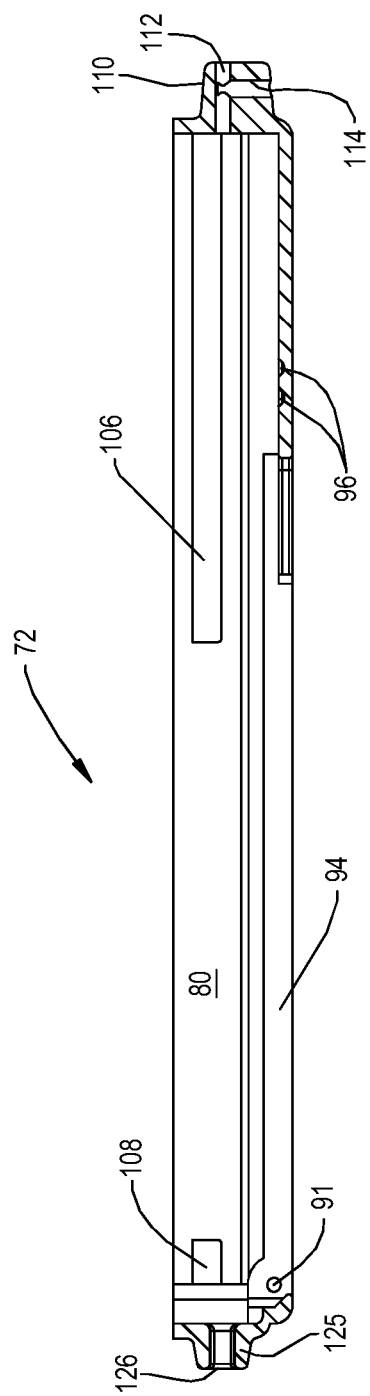
FIG. 7 is a cross sectional view of the handpiece base.

Handpiece 52 includes a base 72 and cover 74 that collectively form the housing or shell of the handpiece. Both the base 72 and cover 74 are formed plastic such as an ABS or polycarbonate plastic. Base 72, now described by reference to FIGS. 5-7, includes a bottom panel 78, two side panels 80, a proximal panel 82 and a distal panel 84. Bottom panel 78 is generally in the form of an elongated rectangle. In some versions of the invention, bottom panel has a length between 15 and 30 cm. In still other versions of the invention, bottom panel has a length between 18 and 25 cm. A two section slot extends through the bottom panel 78. The slot includes a distal section 86. Distal section extends 86 extends rearwardly from a position immediately proximal to the distal end of panel 78 a distance of around 55 to 65% of the length of the panel. Contiguous with and located proximal to slot distal section 86 is proximal section 88. The slot proximal section 88 is narrower in width than slot distal section 86. Slot proximal section 88 extends rearward from the proximal end of the distal section 86 a distance of approximately 10% of the overall length of the bottom panel. Both slot sections 86 and 88 are longitudinally aligned with and symmetric around the longitudinal center axis of the bottom panel 78.

At the forward distal of the base 72, a reinforcing rib 90 extends upwardly from the inner surface of bottom panel 78. The distal end of slot distal section bisects rib 90. A bore 91 extends side to side across the base 72 through rib 90. The opposed ends of the bore 91 thus form openings in the opposed curved outer surfaces of the base that form the transition sections between the bottom panel 78 and the side panels 80.

The base 72 is further formed so as to define a notch 92. Notch 92 is located in the portion of rib 90 located forward of the distal end of slot distal section 86. Notch 92, like slot sections 86 and 88, is centered on the longitudinal axis that extend along base bottom panel 78. Base 72 is further formed so as to have two parallel ribs 94 that extend upwardly from the inner face of surface of bottom panel 78. Ribs 94 extend upwardly from the opposed longitudinally extending sections of the bottom panel 78 that define the opposed sides of slot distal section 86. The ribs 94 extend distally from rib 90. Relative to the inner face of the base bottom panel 78, ribs 94 are shorter in height than rib 90. The rails 94 extend proximally rearward of the proximal end of slot distal section 86. Specifically, the ribs 94 extend to a longitudinal position along the inner surface of the bottom panel approximately equal to where the proximal end of slot proximal section 88. The proximal sections of ribs 94 are spaced laterally away from the sides of slot proximal section 88. Ribs 94 provide structural strength to base 72.

Base bottom panel 78 is further shaped to have two longitudinally spaced apart divots 96 that extend inwardly from the inner surface of the panel. Divots 96 are located proximal to the proximal end of slot proximal section 88. The divots 96 are centered on the longitudinal axis of the base panel 78. The openings defined by the divots 96 are rectangularly shaped. In cross section, in a plane that extends longitudinally through the base panel 78, each divot has a semi-circular shape.

Side panels 80 extend upwardly from the opposed longitudinal sides of bottom panel 78. Not identified are curved corners that form the transition sections of the base 72 between the bottom pane 78 and the side panels 80. Each side panel 80 is formed so as to have a shoulder 102 that extends outwardly from the outer surface of the panel. Each shoulder 102 extends forward from the proximal end of the panel 80 with which the shoulder 102 is integral. Each shoulder 102 extends forward a distance approximately 15 to 25% of the length of the panel 80. The distal end of the shoulder 102 curves into the rest of remainder of the side panel 102. Each shoulder 102 is formed to have a threaded bore 103. The bore 103 extends inwardly from the exposed face of the shoulder 103, the face against which cover 72 abuts.

Within the base 72, each side panel 80 is shaped to have a step 104. Step 104 is defined by the curved, corner-defining section of the base that is transition between the bottom panel 78 and the side panel 80 with which the step is integral. Each step 104 thus extends perpendicularly inwardly from the inner surface of the associated side panel 80. Steps 104 extend the length of side panels 80.

Two collinear ribs 106 and 108 extend inwardly from the inner surface of each side panel 80. Ribs 106 and 108 have an identical rectangular cross sectional shape. Rib 106, the proximal rib, extends distally forward along the associated side panel 80 from the adjacent inner face of proximal panel 82. Each rib 106 extends forward to a position forward of the proximal end of the slot distal section 86. Ribs 108 are the distal ribs. Each rib 108 is aligned with the associated proximal rib 106. Each rib 108 extends forward from a position immediately proximal to the proximal end of base panel rib 90. Adjacent the inner faces of each side panel 80 where ribs 106 and 108 are present, the ribs extend over and are spaced above the underlying steps 104.

Proximal panel 82 extends upwardly from the proximal end of base panel 78. The proximal panel 82 extends between the proximal ends of the shoulders 102 located at the ends of the side panels 80. Proximal panel 82 is generally a planar structure. A tail 110 extends proximally rearward from the exposed outer face of the proximal panel 82. Tail 110 is generally oval shaped. The tail 110 is oriented so that the major axis of the tail is a vertical axis, an axis that that extends perpendicularly upwardly from the plane 82 in which the base panel is seated.

Figure 5:
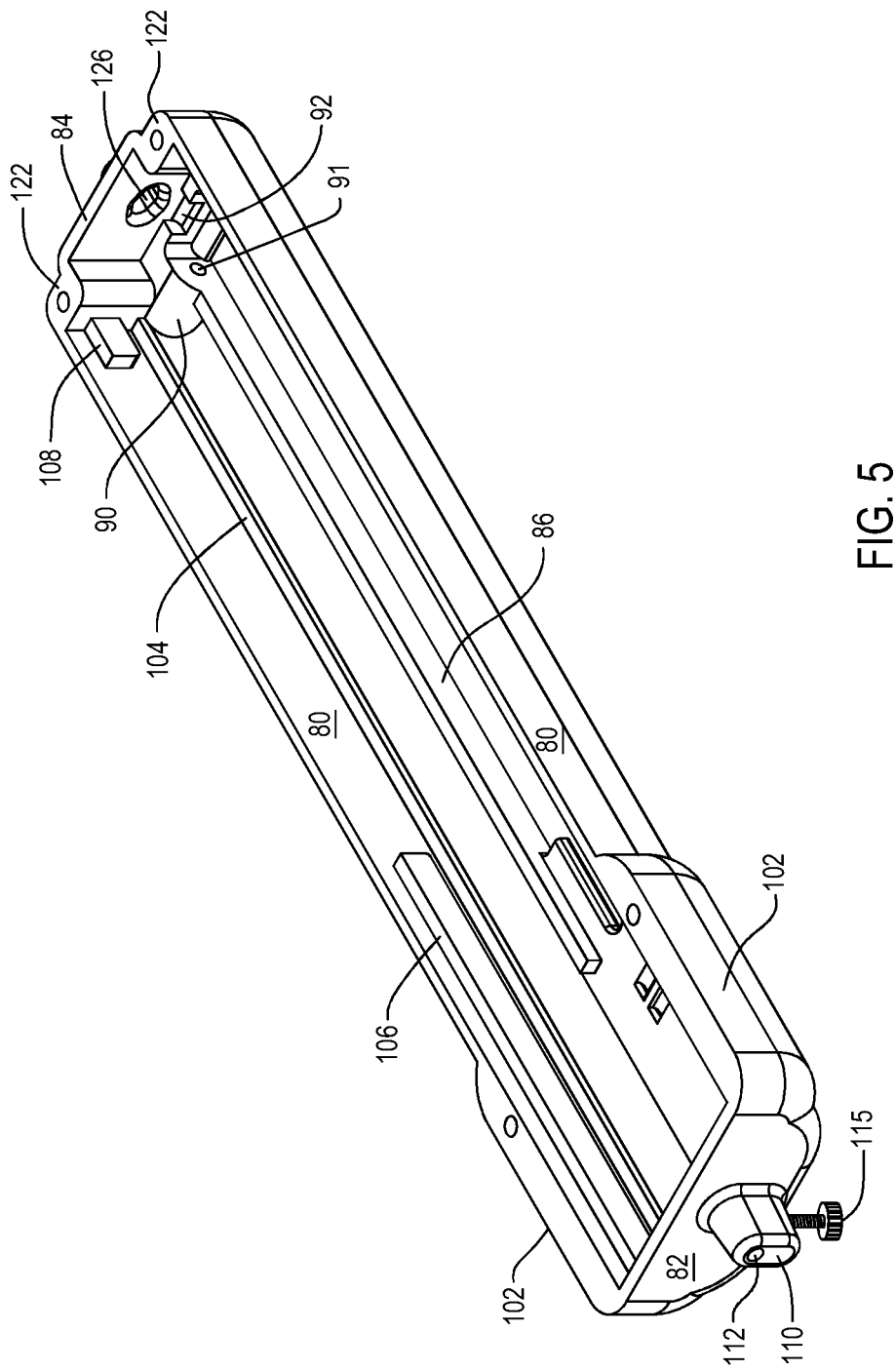
FIG. 5 is a perspective view looking into the base of the handpiece.

The handpiece base 72 is further formed so that there are two bores in tail 110. One bore, bore 112, is oriented along an axis that is parallel to the longitudinal axis of the base. Bore 112, extends both through proximal panel 82 and tail 110. Bore 112 functions as an opening into base 72. Owing to the shape of base 72, bore 72 is located above the center of tail 110. The second bore, bore 114 is a threaded bore (threading not identified). Bore 114 extends vertically, from the bottom of the tail into bore 112. A set screw 115, seen only in FIG. 5, is seated in bore 114.

Two stanchions 122 extend upwardly from the opposed corners of the distal ends of the bottom panel rib 90. The outer side surface of each stanchion 122 essentially forms the distal end of the associated side panel 80. The distal ends of ribs 108 abut the adjacent proximally directed faces of stanchions 122. A threaded bore 124 extends inwardly from the exposed face of each stanchion, the face directed towards the overlying cover 74.

Base distal panel 84 extends forward from the upper portion of the base panel rib 90 and sections of stanchions 122 located inwardly of the side panels 80. Distal panel 84 is thus located forward of the base panel 78 and side panels 80. It should further be appreciated that the outer perimeter of the distal panel is located inwardly of the outer surfaces of the base panel 78 and side panels 80.

A nose 125 extends forward the outer surface of distal panel 84. Nose 125 has generally an elliptical shape. Base 72 is formed so that major axis of the nose is in a plane parallel to and located above the plane in which base panel 78 is seated. An elliptically shaped bore 126 extends through both base panel 84 and nose 125. The longitudinal axis through bore 126 is coaxial with corresponding axis of bore 112.

Figure 9:
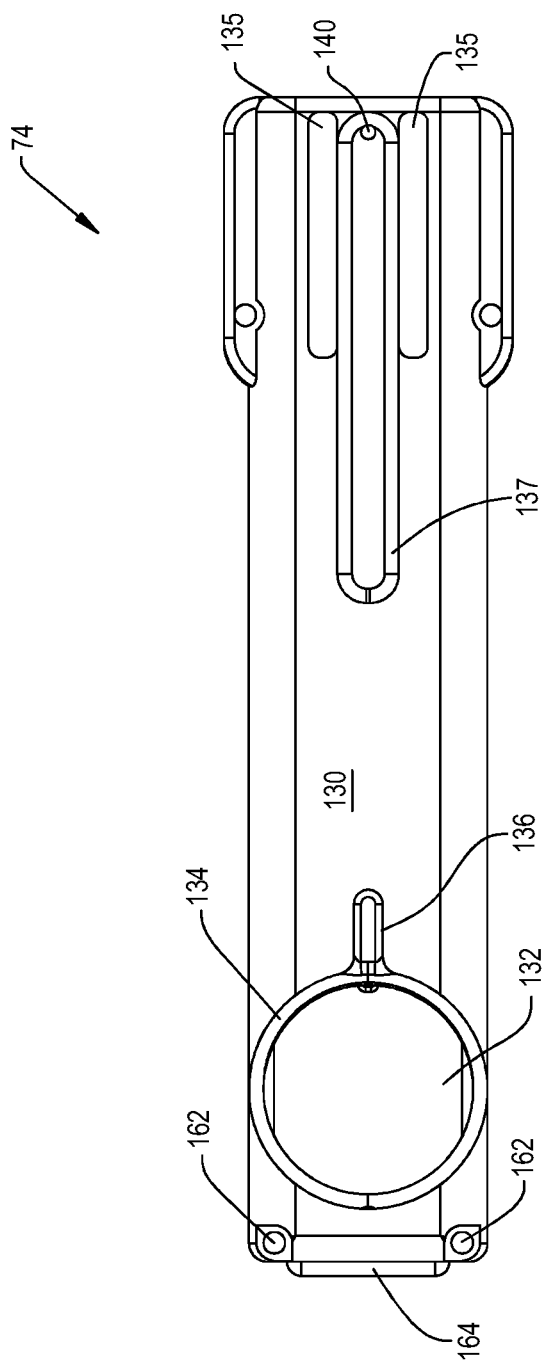
FIG. 9 is a top plan view of the handpiece lid.
Figure 10:
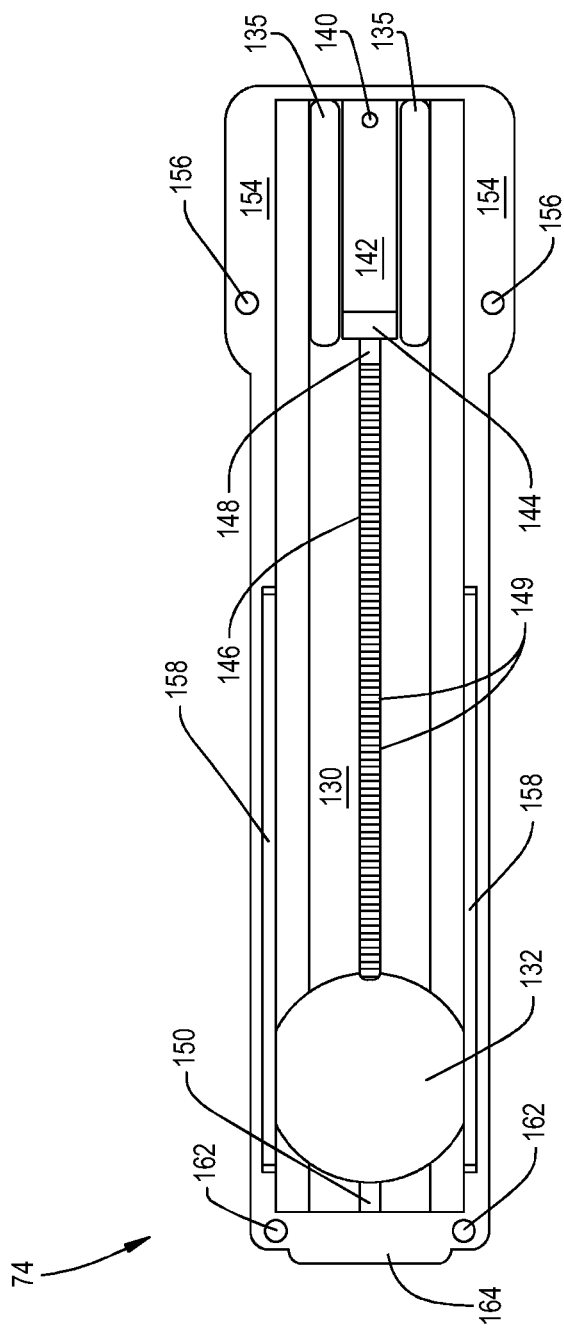
FIG. 10 is a bottom plan view of the handpiece lid.

Handpiece lid 74, now described with reference to FIGS. 8-10, includes a top panel 130. Top panel 130 has the same general length and width as base bottom panel 78. A short distance proximal to the distal end of the top panel 130, lid 74 is formed to have a circular through hole 132. A raised ring 134 extends upwardly from the outer surface of top panel 130. Ring 130 defines hole 132. The height of ring 134 above top panel 130 varies along the length of the panel. Specifically the most proximal portion of the ring extends above the top panel a relatively short distance forward of this portion of the ring 130, the height of the ring increases incrementally. The most distal portion of ring 134 is the tallest portion of the ring. The ring 134 is formed so as to have a through opening 133 in the most distal section of the ring. Opening 133 extends radially through the ring 134 and downwardly towards the most proximal portion of the ring, Lid top panel 130 is further formed to have two parallel elongated slots 135. Slots 135 extend forward from a location immediately distal to the proximal end of the panel 130. The slots 135 occupy a length that extends approximately 20% of the total length of the top panel 130. The slots are symmetrically spaced from and parallel to the longitudinal axis of the lid 74.

A first reinforcing rib 136 extends above the outer surface of the top panel 130. Rib 136 extends distally from ring 134. A second reinforcing rib 137, spaced proximally from rib 138 is also disposed over the outer surface of top panel 130. Rib 137 is located between slots 135. Rib 137 extends distally forward from a location adjacent the proximal ends of the slots 136. Rib 137 extends forward of the slots 136. Rib 137 has an overall length approximately two times the length of the slots. Ribs 136 and 137 are axially aligned. A small bore 140 extends through rib 137 and the underlying portion of top panel 130 immediately forward of the proximal end of the rib.

A closed end bore (not illustrated) also extends through most proximal portion of ring 134 into rib 136. This bore has the same diameter as and is coaxially aligned with ring opening 133.

Three collinear, longitudinally spaced apart ribs extend downwardly from the bottom surface of the lid top panel 130. The ribs are centered on the longitudinal axis of the panel 130. A first one of the ribs, rib 142, extends forward from the proximal end of the top panel 130. Rib 142 extends downwardly from the portion of the top panel 130 located between slots 135. The width of the rib 142 is slightly less than that of the width of the section of the top panel 130 between the slots 135. Rib 142 extends forward to a position proximal to the distal end of the slots 135. Bore 140 extends through rib 137 into and through rib 142. The lid 74 is shaped so that rib 142 has a distally directed face 144 with a concave profile. Face 144 curves downwardly and proximally away from the surface of the top panel 130 from which the face emerges. Face 144 has a radius of curvature of approximately 5 mm.

Spaced forward and away from rib 142, a second rib, rib 146, extends downwardly from the undersurface of the top panel. Rib 146 extends forward to panel through hole 132. The rib 146 has a width less than the width of rib 142. Rib 146 is shaped to have at its proximal end a distally directed face 148. Rib face 148, like adjacent rib face 144, has a concave shaped profile. Thus, forward of where the rib face 144 emerges from undersurface of the top panel 130, rib face 150 curves downwardly and proximally forward. The outer surface of the rib 146, the surface that faces the base bottom panel 78, is formed with ridges 149. The ridges 149 extend across the rib 146 and, along the rib 146, are longitudinally spaced apart from each other.

A rib 150 is the distalmost of the three collinear ribs 142, 146 and 150. Rib 150 extends forward from through hole 132 to the distal end of the top panel 130. Ribs 146 and 150 are of the same width. Unlike with rib 146, the outer surface of rib 150 is smooth.

A rim 152 curves downwardly and outwardly from each side of the top panel 130. Lid 74 is shaped so that the bottom surface of each rim 152 will abut the adjacent top surface of each base side panel 80. Opposed tabs 154 extend outwardly from the proximal ends of the rims 152. Tabs 154 are planar in shape. Lid 74 is shaped so that, when the lid is seated over base 72, each tab 154 seats over one of the base shoulders 102. Each tab 154 is formed with a through bore 156. Bores 156 are positioned so that when each tab 154 is seated over the complementary base shoulder 102, the bore is in registration with an underlying shoulder bore 103.

Lid 74 is further shaped so that forward of each tab 154, a bar 158 extends downwardly from each rim 152. Each bar 158 is shaped so that, when the lid 74 is disposed over the base 72, the bar slip fits into the space between the distal end of the adjacent base rib 106 and the proximal end of the adjacent base rib 108. The bars 158 are further dimensioned so that, when the handpiece 50 is assembled, the ends of the bars are located above the underlying steps 104 integral with base 72.

The lid 74 is further shaped to have a proximal panel 162. The proximal panel 162 extends downwardly from the proximal end of the top panel 130 and between the proximal ends of the rims 152. When the lid 74 is disposed over the base 72, the lid proximal panel 162 abuts the underlying base proximal panel 82.

The distal end of the lid top panel 130 is formed with a downward curving surface, (not identified). The top panel 130 is also formed to have two through bores 162; one bore 162 in each distal end corner. When the lid 74 is disposed over base 72, each lid bore 162 is in registration over one of the base bores 124. In the illustrated version of the invention, the lid top panel 130 is formed so that at each distal end corner there is a notch (not identified). Each bore 162 extends through the lid 74 from the base of the associated notch.

A nose 164 extends forward from the most distal end of the lid top panel 130. Nose 164 has a length, along the axis perpendicular to the longitudinal axis of the lid 74, less than width across the top panel 130. The nose 164 extends forward from the bottommost portion of the distal end of the top panel. The top of the nose 164 is located below the outer surface of the top panel 130. The lid 74 is shaped so that when the lid is seated over the base 72, lid nose 164 abuts base distal panel 84.

Figure 11:
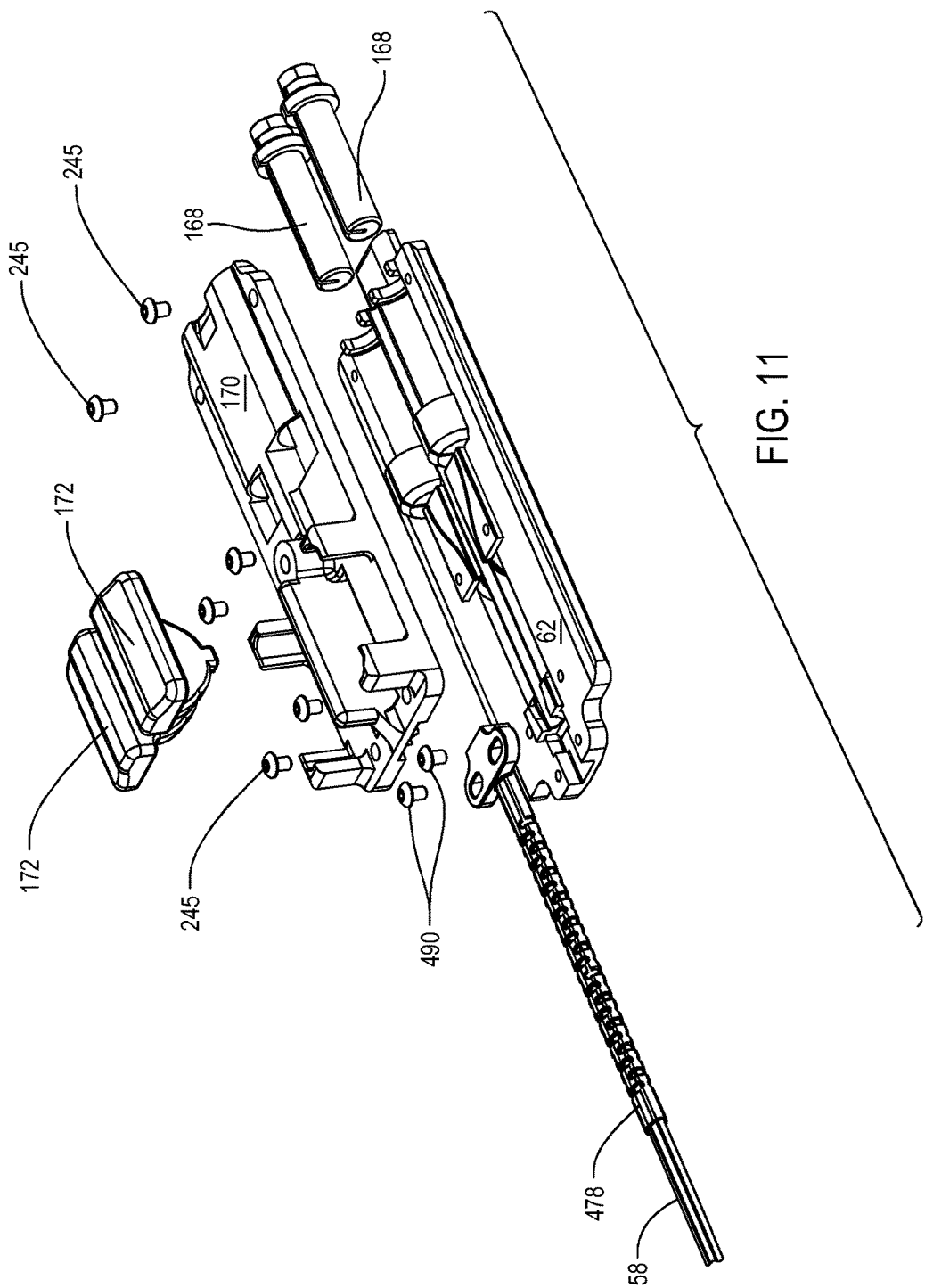
FIG. 11 is an exploded view of the distal slide and the components mounted to the distal slide.

The distal slide 62, and the components attached to the slide are initially described by reference to FIG. 11. The slide 62 is a generally rectangularly-shaped component dimensioned to seat on and slide over base steps 104. The proximal end of the sheath 58 is secured to the distal end of the slide. Steering cables 60 extend rearwardly out of the sheath and over the surface of the slide 62. The proximal end of each steering cable 60 is attached to tensioner 168. Each tensioner 168 is mounted to the slide 62. A plate 170 is disposed over the exposed surface of the slide 62. Plate 170 holds the steering cables 60 and tensioners 168 to the distal slide 62.

Two steering blocks 172, part of steering unit 66, are moveably mounted to both the distal slide 62 and plate 170. Each steering cable 60 is threaded through a separate one of the steering blocks 172.

Figure 12:
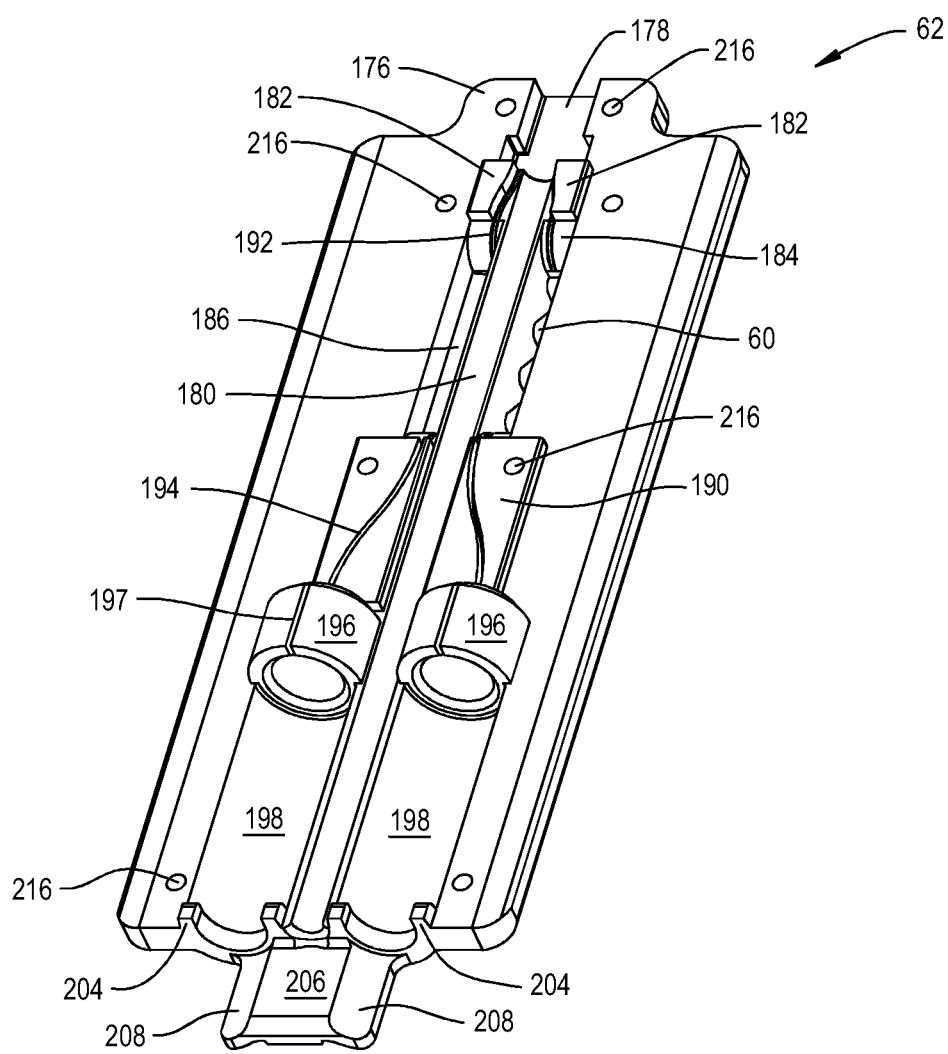
FIG. 12 is a perspective view of the top of the distal slide.
Figure 13:
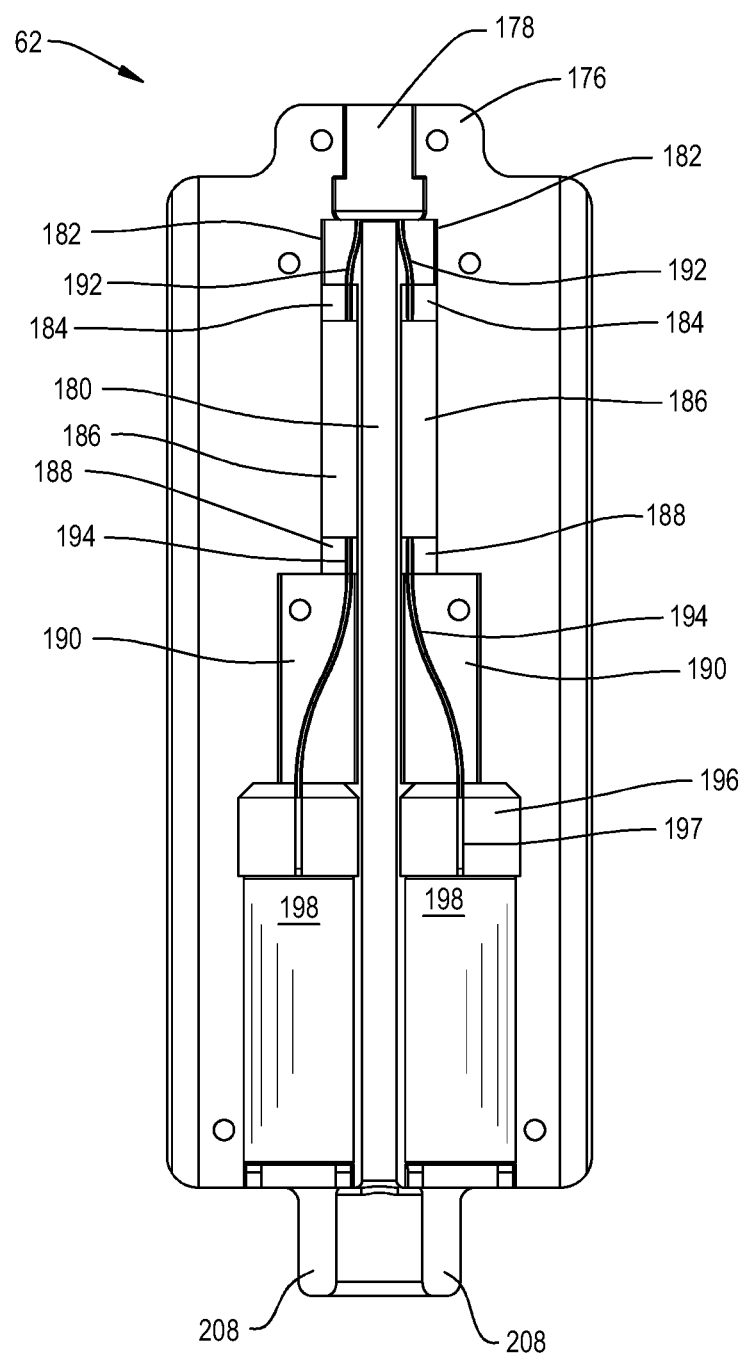
FIG. 13 is a plan view of the top of the distal slide.
Figure 14:
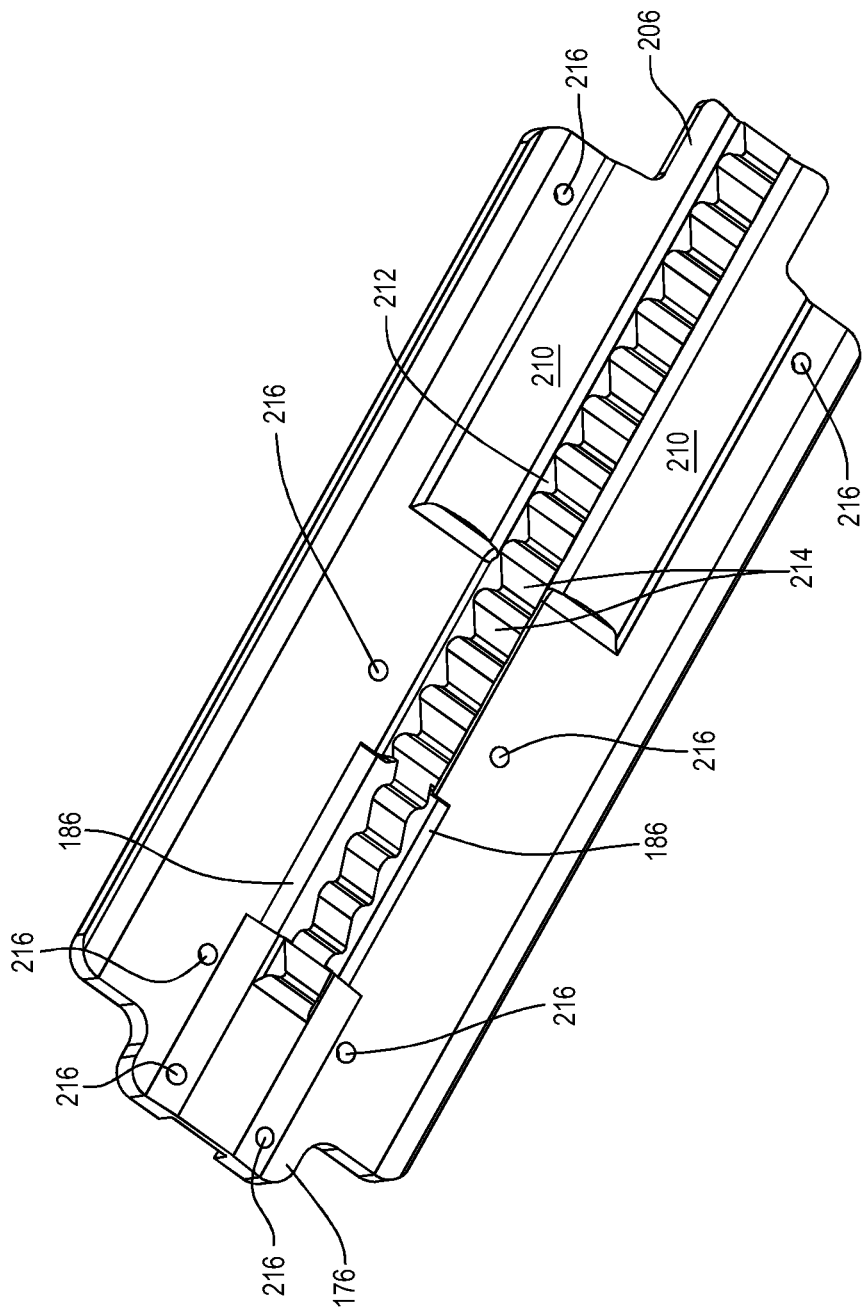
FIG. 14 is a perspective view of the underside of the distal slide.

The distal slide 62, now described by reference to FIGS. 12, 13 and 14, is formed from a plastic such as ABS. The distal slide is generally rectangularly shaped. The slide 62 has a width that is approximately 1 to 2 mm less than the distance between the base side panels 80. This allows the slide, when seated on base steps 104, to move longitudinally within the base 72. Extending forward of the main body of slide 62, the slide is shaped to have a nose 176. The nose 176 is formed to have width, a dimension perpendicular to the longitudinal axis of the base 72, that is less than the width of the body of the slide 62. Distal slide 62 is further formed to have to have in its outer surface, a T-shaped indentation 178 that extends proximal rearward from the distal end of nose 176. The indentation 178 is T-shaped in that the portion of the indention that extends longitudinally across the nose 176 has a narrow width; the portion of the indentation that located in the most distal portion of the body of the slide 62 has a wider width.

The distal slide 62 is further formed to have a groove 180 that extends proximally from indentation 178. Groove 180 extends the length of the body of slide 62 and is centered on the longitudinal axis of the slide. The slide 62 is formed so that the groove 180 has a semi-circular cross sectional shape. Distal slide 62 is further formed to have two laterally spaced apart blocks 182 that extend approximately 2 to 3 mm upwardly from the top surface of the slide. Blocks 182 are located immediately proximal to the proximal end of indentation 178. The blocks 182 are on opposed sides of section of the slide 62 that defines groove 180. Blocks 182 are formed so that three faces of each block, the distally directed face, the outwardly directed face and the proximally directed face, are planner. The inwardly directed faces of the blocks 182, the faces of the blocks that are directed towards each other, are curved. Specifically, each face is curved so that, as the face extends proximally, away from nose 176, the face curves outwardly, away from the longitudinal axis of the slide 62.

The distal slide 62 is also shaped to have two rectangularly shaped openings 186. Each opening 186 is spaced proximally from one of the blocks 62. Each opening 186 essentially boarders the axial section of the base of the slide in which groove 180 is formed. Between the proximal end of a block 182 and the distal end of the aligned opening 186, the slide is further formed to have a ramp surface 184. Extending distally from the block, the ramp surface 184 curves downwardly towards the underside of the slide. Ramp surfaces 184 have convex profiles. In FIG. 12 a set of wavy lines represent a slack section of a steering cable 60 in one of the openings 186. This is to represent that, as described below, when handpiece 52 is assembled, a section of each steering cable 60 extends into each opening 186.

Proximal to the proximal ends of openings 186, distal slide is formed to have ramp surfaces 188. The distal end of each ramp surface 188 defines the proximal end of each opening 186. Extending proximally, each ramp surface 188 curves upwardly. Ramp surfaces 188 have a convex shape. The distal slide has two pads 190. Each pad 190 is rectangularly shaped and extends approximately 2 to 3 mm above the outer surface of the slide base. Pads 190 boarder the section of the slide 62 that defines the laterally adjacent sections of groove 180. Each ramp surface 188 essentially terminates at the proximal end of the adjacent pad 190.

The distal slide 62 is also formed with two pairs of channels. A first pair of channels, channels 192, is located immediately proximal to indentation 178. Each channel 192 is located immediately inward of the inwardly directed face of an associated one of the blocks 182. Each channel 192 is located between the associated block 182 and the adjacent groove 180-defining section of the slide. Channels 192 extend in ramp surfaces 184 and extend to the proximal ends of the ramp surfaces. The portion of each channel 190 adjacent a block 182 curves with the adjacent block inwardly directed face. The portion of each channel 190 formed in a ramp surface 184 extends linearly to the adjacent opening 186. Owing to the curvature, it should be understood that the distal end of each channel is located closer to the longitudinal axis of the distal slide 62 than the channel proximal end.

The second pair of channels, channels 194, are formed in ramp surfaces 188 and pads 190. Channels 194, like channels 192, are symmetrically located around the longitudinal axis of the slide 62. The portion of each channel 194 formed in the ramp surface 188 is linear and collinear with the portion of channel 182 formed in ramp surface 184. The portion of channel 194 formed in the pad curves outwardly, away from groove 180. In the illustrated version of the invention, the proximal terminus of each channel 194 is located outwardly of the longitudinal center axis of the pad in which the pad 190 in which the channel is located.

Two symmetric grooves 198 are formed in the proximal section of the distal slide 62. Grooves 198 are located adjacent to and on opposed sides of the section of the slide 62 in which groove 180 is formed. Grooves 198 are semi-circular in shape and have a diameter greater than that of groove 180. Each groove 198 extends from a location adjacent the proximal end of the adjacent pad 190 to a location slightly distal to the end of the base of the slide 62.

Molded into so as to be integral with the distal slide 62 are two caps 196. Each cap 196 has a tube like body and, at its distal end, a circular top. Distal slide 62 is formed so that each cap 196 is molded into the distal end of one of a separate one of the grooves 198. The distal slide 62 is also formed so that a slot 197 extends longitudinally through each cap, including the distally directed head of the cap. Each slot 197 terminates at the point where the associated channel 194 meets the cap 196 in which the slot is formed. The distal slide is further shaped to have two U-shaped yokes 204. Each yoke 204 is located at the proximal end of one of the grooves 198. The yokes 204 extend above the surfaces of the slide 62 that define grooves 198.

Extending proximally rearward from the proximal end of the slide body, distal slide 62 is formed to have a tail 206. The distal slide 62 is shaped so that the tail 206 is located below the upper surface of the slide body. Tail 206 is formed so that on the upper surface there are two longitudinally extending side surfaces 208 that are recessed inwardly relative to the center top surface (not identified), the surface immediately below the proximal end of groove 180.

As seen in FIG. 14, distal slide 62 is formed to have an undersurface that is generally, though not completely, planar. The undersurfaces of the nose 176 and tail 206 are coplanar with the undersurface of the body. A pair of arcuately shaped, parallel, bulges 210 extend downwardly from the body undersurface. Bulges 210 are the portions of the body that define grooves 198.

A rack 212 extends downwardly from the undersurface of the distal slide 62. Rack 212 is located on the longitudinal axis of the slide 62. The rack 212 extends proximally from a location underneath blocks 172 under the remainder of the body and along the whole of the tail 206. Rack 212 is formed by a number of teeth 214. Each tooth 214 is in the shape of a right angle triangle wherein the distally directed surface extends perpendicularly downwardly from the slide body and the hypotenuse surface extends upwardly and proximally away from the bottom end of the distal surface (individual surfaces not identified).

The body of the distal slide 62 is further formed to have a number of threaded bores 216. In the illustrated version of the invention there are eight threaded bores. One bore 216 is located adjacent each forward corner of nose 176. There is one bore 216 located outward of each block 172. One bore 216 extends through each pad 190. Specifically, each of these bores 216 is located outward of the section of the channel 194 formed in the pad 190. The remaining two bores 216 are located immediately forward of the proximal end of the slide body. Each of these bores 216 is located outwardly of an adjacent groove 196.

Figure 15:
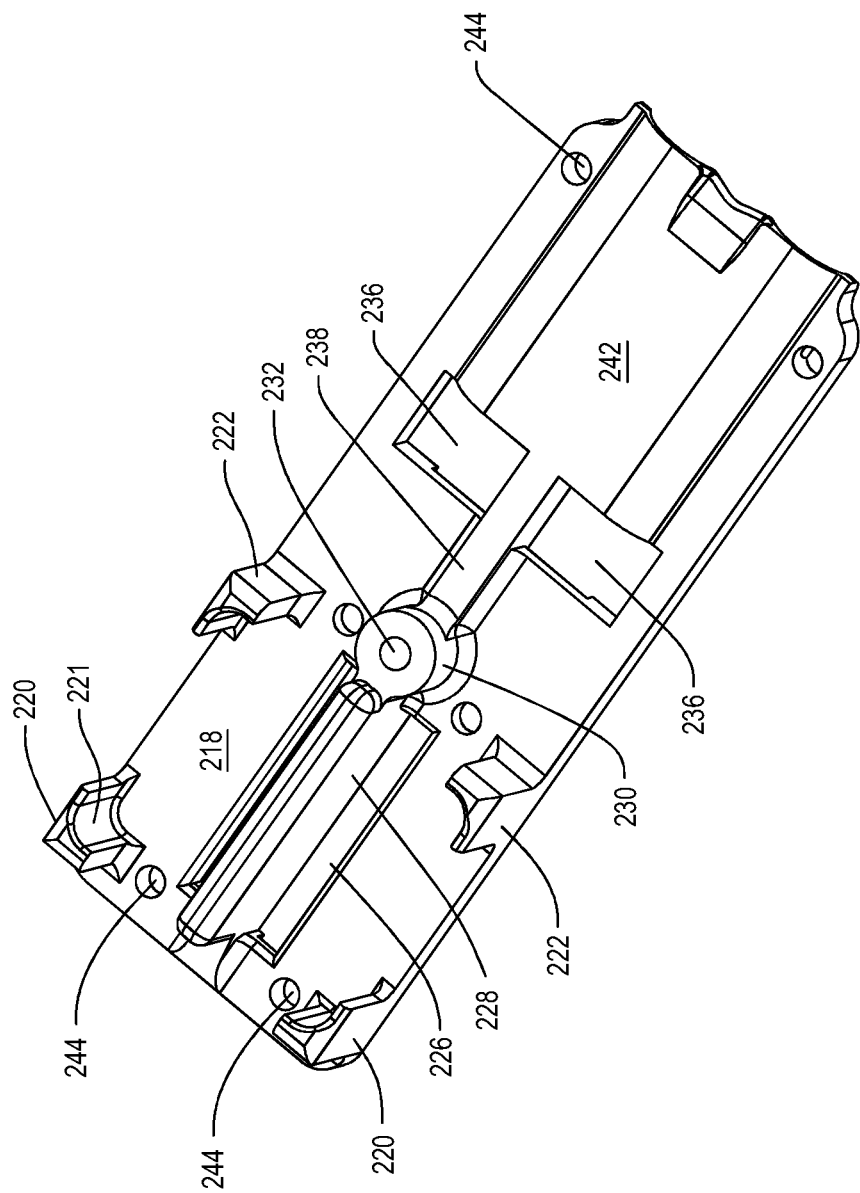
FIG. 15 is a perspective view of the plate disposed over the distal slide.
Figure 16:
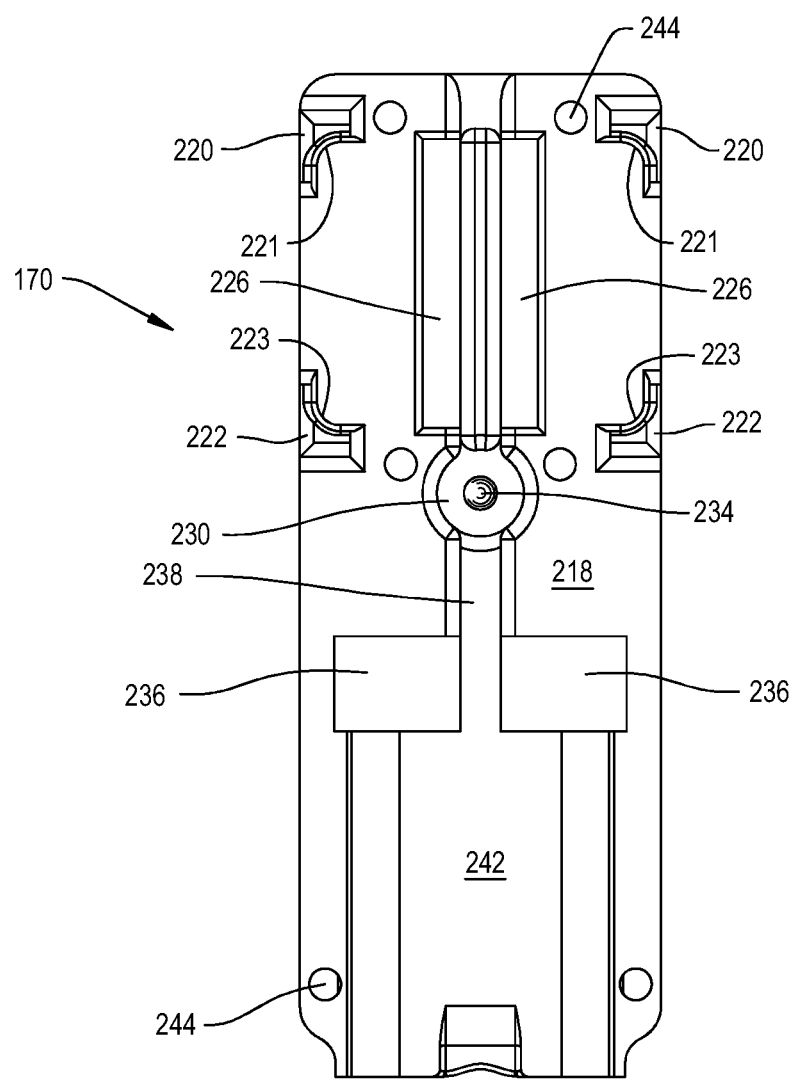
FIG. 16 is a top plan view of the plate of FIG. 15.

The plate 170 secured to the distal slide 62 is now described by reference to FIGS. 15-17. The plate 170 is formed from the same material from which the distal slide 62 is formed. Plate 170 has a length equal to and width slightly less than the corresponding dimension of the body of the slide 62. The plate 170 has a generally planer body 218. Two pairs of posts 220 and 222 extend upwardly from the top surface of the body. The two most distal posts, posts 220, are located immediately proximal to the distal end of the plate body 218. Each distal post 220 is shaped so to have distally directed and outwardly directed faces that are both planar and perpendicular relative to each other. Each distal post also has a planar inwardly directed face that extends proximally from the inner edge of the distally directed face. Between the opposed planner inner and outwardly directed faces each post has an inwardly curved face 221 that has a concave profile. Extending proximally from the contiguous inner directed planar face, this curved face 221 curves outwardly. Curved faces 221 of distal most posts 220 are directed towards each other.

The two proximal posts, posts 222, are symmetrical and identical to distal posts 220. Each proximal post 222 has an inwardly curved face 223 that is directed to both the curved face 221 of the adjacent distal post 220 and the curved face 223 of the laterally adjacent proximal post 222.

Plate 170 is further formed to have two openings 226. Openings 226 are rectangularly shaped and have a common width equal to the width across the distal slide openings 186. Each opening 226 has a length equal to the combined length of an opening 186 and the adjacent ramp surfaces 184 and 188. The plate 170 is formed so that, when the plate is disposed over the distal slide, each plate opening 226 is disposed over a separate one of the slide openings 186.

A panel 228, part of plate 170, is located between openings 226. The plate 170 is shaped so that panel 228 extends perpendicularly upwardly from the outer surface of the plate. The panel 228 extends a short distance proximally beyond openings 226. A circular boss 230 extends upwardly from the outer surface of plate 170 and is immediately proximal to the panel. A threaded bore 232 extends through the boss 230. Bore 232 is concentric with the center longitudinal axis of the boss. 230. A spring loaded ball 234, seen only in FIG. 16, is seated in bore 232. Ball 234 is positioned so as to extend above panel 228 and abut lid rib 146.

Extending forward from the proximal end, plate 170 is formed to a have a raised platform 242. Platform 242 has an outer surface that extends upwardly from the outer surface of plate body 218. Not identified are the curved sides of the platform 242 that form the transition between the body 218 and the platform. Immediately forward of platform 242, plate 170 is formed to have two rectangular openings 236 in the plate body 218. Each opening 236 is shaped to receive one of the exposed sections of one of the caps 198 integral with distal slide 62. Also integral with the plate 170 is a spine 238 that is located over the longitudinal axis of the plate. Spine 238 extends from boss 232, between openings 236, to platform 242. The spine 238 has a rectangular cross sectional shape.

A number of bores 244 extend through the plate body 218. Plate 170 is formed to have six bores 244. Plate 170 is shaped so that when the plate is disposed over the distal slide 62, the plate bores 244 are aligned with the six proximalmost bores 216 formed in the slide 62. In the illustrated version of the invention, the two most proximal bores 244 are located in the plate body 218 forward of the proximal end of the plate. The two middle-located bores 244 are formed in the body on the opposed sides of boss 230. Each middle bore 244 is thus located between the boss 230 and one of the proximally located posts 222. The distally located bores 244 are locate inwardly of the inner directed faces of the distal posts 222. The distal bores 244 are centered on axes located forward of the distal end of panel 228.

Figure 17:
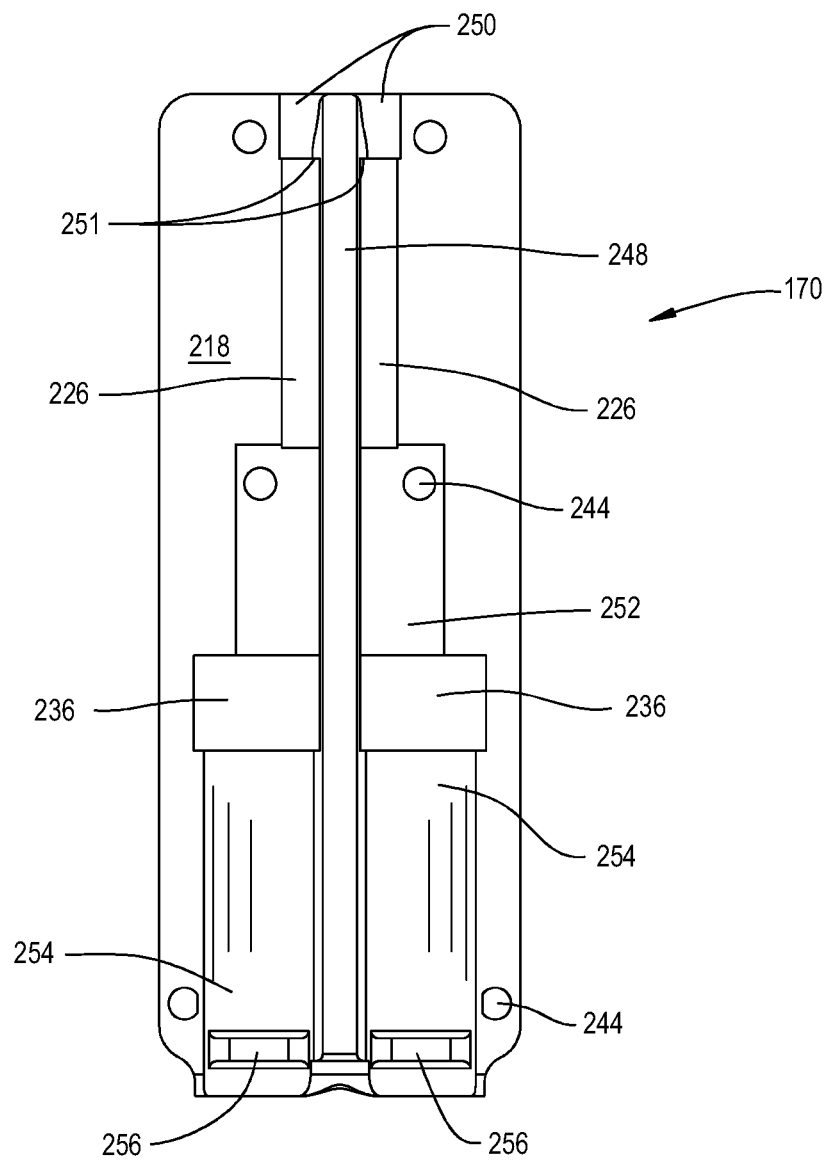
FIG. 17 is a bottom plan view of the plate of FIG. 14.

The undersurface of plate body 218 is generally planar as seen in FIG. 17. There are a number of upwardly extending indentations. One of these indentations is a semicircular groove 248 that extends along the longitudinal axis of the plate. Groove 248 has the same radius of curvature as slide groove 180. When the plate 170 is disposed over the distal slide, the plate groove 248 is in registration over slide groove 180.

The plate 170 is further formed so that extending proximally from the distal end there are two notches 250. Notches 250 are symmetric around the longitudinal axis of the plate 170. Each notch 250 is shaped to receive one of the blocks 182 integral with the distal slide 62. Each notch 250 has a cross sectional profile, in a horizontal plane, that allows a complementary distal slide block 182 to closely slip fit in the notch. Consequently, each notch 250 is partially defined by a tab 251 that extends upwardly from the base of the notch. Each tab 251 has a longitudinal surface that mirrors the adjacent curved surface of the associated block 182. Each tab 251 is integral with an internal portion of the plate 170 that defines the adjacent groove 248. Notches 250 open into plate openings 226.

Proximal to openings 226, the plate is formed to have two recesses 252 the distal ends of which are contiguous with the openings 226. Recesses 252 are located on the opposed sides of the sections of the plate that defines groove 248. Each recess 252 is shaped to have a rectangular shape. More particularly, plate 170 is shaped so that when the plate is seated over the distal slide 62 each slide pad 190 seats in one of the recesses 252. A bore 244 opens into each of the recesses 252.

Proximal to each opening 236, the underside of the plate platform 242 is shaped to define two semi-circular grooves 254. Grooves 254 have the same radius of curvature as slide grooves 198. The grooves 254 extend to the proximal end of the plate 170. When plate 170 is fitted over distal slide 62, plate groove 254 are disposed over slide grooves 198. Plate 170 is further formed so as to have an arcuate rib 256 that extends downwardly from the inner surface of each groove 254-defining surface. Ribs 256 are located forward of the proximal ends of grooves 254. When handpiece 52 is assembled, each rib 256 is in registration over a corresponding one of the slide yokes 204.

The structure of one of the steering cable tensioners 168 is a now described by reference to FIGS. 18 and 19. Each tensioner 168 includes a sleeve 258, formed from a thermoplastic such as ABS. Each sleeve 258 has a cylindrical body 259 with a distally directed head 260. A cylindrical closed end bore 261 extends distally forward from the proximal end of body. Body 259 has an outer diameter less than that of the inner annular wall of the cap 198 in which the sleeve 258 is seated. The sleeve 258 is further formed so as to have an annular collar 262 that extends radially outwardly around the body 259. Specifically, sleeve 258 is formed so that the collar 262 is located forward of the proximal end of the body. Collar 262 has an outer diameter that allows it to slip fit between the curved walls of the distal sleeve 62 and the plate 170 that, respectively, define a slide groove 198 and the complementary plate groove 254. The collar 262 is located on the sleeve 258 so that, when the sleeve is mounted to distal slide 62, the sleeve can move longitudinally approximately 4 to 8 mm within the annular space formed by the complementary grooves 198 and 254.

Sleeve 258 is further formed to have a slot 263 the extends longitudinally along the length of the sleeve. Slot 263 extends radially inwardly from the outer surface of the body 259 into bore 260. The slot 263 also extends through collar 262. Slot 263 extends radially through the sleeve head 260 so as to terminate in the center of the head. Slot 263 is dimensioned to facilitate the slip fitting of the steering cable 60 into the bore 264.

The proximal end of each steering cable 60 is secured to cylindrical anchor 264 also part of the tensioner 168. In FIG. 18, the cable 60 is shown as a broken line. Often anchor 264 a thermoformed plastic such as ABS and is molded over the proximal end of the steering cable 60. Anchor 264 is dimensioned to slip fit within sleeve bore 261. The outer surface of anchor 264 is formed with threading (not identified). A nut 265 is threaded over anchor 264.

Figure 18:
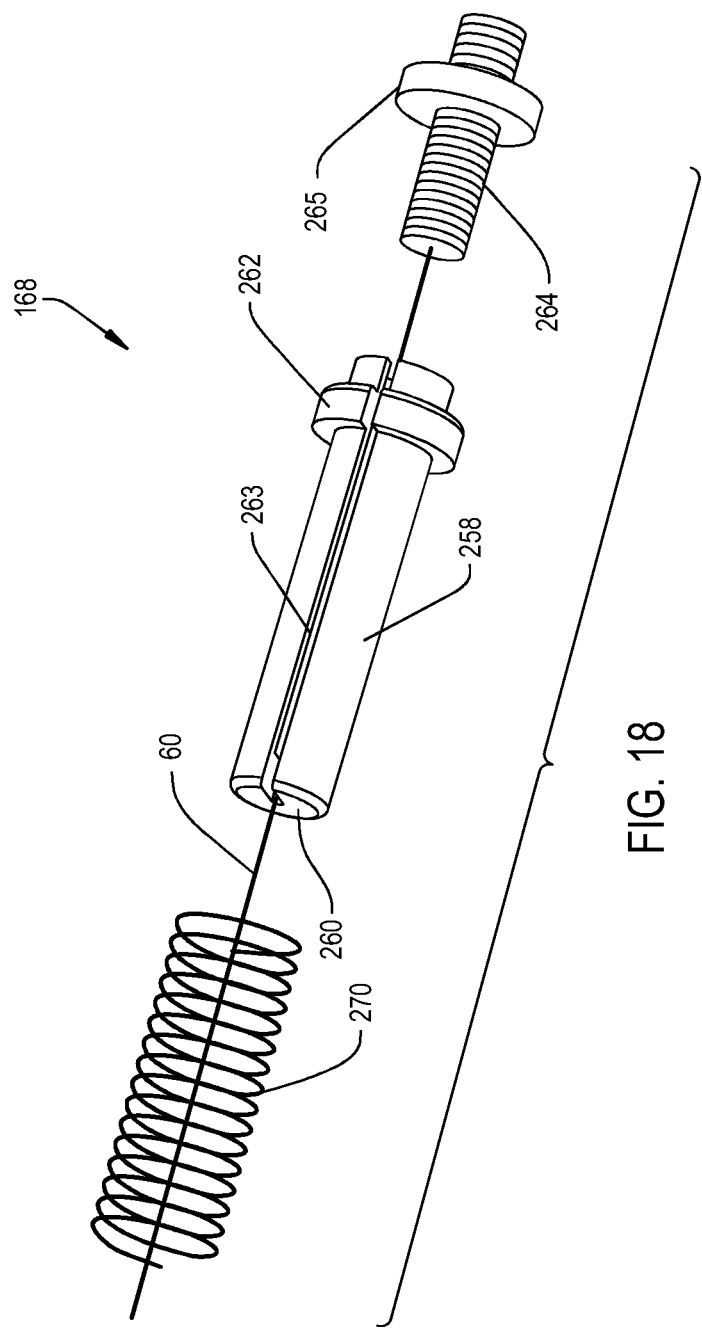
FIG. 18 is an exploded view of the components forming the steering cable tensioner and tension limiter.
Figure 19:
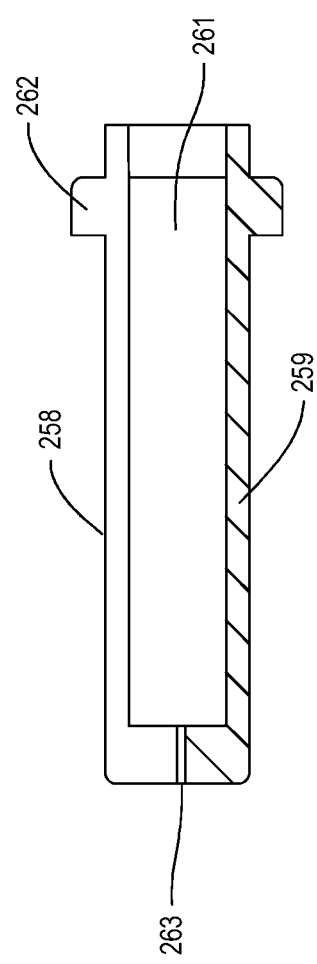
FIG. 19 is a cross sectional view of the sleeve of steering cable tensioner.

Each tensioner 168 also includes a coil spring 270, seen only in FIG. 18. Coil spring 270 is disposed around sleeve body 259. When the handpiece 52 is assembled, each spring 270 extends between the proximally directed face of the slide cap 198 and the sleeve collar 262. Each spring 270 urges the associated sleeve 258 rearwardly. The rearward movement of the sleeve 258 is limited by the abutment of the sleeve collar 262 against the distally directed surfaces of the slide yoke 204 and the plate rib 256. When the sleeve 258 so abuts the slide yoke 204 and plate rib 256, the proximal end of the sleeve, the portion of the sleeve body 259 proximal to the collar 262 extends through and a short distance beyond the yoke 204 and rib 256.

When handpiece 52 is assembled, a steering cable 60, with anchor 264 attached, is fitted in sleeve 258. Spring 270 is fitted over the sleeve 258. The sleeve 258 is fitted in the appropriate slide groove 198. The abutment of the sleeve collar 262 against the slide yoke 204 limits the spring-forced rearward movement of the sleeve 258 in the slide groove 254. During the final assembly of the handpiece 54, nut 264 is positioned on anchor 264 so that the nut bears against the proximally directed face of sleeve 258. As discussed below, the nut 264 is set to take up slack and place a tension on the steering cable 60.

Figure 21:
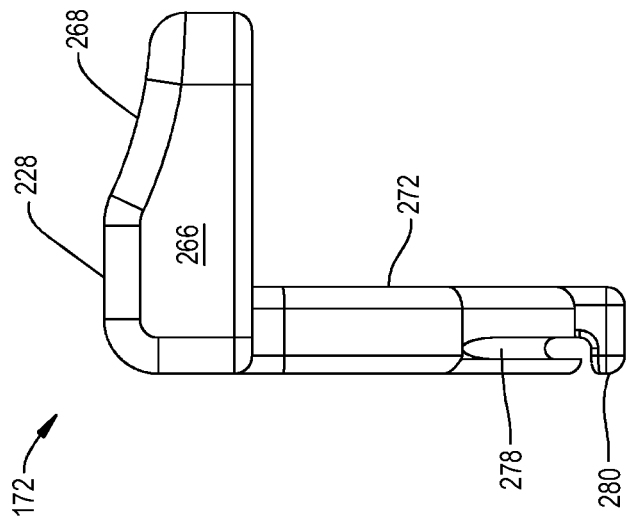
FIG. 21 is an end view of a steering block.
Figure 20:
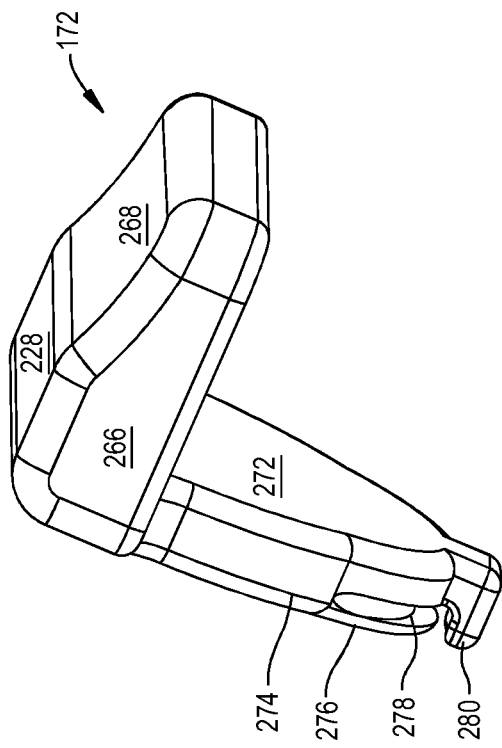
FIG. 20 is a perspective view of a steering block.

Steering blocks 172, one of which is seen best in FIGS. 20 and 21, are also formed from the same type of plastic from which distal slide 62 is formed. Each steering block 172 includes a head 266. The head 266 is generally in the form of a rectangle with rounded corners. The head 266 is dimensioned to fit with a slight clearance in the space defined between a pair of longitudinally aligned plate posts 220 and 222 and the plate panel 228. The outer corners of the head 266 are located inwardly of the adjacent curved faces 221 and 223 of, respectively, posts, 220 and 222. This dimensioning of the components of the handpiece 50 is to facilitate the relative free movement of the steering block 172 between the surrounding posts 220 and 222 and panel 228.

Each steering block head 266 is shaped to have an outwardly directed surface that is not planar. More specifically, the top surface is shaped to so as to define along the length of the outer side a step 268 that is recessed below the adjacent side surface, the surface proximal to the panel 228. The step 268 extends the length of the head 266. The opposed undersurface of the head 266, the surface that is directed towards plate 170, is planar (surface not identified).

A foot 272, also part of the steering block 172, extends downwardly from the head 266. Foot 272 extends downwardly from the inner side of the head 266, the side adjacent plate panel 228. Each steering block foot 272 has a cross sectional width that allows the foot to slide in one of the distal slide openings 186. Each foot 272 has a generally semi-circular shape. The foot 272 extends downwardly from the inner side of the shoulder, the side adjacent plate panel 228. Also, the foot 272 is centered on the head 266 such that the ends of the foot are spaced inwardly from the distal and proximal ends of the head. Steering block foot 272 is generally semi-circular in shape with a base section 274 adjacent the shoulder 228 that has a first radius of curvature. Below the base section 274 there is a head section 276 that forms the outer most end of the foot 272. Head section 276 has a second radius of curvature that is less than the first radius of curvature. Steering block foot 272 is further formed to have a groove 278 in its head section 276. Foot 272 is formed so that groove 278 extends arcuately along and in the outer arcuate face of head section 276. Groove 278 is dimensioned to receive one of the steering cables 60. The groove 278 does not extend along the center axis of the face. Instead, the groove is formed in the portion of the face adjacent the inner face of the head, the face that is located closest to the plate plane 228.

Each steering block 172 is also formed to have L-shaped toe 280 that extends radially outwardly from the portion of foot 276 most distal to head section 266. Toe 280 extends outwardly from the outer portion of the arcuate face of the head section, the portion of the arcuate face that is adjacent to and outward from the section in which the groove 278 is formed. The outer end of the toe 280 is disposed over and spaced away from the inner portion of the arcuate face of the head section, the portion of the head section in which groove 278 is formed.

When the handpiece 52 is assembled, each steering cable 60 is positioned over the distal slide 62 so that the cable is seated in the slide groove 192, extends through the adjacent opening 186 and is seated in the associated slide groove 194. As described above, the most proximal end of the cable is attached to the tensioner 168. Plate 170 is disposed over the body of the distal slide. Fasteners 245 extend through plate openings 244 into slide openings 216 to hold the plate 170 to the slide 62. Plate 170 thus holds the steering cables 60 and tensioners 168 to the distal slide 172.

Each steering block 172 is fitted to the slide-and-plate assembly so the block foot 272 is seated in one of plate openings 226 and underlying slide opening 186. Each steering block foot 276 is thus located adjacent the panel 228 that extends upwardly from plate 170. The section of the steering cable 60 that extends through the slide opening 186 is threaded into the groove 278 formed in the block foot 272. The steering cable is thus disposed between the block foot 272 and toe 280.

Figure 23:
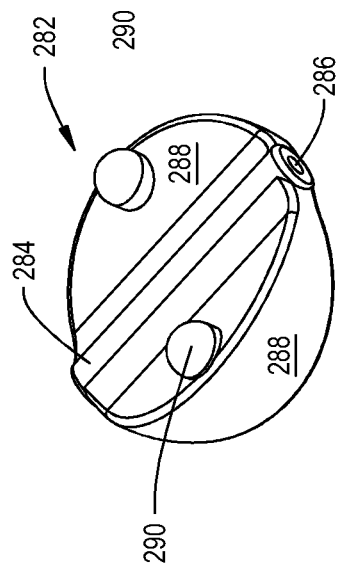
FIG. 23 is a perspective view of the underside of the steering button.
Figure 22:
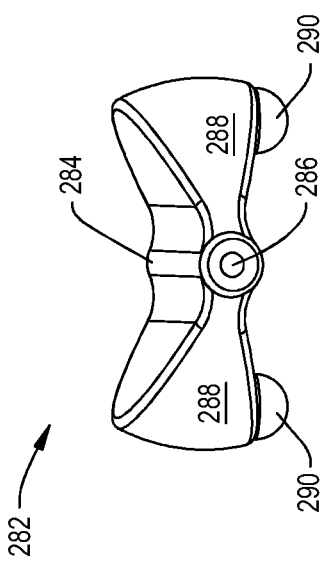
FIG. 22 is a perspective view of the steering button.

Handpiece steering unit 66 also includes a control button 282 that is pivotally attached to the lid 74. The button 282, now described by reference to FIGS. 22 and 23, is formed from the same material from which lid 74 is formed. Generally, the control button 282 has a circular shape. More particularly, the diameter of the control button 282 is slightly less than that of lid hole 132. The relative dimensioning of the lid 74 and button 282 is to allow the button to freely pivot within the hole 132.

Button 282 is further shaped to have spine 284 that is generally cylindrically shaped. Spine 284 extends the longitudinal length of the button 282. The button 282 is further formed to have bore 286 that extends axially through the spine 284. Two wings 288 that are symmetric with each other around the spine 284 extend laterally away from the opposed sides of the spine. Immediately adjacent the spine 284 the wing thickness, the distance through the wing, is less than the distance through the spine. The button 282 is shaped so that, as the distance from the spine 284 increases, the wing thickness also increases. Thus each wing 288 approximately has the shape of a pole-to-pole slice section through a sphere.

A boss 290 extends downwardly from the underside of each wing 288. The bosses 290 extend downwardly from the sections of the wings located laterally to the spine. A line between the bosses 290 crosses the spine at 90°. Each boss 290 has an outermost face that is semi-spherical in shape.

Figure 8:
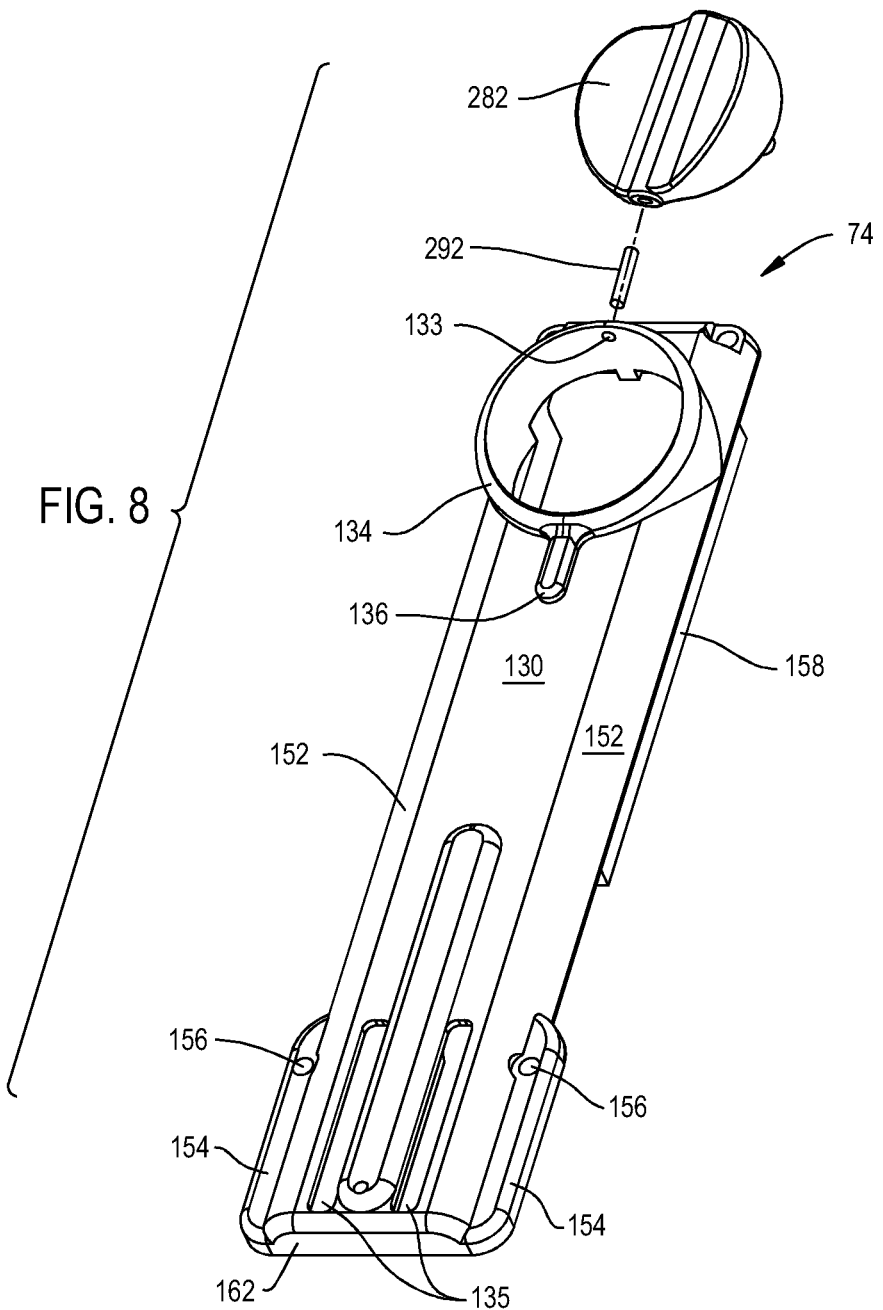
FIG. 8 a perspective view of the handpiece lid.

A cylindrical pin 292, seen in FIG. 8, pivotally connects button 282 to handpiece lid 74. Pin 292 extends through lid opening 133, button bore 286 and lid bore 141. Owing to the relative dimensioning of the lid 74 and the button 282, the button is able to, within lid through hole 132, pivot around pin 292.

Figure 24:
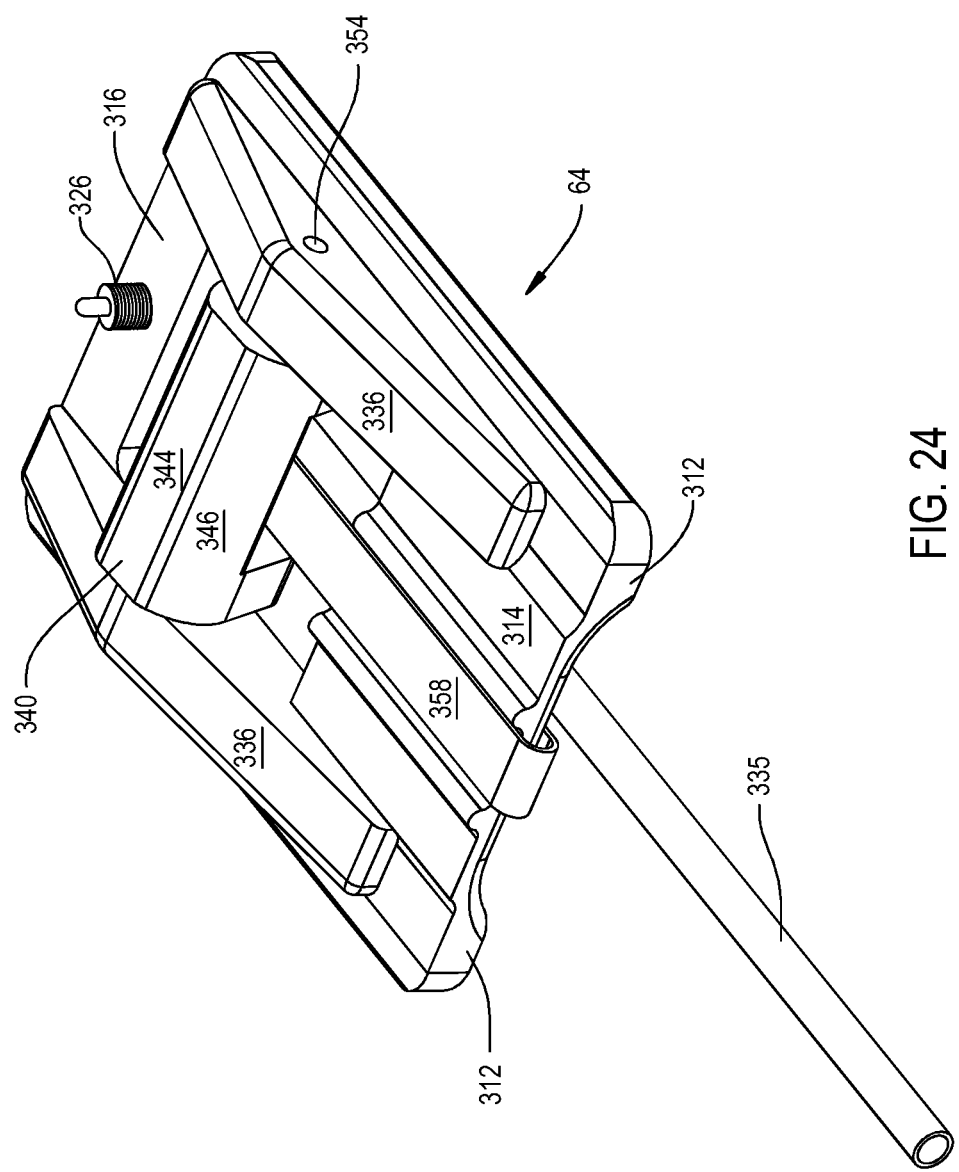
FIG. 24 is a perspective view of the proximal slide and the components attached to the slide.

The proximal slide 64, now described by reference to FIGS. 24-26, is formed from the same material from which distal slide 62 is formed. Proximal slide 64 is shaped to have a pair of laterally spaced feet 312. The slide 64 is shaped so that the lateral distance across the slide, the lateral distance between the outer edges of feet 312, is approximately 0.25 to 0.5 mm less that the width across the opposed inwardly directed faces of the base side panels 80. Each foot 312 has a width that is approximately 1 mm wider than the width across a base rib 106.

Feet 312 are connected together by webs 314 and 316. Web 314, the distal of the two webs, extends proximal rearward from the distal ends of feet 312. Slide 64 is shaped so that web 314 is slightly elevated relative to feet 312. Web 314 is generally planar in shape. There are transition surfaces, not identified, along the sides of the web 314 where the web extends above the feet 312. The outwardly directed surface of the web 314 is formed to have two parallel ribs 318 that extend the length of the web. Ribs 318 are symmetrically spaced apart from each other along the longitudinal center of the slide 64.

The more proximal of the two webs, web 316, is spaced longitudinally from the proximal end of web 314. Web 316 extends forward from the proximal end of feet 312. The outwardly directed surface of web 316 is coplanar with the outwardly directed surface of the feet 312. Web 316 is formed with a rib 320 that extends laterally across the slide 64. Rib 320 is located between feet 312. A threaded bore 324 extends inwardly from the outwardly directed surface of rib 320. A spring biased pin detent 326, seen only in FIG. 24, is fitted in bore 324. The pin integral with detent 326 is dimensioned to seat in the bore 140 internal to lid rib 142.

The proximal slide 64 is further shaped to have a shoe 330 that extends below the rib 320. The shoe 330 extends across rib 320; along an axis aligned with the longitudinal axis of slide 64. Shoe 330 has a generally trapezoidal shape, the end of the shoe spaced distal to the rib 320 is shorter in length than the portion of the shoe adjacent the rib. Shoe 330 is centered along the longitudinal axis of the slide 64. The slide 64 is formed so that there is a through bore 332 in the shoe. The through bore 332 is positioned so that, when the shoe is seated in base 72, the bore 332 is coaxial with base bore 112. A toe 334 extends forward from shoe 330. Toe 334 is an arcuately shaped member that extends approximately 180° around and forward of the distally directed opening into bore 332. Toe 334, in addition to extending forward of shoe 326 extends forward of rib 320.

A tube 335, seen only in FIG. 24, extends forward from proximal slide shoe 330. Tube 335 is formed from metal such as stainless steel. The proximal end of tube 335 is adhesive or compression secured in shoe bore 332. Tube 335 extends forward from the shoe 330 so as to extend below and forward of slide distal web 314.

Proximal slide 64 has two pylons 336. Each pylon 336 is generally in the shape of a triangle. Each pylon 336 extends upwardly from a separate and outwardly directed surface of a separate one of the slide feet 312. Below the apex of each pylon 336, each pylon is formed to have a bore 338 that extends widthwise through the pylon. Bores 338 are thus coaxial. It should further be understood that bores 338 are located along an axis that is located over the void space in the slide 64 between webs 314 and 316.

A cam latch 340, seen in FIGS. 24 and 27, is rotatably mounted between the distal slide pylons 336. The cam latch 340 is formed from the same material from which the distal slide 64 is formed. Cam latch 340 has a beam 342 shaped to have a number of curved and straight surfaces. Specifically, beam 342 has a top surface 344 that is generally planar. Curved side surfaces 346 extend away from the opposed distally and proximally directed sides of the top surface 344. Overall, the top and side surfaces 344 and 346, respectively, of the beam are shaped so that the beam can seat in the void space between lid rib face 144 and lid rib face 148. Side surfaces 346 are convex curvature and are further shaped so as to be able to seat against rib faces 144 and 148. Opposite to and parallel with top surface 344, beam 342 is shaped to have a planar bottom surface 348. The beam bottom surface 348 has a width, the length across the rib, the dimension parallel to the longitudinal axis of the distal slide 64 that is greater than comparable width across the beam top surface 344.

Cam latch 340 is further formed so that there is a tab 350 at each end of the latch. Tabs 350 are integral with beam 342. Each tab 350 is the form of a triangle that extends downwardly from an end of the beam bottom surface 348. It should be appreciated that owing to the presence of tabs 350, the length of the beam bottom surface 348, the dimension perpendicular to the longitudinal axis of the slide 64 is less than that of the length of the beam top surface 344.

A bore 352 extends side-to-side through the cam latch 340; through the beam 342 and the opposed tabs 350. Bore 352 is centered on an axis that is further from the beam top surface 344 than the bottom surface 348. A pin 354, the end of which is seen in FIG. 24, rotatably holds the cam latch 340 to the slide pylons 336. Pin 354 is seated in cam latch bore 352. The opposed ends of the pin 354 extend out away from the opposed exposed faces of latch tabs 350. Each exposed end of pin 354 is seated in one of the pylon bores 338.

A leaf spring 358, seen in FIG. 24 is mounted to distal web 314. The spring 358 is formed from metal such as stainless spring steel. Spring 358 is generally in the form of a U-shaped clip though the sections of the spring are of unequal length. The spring 358 is fitted around the slide web 314 so that the U-shaped bend projects rearward from the distally facing front end of the web. The shorter of the two sections of the spring is disposed over the undersurface of the web 314. The longer of the two sections of the spring 358 extends over the top surface of the web 314 between ribs 318. The spring 358 is shaped so that the shorter of the two sections does not extend rearwardly beyond web 314. The longer of the two sections of spring 358 extends beyond the web to a location rearward of where bores 338 extend through pylons 336. When the proximal slide is assembled, the longer of the two sections of spring 358 bears against latch bottom surface 348. The abutment of the spring 358 against the cam latch 340 inhibits rotation of the latch.

When handpiece 50 is assembled, the proximal slide 64 is mounted in the base 72 so that the slide feet 312 rest on base ribs 106. The proximal slide 64 is positioned longitudinally in the base 72 so that when the lid 74 is in place, the cam latch 340 is disposed between lid ribs 142 and 146. More particularly, the latch 340 is positioned so that one of the surfaces 346 is located adjacent face 144 of rib 142 and the opposed surface 346 is adjacent face 148 of rib 146.

Figure 28:
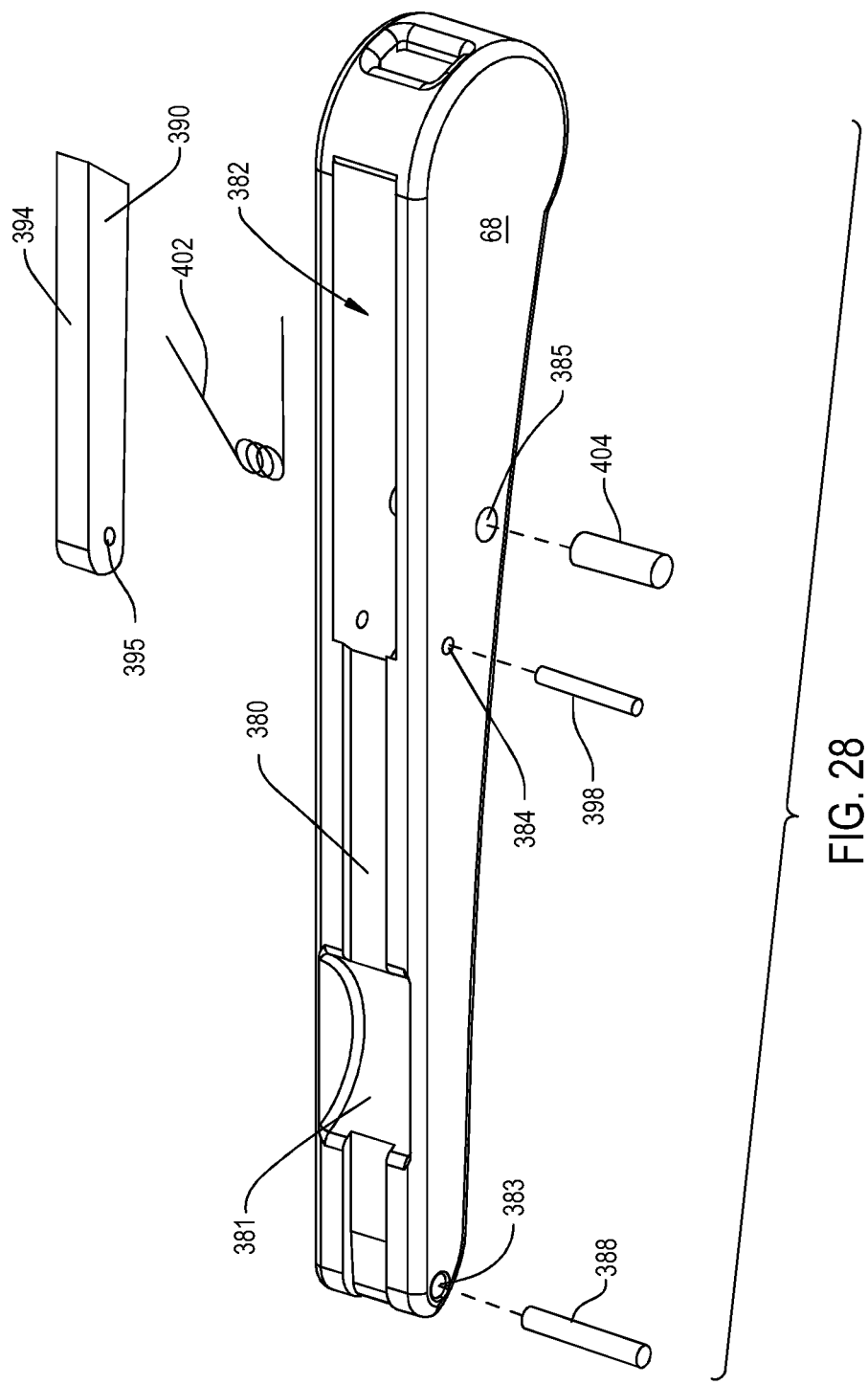
FIG. 28 is an exploded view of the handpiece ratchet and the components attached to the ratchet.

Ratchet 68, now described by reference to FIGS. 28 and 29, is formed from the same material from which the handpiece base 72 and lid 74 are formed. The ratchet 68 is an elongated member. The ratchet 68 has a width that allows the ratchet to, with clearance, extend into slot distal section 86 in the base bottom panel 78. The length of the ratchet 68 is such that at least the top portion of the ratchet is able to seat in the slot distal section 86. Ratchet 68 is further formed so as to have a top-to-bottom height that generally increases proximally from the distal end of the ratchet. Not identified are the bumps on the downwardly directed surface of the ratchet 68. These bumps function as finger holds.

The ratchet 68 is further formed so as to have along the upwardly directed face, the face directed towards handpiece base 72, a groove 380 with a rectangular cross sectional profile. Groove 380 has a width wider than the width across the rack 212 that extends along the underside of the distal slide 62. This dimensioning allows the rack to move within the groove. Groove 380 extends approximately along 60% of the length of the ratchet 68. A cavity 381 extends inwardly from the upwardly directed face of the ratchet 68. Cavity 381 is located proximal to the distal end of the ratchet and intersects groove 380. In cross section, along a vertical plane through which the ratchet longitudinal axis extends, cavity 381 is seen to have a curved profile. More particularly, cavity 381 is shaped to accommodate the feet 272 and toes 280 of steering blocks 172. Proximal to groove 380, the ratchet 68 is formed to have a void space 382. Void space 382 is contiguous with the proximal end of groove 380. Void space is both wider across than groove 380 and extends deeper into the ratchet 68 than groove 380.

Three bores extend laterally through ratchet 68. A first bore, bore 383, extends through the ratchet 68 immediately rearward of the distal end of the ratchet. The second bore, bore 384, extends through the ratchet so as to intersect the distal portion of void space 382. The third bore, bore 385, is located slightly rearwardly of and below bore 384. Bore 385, like bore 384, extends through ratchet void space 382. The ratchet 68 is further formed to have in an opening 386 that extends forward from the proximally directed face of the ratchet. Opening 386 opens into void space 382.

The distal end of the ratchet 68 is seated in the distal end of handpiece slot distal section 86. The distal end of ratchet 68 is thus located between the two sections of rib 90. A pin 388, seen in FIG. 28, extends through the bore 91 internal to the handpiece 54 and the coaxial ratchet bore 383. Pin 388 pivotally holds the ratchet 68 to the handpiece base 72.

A pawl 390, seen in FIGS. 28 and 30, is pivotally mounted to the ratchet 68. The pawl 390 is generally in the shape of a bar. The pawl 390 has a length, width and height that allow the arm to seat entirely within the ratchet void space 382. Pawl 390 is shaped to have a rearwardly directed face 392 that angles both downward and forwardly away from the adjacent upwardly directed face 394. Immediately proximal to the distal end of the pawl 390, a bore 395 extends laterally across the pawl. The pawl 390 is further formed so as to have a groove 396 in the downwardly directed face of the arm, the face directed away from the handpiece base 72.

The pawl 390 is seated in ratchet void space 382. A pin 398 pivotally holds the pawl 390 in the distal end of the ratchet void space 382. Pin 398 extends through ratchet bore 385 and arm bore 395.

A torsion spring 402 normally urges the pawl 390 away from ratchet 68. A pin 404 holds the center coil section of the torsion spring 402 in the ratchet void space 382. The opposed ends of pin 404 seat in ratchet bore 385. Collectively, the spring 402 and pin 404 are located so that the coil is located above the base of the void space slightly rearward of the interior surface of the ratchet 68 that defines the distal end of the void space. One arm of the spring 402 bears against the interior wall of the ratchet 68 that defines the base of the void space 382. The opposed arm of the spring 402 seats in pawl groove 396.

A release button 408, seen in FIG. 31, is slidably mounted in base slot proximal section 88. Button 408 has a plate 410. Extending forward and coplanar with plate 410 is a head 412 and two arms 414. Head 412 is dimensioned to slidably fit in ratchet opening 386. Arms 414 are located on the opposed sides of head 412. Arms 414 are spaced apart a distance slightly greater than the width across ratchet 68.

A fin 416 extends perpendicularly upward from plate 410. Fin 416 has a width that allows the pin to slide in the base slot proximal section 88. A rectangularly shaped cap 418 is connected to and extends outwardly away from the top of fin 416. Cap 418 has a width across greater than the width across base slot proximal section 88. Button 408 is further formed so that the gap between plate 410 and cap 418 is slightly greater than the wall thickness of the handpiece bottom panel 78. A beam 420 extends proximally from cap 418. A tab 422 extends downwardly from beam 420, towards the underlying plate 410. Tab 422 is dimensioned to seat in either of the divots 96 that extend inwardly from the inner surface of the base bottom panel 78.

When handpiece 50 is assembled, release button 408 is slidably mounted to the base bottom panel 78 so that the plate 410, head 412 and arms 414 are located adjacent the panel outer surface, fin 416 extends through slot proximal section 88 and cap 418 extends over the panel inner surface. Leg 420 and toe 422 extend over the inner surface of the base bottom panel 78.

IV. Core and Sheath

The system core 54, seen best in FIGS. 32 and 33, includes two parallel sections of wire 430. In one version of the invention, wire is formed from stainless steel and has a diameter of 0.2 mm. This wire, while flexible, can withstand some axial loading. Wire 430 is bent so as to have a U-shape and to define the two parallel sections of the wire.

The most distal section of the wire, the section of the wire that includes the actual U-shape bend, is encased in a plastic head 432. Head 432, seen in FIG. 34, is formed from a plastic such as nylon. The head 432 is formed to have a base 434. Base 434 has an oval cross sectional shape. Forward of base 434, head 432 has a nose 436. Nose 436 has an oval cross sectional shape with a length and width greater than the length and width of the base 434. The head is formed to have a U-shaped bore 438. The bore 438 has an opening on one side of the proximally directed face of base 434 and extends into nose 436. Head 432 is further shaped so that bore 438 curves around to have a second opening in the opposed side proximally directed face of base 434. Bore 438 is dimensioned to receive the core-forming wire 430. Head 432 may be molded in place over wire 430. The molding of the head 432 over wire 430 defines bore 438.

Figure 2A:
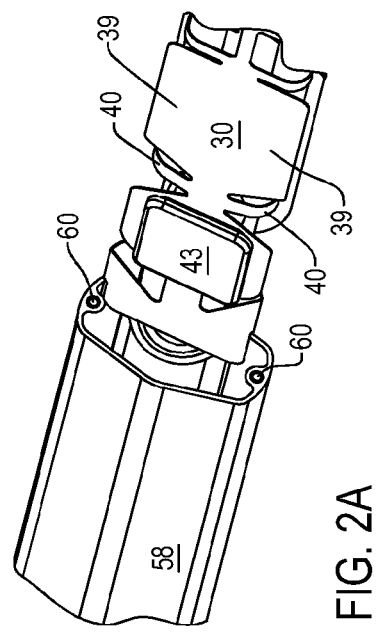
FIG. 2A is an enlargement of a portion of FIG. 2.

Core 54 further includes a pair of sleeves 440. Each sleeve 440 is disposed over a section of wire 430 that extends proximally from head 432. In one version of the invention, each sleeve 440 is formed from a flexible polymer such as LDPE and has an outer diameter of approximately 1.5 mm. As seen in FIGS. 2 and 2A, wire 430 and sleeves 440 are shaped so that when the array 30 is wrapped around the core 54 each bridge 38 is disposed over or under the longitudinal plane that extends between and parallel with sleeves 440. Each pair of electrode-supporting tabs 60 at least partially subtends the sleeves 440. When the array 30 is so wrapped, the beams 40 conform around the outer surfaces of the sleeves 440. Sleeves 440 are dimensioned such that, when the array beams 40 are so wrapped, the beams are not bent to the extent that the beams undergo plastic deformation.

The sleeves 440 extend proximally, rearwardly, along the sections of wire 430 a distance approximately equal to the length of the array 30 system 50 is intended to introduce and deploy. Core 54 can be considered the sleeve-encased sections of wire 430 and head 432.

Figure 35:
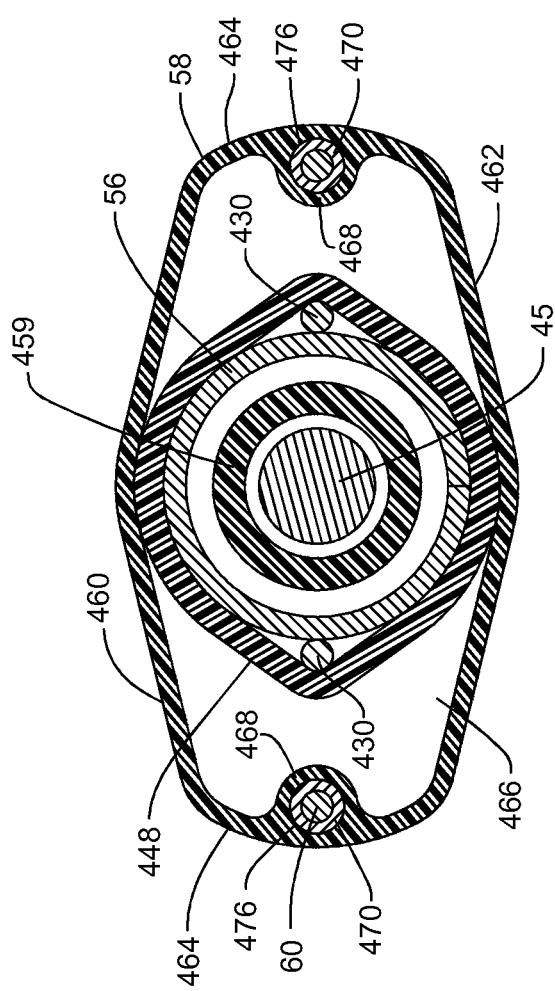
FIG. 35 is a cross sectional view through the sheath showing the core forming wires and spring encased therein.

Wire sections 430 extend rearward of core 54 and through the sheath 58 as seen best in FIGS. 33 and 35. Rearward of the core 54, wires 430 are disposed against spring 56. Spring 56 is a coil spring formed from stainless steel. Given the helical shape of the spring 56, it should be appreciated that a lumen, not identified, extends axially through the spring. The spring 56 is further formed so that the diameter of this spring lumen is slightly greater than the outer diameter of the cable 45 that extends proximally from the array 30. In one version of the invention, the diameter of the spring lumen is approximately 1 to 2 mm greater than the diameter of the array cable 45.

The opposed sections of wire 430 are disposed against diametrically opposed portions of the outer surface of spring 56. In the illustrated version of the invention, the spacing between the core 54-forming wire sections are spaced slightly closer apart from each other than more proximal portions of the section of wire 430 that are disposed against spring 56. Accordingly, immediately distal to the front end of the spring 56, each section of wire 430 includes a bend 446. Each bend 446 is the transition of the portion of the wire section that form the core 54 and the portion of the wire section that abuts spring 56.

A flexible tube 448 is disposed over spring 56 and the overlying wires 430. Tube 448 is a formed from a heat shrinkable material such as PTFE. The tube 448 when heat shrunk, has a wall thickness of approximately 0.05 mm. As a consequence of the heat shrinking of tube 448 over the sections of wire 430 and the spring 56, the wire sections are held against the spring 56 by the tube.

The spring 46-wire 430-tube 448 assembly extends proximally through the housing nose bore 126. This assembly seats in bore collectively formed by distal slide groove 180 and plate groove 248. The proximal end of this the wire 430-spring 56-tube 448 assembly is disposed in the tube 335 integral with proximal slide 64. More particularly, the wire 430-spring 394-tube 448 assembly is solder secured in the open end distal end of tube 335.

Disposed inside of, and extending rearwardly with, spring 56 is the array cable 45. In FIG. 35 a biocompatible polymer sleeve 459 is shown as being disposed around the array cable 45. Sleeve 459 is also shown as having an inner diameter greater than the outer diameter of the cable 45. In practice, the sleeve 459 may be integral with and tightly surround the wires internal to cable 45. It should be understood that the cable 45, including the surrounding insulating sleeve, are dimensioned relative to the lumen defined by spring 58 so that the cable 45 and spring 56 are able to move freely relative to each other.

Sheath 58 of system 50 of this invention is formed from a biocompatible polymer such as nylon. As seen best in FIGS. 33 and 35, sheath 58 has a generally oval cross sectional shape. More particularly, the sheath is shaped to have parallel top and bottom panels 460 and 462, respectively. Panels 460 and 462 each have a thickness of approximately 0.75 to 1.25 mm. Side panels 464 extend between the top and bottom panels 460 and 462, respectively. Each side panel 464 curves outwardly relative to the edges of the adjacent top and bottom panels 460 and 462. Collectively, panels 460, 462 and 464 define a lumen 466 that extends axially through the sheath. Sheath 58 is further formed so that each side panel 464 has an inwardly extending rib 468. Each rib 468 projects inwardly from the side panel 464 with which the rib is associated so that ribs are directed toward each other. A bore 470 extends through each rib 466. Bores 470 thus extend longitudinally through the opposed sides of sheath 58. In FIG. 35, sections of the steering cable 60 are shown in the bores 470.

Figure 36:
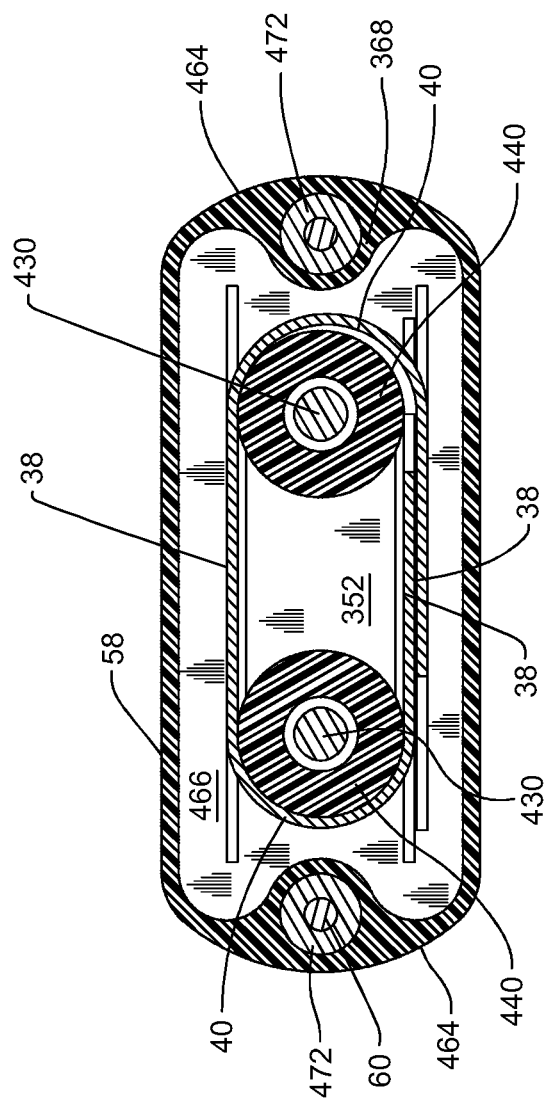
FIG. 36 is a cross sectional view through a distal portion of the sheath showing how the electrode array is folded/bent around the core and the array and core are both encased in the sheath.

Sheath 58 is shaped so that the minor axis in lumen 466, the distance between the adjacent inner faces of top panel 460 and bottom panel 462 is slightly greater than the width across the array 30 when folded over the core 54. In some versions of the invention, this lumen width is approximately 0.5 mm greater than the distance between the outer surface of bridge 38 and the outer surface of the outer of the two folded under bridges 38. This lumen width is such that, when the array is disposed in the sheath 314, the lumen prevents the energy stored within the folded superelastic beams of the carrier from unfolding the array 40. In FIG. 36, for ease of illustration, gaps are shown between the outer surface of the folded over bridges 38 and the adjacent inner surface of sheath top and bottom panels 460 and 462, respectively. In reality, the carrier is unfolded to the maximum extent allowed by the sheath 314. Sheath 314 is outwardly stretched as a consequence of this unfolding of the carrier. The sheath 314, as seen in FIG. 36, stretches outwardly to accommodate spring, wire and tube assembly. System 50 is constructed so that sheath 58 extends proximally rearward from the head 432 from which wires 430 extend.

Each steering cable 60 is disposed in a separate one of the sheath bores 470. Each cable 60 is formed from stainless steel and has a diameter of approximately 0.15 mm. Cables 60 extend out from the proximal end of sheath 314 and are connected to the steering assembly. Each steering cable 60 extends through the associated bore 470 to the distal end of the bore.

An anchor 472 holds the distal end of each steering cable 60 in the distal end of the associated sheath bore 470. In one version of the invention, the anchor 472 comprises a strand of wire wrapped around the distal end of the cable 60. This wire may be a preformed coil spring. Solder secures the spring to the steering cable 60. Each anchor 472, as depicted in FIG. 36 has an outer diameter larger than that of the steering cable 60. In FIG. 36 for ease of illustration the anchors 472 are seen simply as large diameter sleeves disposed over the ends of the cables 60 with which the anchors are integral. The outer diameter of each anchor 472 is, relative to the sheath bore 470 is sufficiently large so that the portion of the sleeve that defines the bore holds the anchor in place. In some versions of the invention, an adhesive, such as epoxy, is further used to hold each anchor 472 in the distal end of the associated sheath bore 470.

A sleeve 476 extends longitudinally over each cable 60. Sleeves 476 are formed from stainless steel or other material that is less flexible than the encased steering cables 60. Collectively, sheath 58, cables 60 and sleeves 476 are constructed so that the sleeve-encased cables 60 can seat in sheath bores 470. While not apparent in the drawings, in many versions of the invention, the components forming system 50 are constructed so that there is clearance between the outer surface of each steering cable 60 and the adjacent inner wall of the surrounding sleeve 476. This clearance may be 0.05 mm. This clearance facilitates the movement of the cable 60 in the sleeve. There may also a clearance between the outer surface of the sleeve 476 and the adjacent internal wall of the sheath 58 that defines the bore 470 in which the sleeve is seated. This clearance facilitates the seating of the sleeve 476 in the bore. In some versions of the invention, the outer diameter of each sleeve 476 is 0.05 mm smaller relative to the sheath bore 470 in which the sleeve 476 and associated cable 60 is seated.

The distal end of each sleeve 476 is located approximately 1 cm rearward of the distal end of the adjacent tube-encased spring 56. The proximal ends of the sleeves 476 are essentially adjacent the proximal end of the sheath 56 in which the sleeves are encased.

Figures 37, 38:
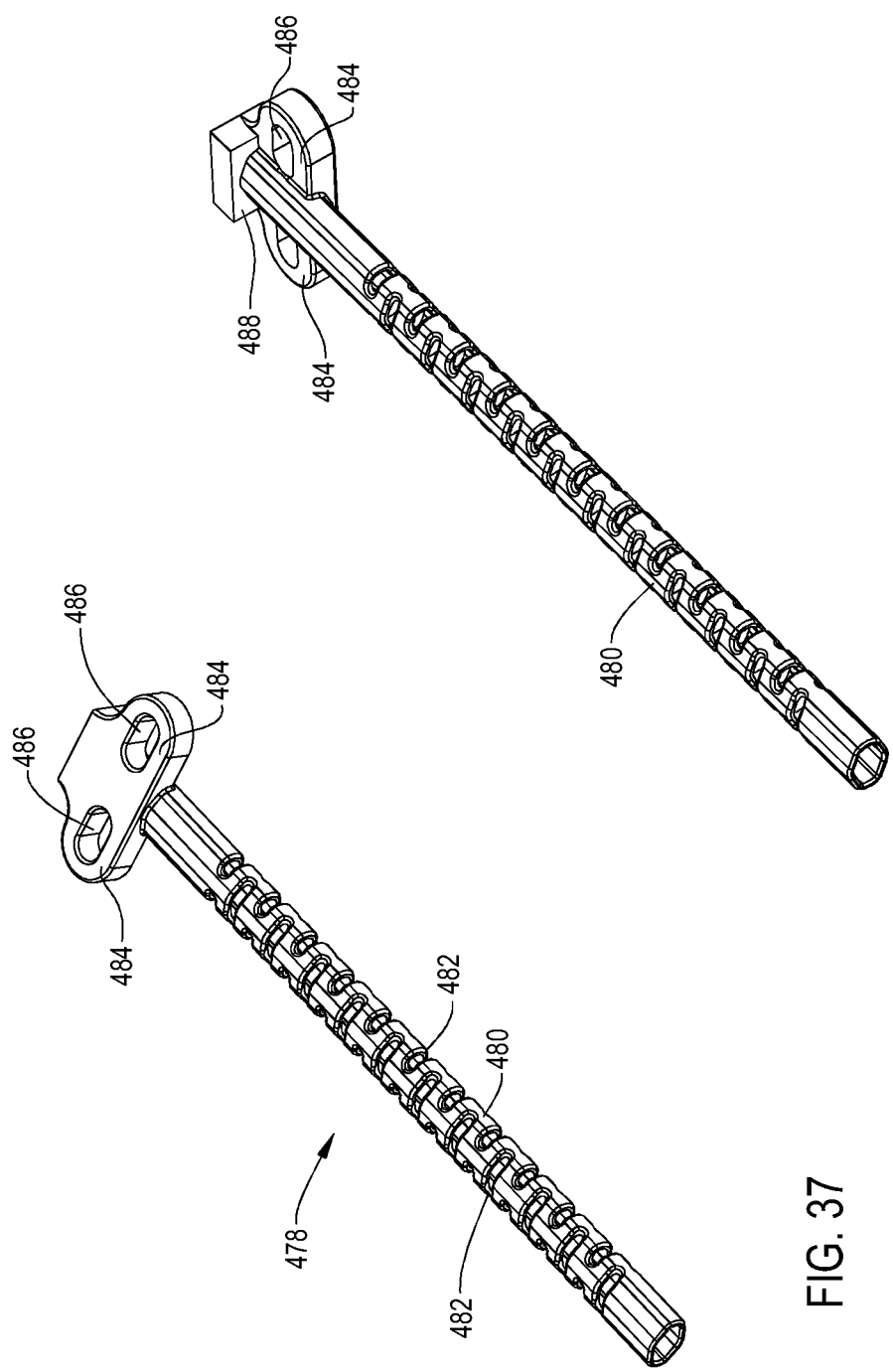
FIG. 37 is a perspective view of the top of the strain relief.
FIG. 38 is a perspective view of the bottom of the strain relief.

Sheath 58, including the components encased therein, extend proximally through the handpiece nose bore 126. A strain relief 478 is overmolded over the proximalmost 8 to 15 cm of the sheath 58, the portion of the sheath that extends through the housing nose bore 60. The strain relief 478 is formed from a thermoplastic such as nylon. Strain relief 478, now described by reference to FIGS. 37 and 38, has a tube like stem 480. Stem 480 is the portion of the strain relief 478 overmolded over the proximal end section of sheath 58. The stem 480 is shaped to define a number of notches 482 that extend inwardly from its outer surface. The notches 482 are in planes that are perpendicular to the longitudinal axis of the stem 480. The notches 482 reduce the stiffness, increase the flexibility, of the stem 480. In the illustrated version of the invention, the strain relief is formed so that the most proximal portion of the stem, a portion having a length of approximately 1 cm, is notch free. Stem 480 is further formed so that the proximal section can seat in indentation 178 formed in the distal slide 62.

Also part of the strain relief 478, two ears 484 are formed integrally with stem 480. Ears 484 extend laterally outwardly from the top portion of the proximal end of the step. Here, the stem "top portion" is understood to be the portion of the stem directed away from the proximal slide 62. The strain relief 478 is formed so that that the opposed inner and outer surfaces of ears 484 are generally planar and parallel. Each ear 484 is formed with an oval shaped opening 486. The strain relief 478 is formed so that the major axes of openings 486 are collinear. A collar 488, also part of strain relief 478, extends between over the proximal end of stem 480 so as to extend between ears 484. The bottom and side surfaces of collar 488 are rectangular in shape.

Figure 39:
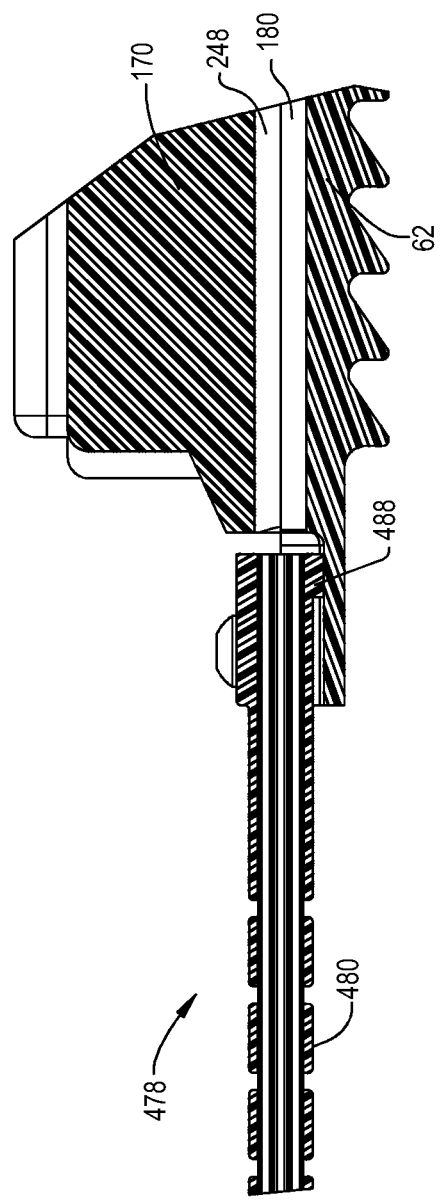
FIG. 39 is a cross sectional view depicting how the strain relieve is connected to the distal slide.

Strain relief stem 480, like the enclosed proximal end portion of the sheath 58, extends through housing nose bore 126. The strain relief ears 484 are disposed over the distal slide 62 so that the proximal end of the stem 480 and collar 488 are disposed in slide indentation 178. More particularly, the components of system 50 are constructed so that strain relief collar 488 is closely slip-fitted into the wide width proximal portion of indentation 178 as seen in FIG. 39. Strain relief ears 484 are positioned over the slide so that each opening 486 its disposed head openings 488 are in registration with the distalmost slide bores 216. Threaded fasteners 490 that extend through the strain relief openings 488 into the slide bores 216 hold the strain relief to the distal slide. Since sheath 58 is integral with the strain relief 478, fasteners 490, by extension hold the sheath 58 to the slide.

When handpiece 50 is assembled, spring 56 and steering cables 60 extend proximally rearward out of sheath 58 and strain relief 478. As discussed above, tube 335 holds spring 56 to proximal slide 64. Steering cables 60 also extend out of the proximal end of the sheath. As discussed above, each steering cable 60 passes through the grooves formed on the distal slide 62, is threaded through one of the steering blocks 172 and is tied to one of the tensioners 168.

V. Stimulating Guidewire and Introducer Sleeve

System 30 of this invention also includes a stimulating guidewire 510 (FIG. 40) and an introducer 550 (FIG. 44). At the start of the array implantation procedure, guidewire 510 is used to generally identify the target tissue over which the implantable medical device, array 30, should be deployed. Once this location is identified, introducer 550 is slip fitted at least partially over the guidewire 510. Introducer 550 is then advanced a short distance into the potential space into which the sheath encased electrode array is subsequently introduced. Guidewire 510 is then retracted out of the introducer 550. A lumen through introducer 550 functions as the guide path through which the sheath-encased electrode array 30 is percutaneously inserted into the patient.

Figure 40:
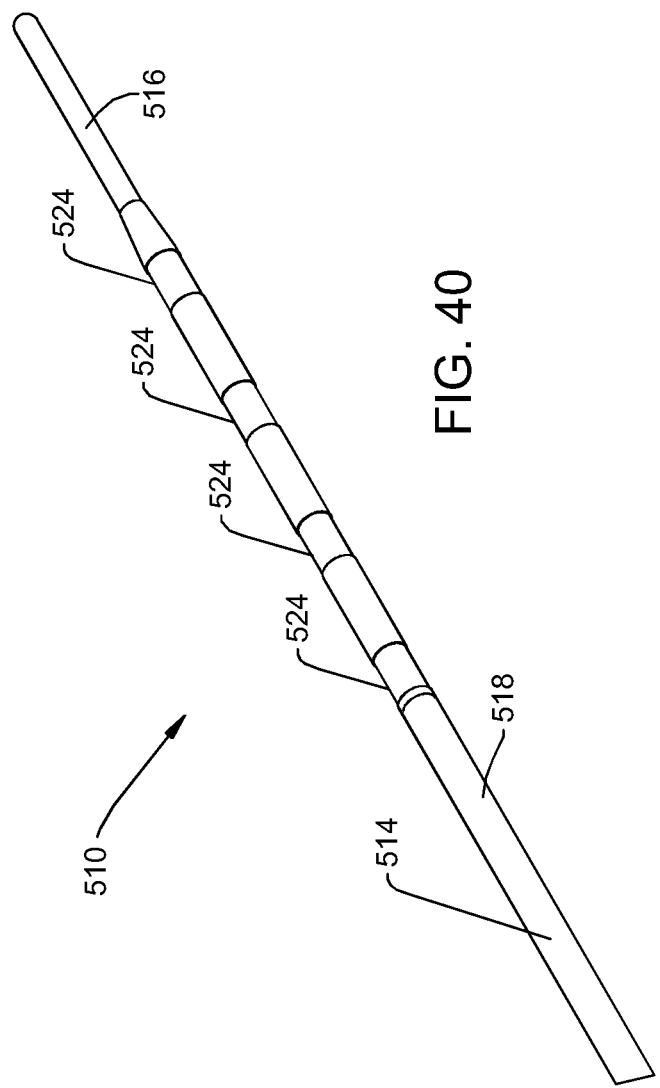
FIG. 40 is a perspective view of a stimulating guidewire of this invention when a straight stylet is disposed in the guidewire.
Figure 41:
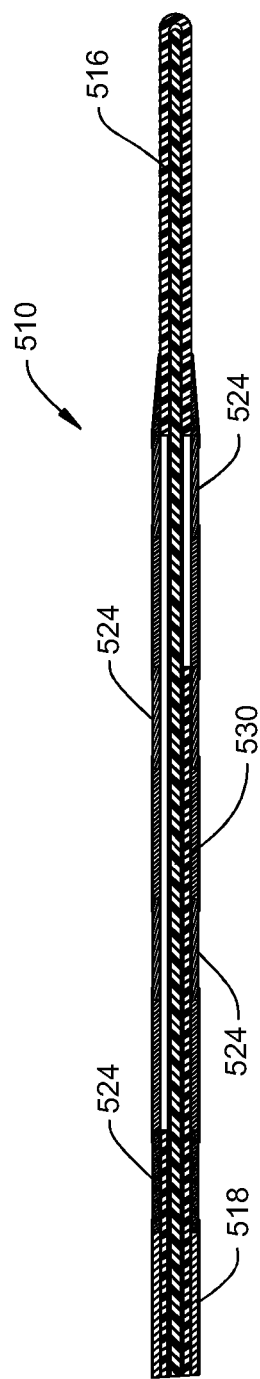
FIG. 41 is a cross sectional view of a stimulating guidewire when viewed along a longitudinally extending plane.
Figure 42:
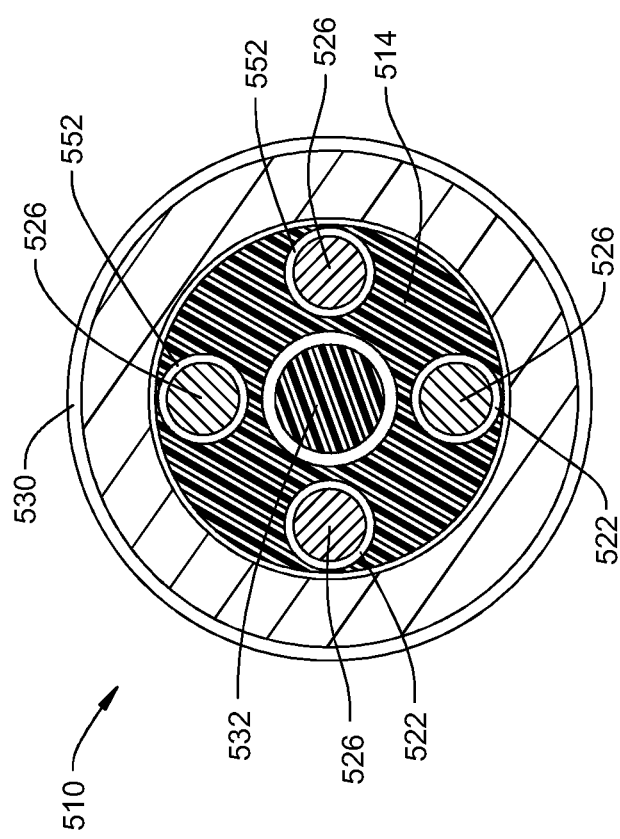
FIG. 42 is a cross sectional view of a stimulating guidewire when viewed along a plane that extends laterally through the guidewire.

The guidewire 510, now described by reference to FIGS. 40-42, includes a shell 514 formed from a flexible biocompatible thermoplastic. Shell 514 is generally in the form of an elongated tube. In many versions of the invention, the shell has a maximum outer diameter of 3.0 mm. This facilitates the insertion of the shell in the lumen of a needle. The shell 514 is, however, further formed so as to have a closed distal end. The shell 514 is shaped to have a nose 516, which is the most distal portion of the guidewire and a trunk 518 that extends proximally from the nose. Shell trunk 518 has a diameter greater than that of shell nose 516. In one version of the invention, the shell nose 516 has an outer diameter of approximately 1.0 mm; shell trunk 518 has a diameter of approximately 1.5 mm. Not identified is the tapered transition section of the shell 514 between nose 516 and trunk 518. The shell 514 has a central bore 520 as well as a number of auxiliary bores 522. Bores 520 and 522 are closed end bores. Central bore 520 extends axially through the shell 514 and terminates at a location proximal to the distal end of the shell nose. Auxiliary bores 522 are equiangularly spaced apart from each other relative to the central longitudinal axis of the shell 514. The centers of bores 522 are equidistance from the center of bore 522. Also, while not illustrated in the drawings, the guidewire may be formed so that the auxiliary bores 522 extend helically through the shell 514. Guidewire 510 is formed so that the auxiliary bores 522 terminate at the distal end of the shell trunk 518. In the version of the version of the invention wherein the shell trunk 518 has an outer diameter of approximately 1.5 mm, central bore 520 has a diameter of approximately 0.4 mm; the auxiliary bores 522 have a diameter of 0.25 mm.

Four tube-like sleeves 524 formed from electrically conductive material are disposed over the shell trunk 518 so as to be, along the length of the guidewire 510, longitudinally spaced apart. Some versions of the guidewire 510 are constructed so that the inner diameters of the sleeves 524 have an inner diameter that is less than the outer diameter of the shell trunk 518. In versions of the invention wherein the outer diameter of the shell trunk 518 is approximately 1.5 mm, each sleeve 524 may have an inner diameter of approximately 1.25 mm and a wall thickness of 0.25 mm. Each sleeve 524 functions as an electrode through which current can be sourced to or sunk from the tissue against which the guidewire 510 is disposed.

Current is sourced to or sunk from each guidewire sleeve 524 by a specific conductor 526 that extends through the shell trunk 518. In the illustrated version of the invention there are four sleeves 524. Therefore, there are four conductors 526. Each conductor 526 is disposed in a separate one of the shell auxiliary bores 522.

Guidewire 510 is further constructed so that a number of sections of heat shrink tubing 530 are disposed over the shell trunk 518. The tubing forming the heat shrink tubing is selected so that, as a result of the tube sections 530 compressing around the shell trunk 518 the trunk sections over which the tube sections 530 are disposed have a greater outer diameter than the trunk sections over which the conductive sleeves 524 are disposed.

In some methods of manufacturing the guidewire 510 of system 50 of this invention, slits or other openings (not illustrated) are formed in the shell trunk 518. Each slit/opening extends into a separate one of the shell auxiliary bores 522. More specifically, each slit/opening is formed in a section of the shell trunk 522 over which a sleeve 524 is to be located. Once the slits/openings are formed, the sleeves 524 are disposed over shell trunk 518. Owing to the relative dimensions of the shell trunk 518 and the sleeves 524, and the flexible nature of the material forming the shell 514, the sleeves and conductors 526 essentially press through the slits/openings to abut. This shell-to-conductor contact establishes the electrical connection between these two components. In some versions of the invention, the shell-to-conductor contact can be further established by welding or a solder joint. In some method of manufacture, the welding causes localized ruptures in the shell trunk through which the conductor-to-sleeve connections are formed. This eliminates the need to form slits in shell trunk 522.

In one method of manufacturing guidewire 510, a rigid rod is initially inserted in the shell center bore 520 to provide the shell with some rigidity. Conductors 526 are then threaded into the shell 514. The necessary slits are cut in the shell trunk 518. Sleeves 524 are then fit over the shell trunk. Once the sleeves are in place, a piece of unshrunk heat shrink tubing is fitted over the shell trunk. The tubing is then shrunk. The shrunk tube extends over the edges of sleeves 524 to hold the sleeves in place.

The proximal ends of the conductors 526 extend out of the proximal end of the guidewire shell 514. Conductors 526 are connected to an external test module. This test module contains current sources, current sinks and components for measuring the voltages present at the sleeves 524. The structure of this test module and connections to it (both not illustrated) is not part of the present invention.

When the guidewire is prepared for use, a flexible stylet 532 is disposed in the shell central bore 520. The stylet 532, while having some degree of flexibility, is less flexible than the shell 514. In some versions of the invention, the stylet 532 is formed from Teflon coated stainless steel. If the central bore 520 has a diameter of approximately 0.4 mm, the stylet has a diameter of approximately 0.3 mm. Stylet 532 is fitted in the shell 514 so as to extend into the portion of the central bore 520 formed in the nose 516.

Figure 43:
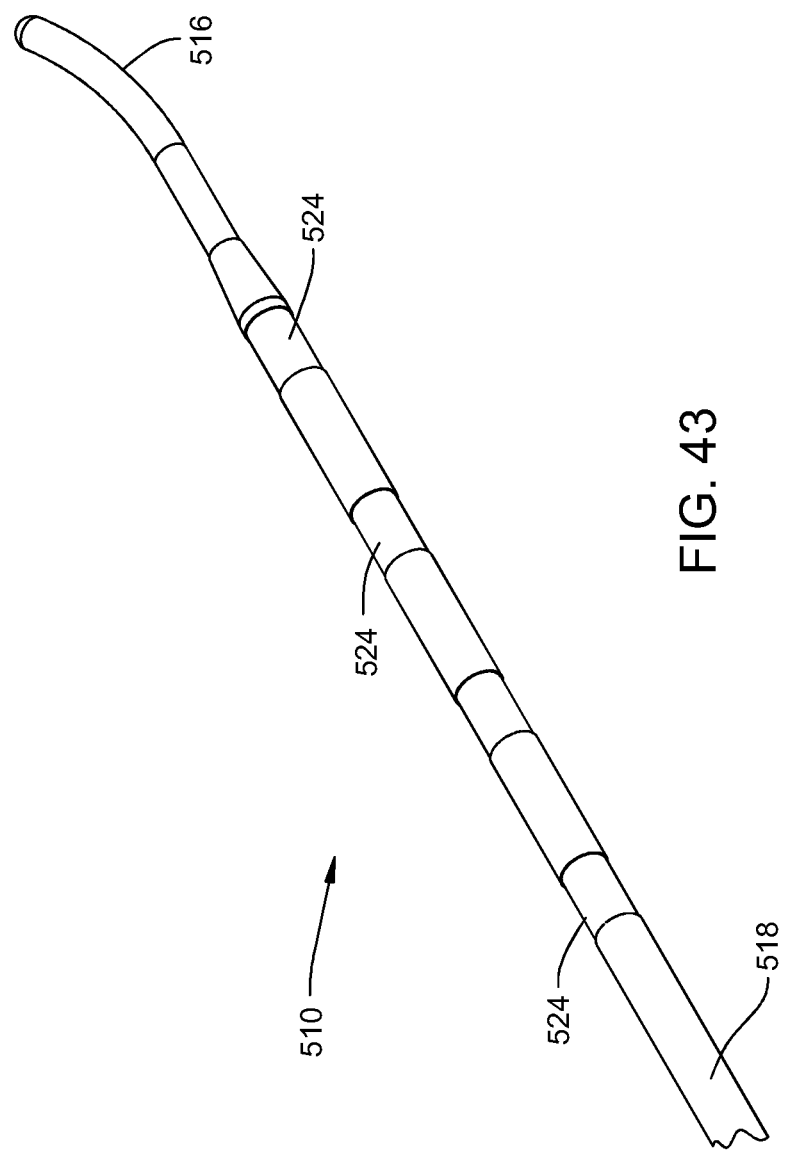
FIG. 43 is a perspective view of the guidewire when a stylet with a curved distal end is disposed in the guidewire shell.

The stylet 532 disposed in the shell 514 may be straight. With a stylet 532 so shaped, the guidewire 510 itself generally has a straight shape. Again it should be appreciated that, while the guidewire 510 is straight it is also flexible. Alternatively, the stylet 532 disposed in the guidewire shell 514 may have a distal end tip that is bent or curved near the nose. (Stylet not illustrated.) When this particular type of stylet 532 is fitted in the shell 514, the guidewire itself, as seen in FIG. 43, develops a curve along its longitudinal axis. It may be desirable to flex the guidewire 510 into the curved state when there are obstructions between where the guidewire is inserted into the patient and the location against where it is believed the electrode array 30 should be deployed. In these situations, curving the guidewire nose can make it easier to steer the guidewire around the obstructions.

Figure 45:
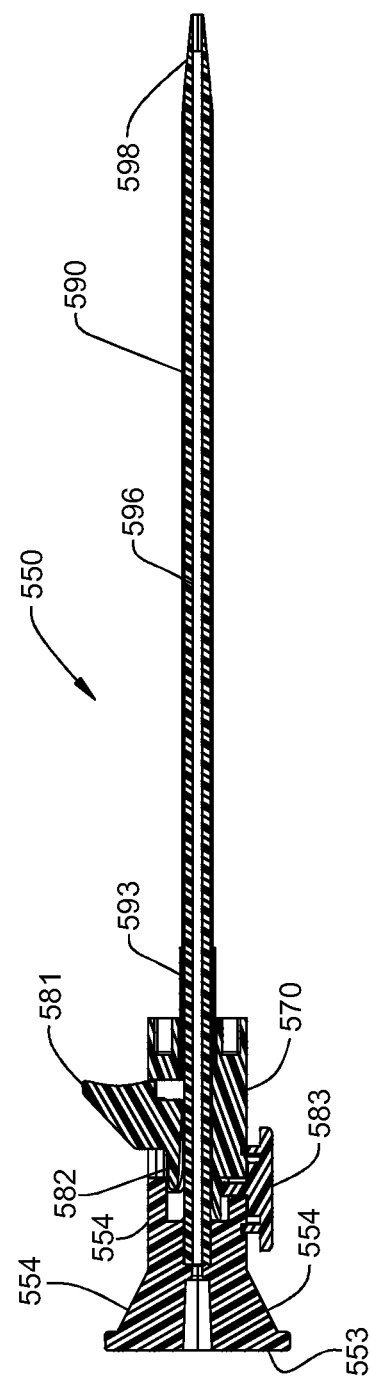
FIG. 45 is a cross sectional view of the introducer when viewed along a longitudinally extending plane.

The introducer 550 is now described by initial reference to FIGS. 44 and 45. At the most proximal end, the introducer 550 includes a dilator hub 552. A sleeve hub 570 is removably attached to and extends forward from the dilator hub 552. A tube like sleeve 590 is attached to and extends forward from the sleeve hub 570. A flexible dilator 596 is attached to and extends forward from the dilator hub 552. The dilator 596 extends through both the sleeve hub 570, the sleeve 590 and out forward from the distal end of the sleeve.

Figure 46:
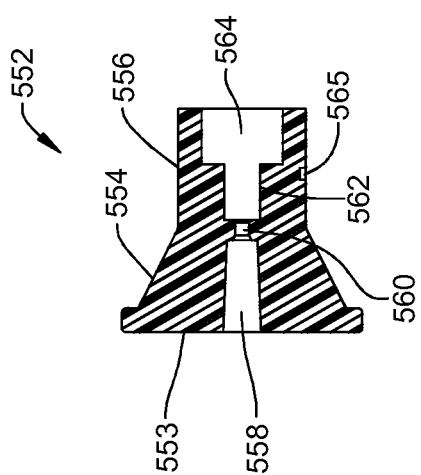
FIG. 46 is a cross sectional view of the dilator hub when viewed along a longitudinally extending axis.

The dilator hub 552, seen in FIGS. 44 and 46, is formed a single piece of thermoplastic such as a polycarbonate plastic. At the most proximal end, the dilator hub 552 has a base 553 that is generally oval shaped. A pedestal 554 extends distally forward from the base 553. In cross section, in a plane perpendicular to the longitudinal axis of the introducer 550, the pedestal 554 appears to have a shape of a rectangle with rounded corners. The dilator hub 552 is further shaped so that as the pedestal 554 extends distally forward the sides of the pedestal taper inward. In the illustrated version of the invention, dilator hub 552 is shaped so that the most distal portion of the pedestal 554 is stepped inwardly from the base 553. Immediately forward of the pedestal 554, the dilator hub 552 is shaped to have a head 556 that forms the most distal portion of the hub 552. Head 556 is in the shape of rectangular block with rounded corners.

As seen in FIG. 46, dilator hub 552 is further formed so as to have four concentric bores 558, 560, 562 and 564 that collectively form a through path that extends through the longitudinal center axis of the hub. Bore 558, the most proximal of the bores extends forward from the proximally directed face of hub base 553. Bore 558 extends through the base 553 and substantially through the pedestal 554. Bore 560 extends forward from the distal end of bore 558. Bore 560 has a diameter less than that of bore 558. The diameter of bore 560 is, however, slightly greater than that of the guidewire shell trunk 518. Bore 562 extends forward of bore 560. Bore 562 has a diameter approximately equal to that of bore 558. Bore 564, which extends forward of bore 562, opens in the front end of the dilator hub 552. Bore 564 has a diameter greater than that of bore 562. A groove 565, shown only in cross section in FIG. 46, extends partially around hub head 556. Groove 565 is in a plane perpendicular to the longitudinal axis through dilator hub head 556. Groove 565 is only in a portion of one face of head 556.

Figure 47:
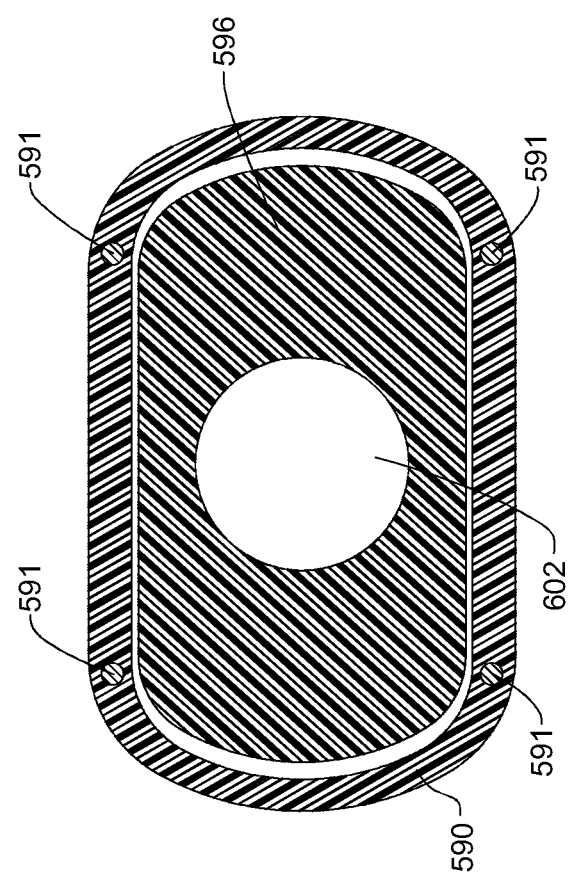
FIG. 47 is a cross sectional view of the introducer sleeve and dilator when viewed along a plane that extends laterally across the introducer.

The dilator 596 is an elongated flexible member formed from a plastic such as LDPE. As best seen in the cross sectional view of FIG. 47, in cross section, the dilator generally is oval shaped. The cross-section width and height of body of the dilator, the portion of the dilator disposed in sleeve 590, approximate the corresponding dimensions of sheath 58 when the array 30 is encased in the sheath. Forward of the body of the dilator, the dilator is formed to have a tip 598. Extending distally from the main body of the dilator 596, the cross sectional width and height of tip 598 decreases. Dilator 596 is further formed so as to have bore 602 that extends axially through the dilator along the whole of the length of the dilator. Bore 602 is dimensioned to receive the guidewire shell trunk 518. A marker 604, such as a material opaque to X-rays, may be disposed around the dilator tip 598.

The most proximal end of dilator 596 is mounted in dilator hub bore 560. An adhesive may be used to hold the dilator 588 to the hub 552.

Figure 48:
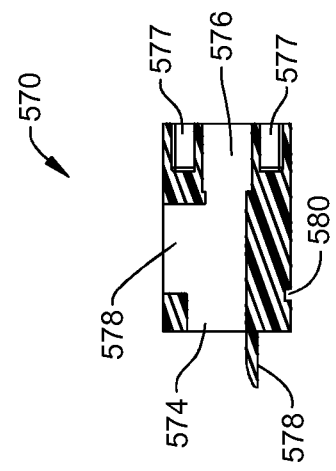
FIG. 48 is a cross sectional view of the introducer hub when viewed along a longitudinally extending plane.

The sleeve hub 570, now described by reference to FIGS. 44 and 48, is formed from the same material from which dilator hub 552 is formed. The sleeve hub 570 has a body with a cross sectional shape of a rectangle with rounded corners. The cross sectional width and height of the sleeve hub 570 are equal to the corresponding width and height of the proximal adjacent dilator hub head 556.

Two contiguous bores 574 and 576 form a longitudinal through path through the sleeve hub 570. Both bores 574 and 576 are centered on the longitudinal axis of the hub 570 and are oval in cross sectional shape. More particularly, both bores 574 and 576 are dimensioned to receive the dilator 596. A first one of the bores, bore 574, extends distally forward from the proximal end of the hub body 574. The second bore, bore 576, extends forward from bore 574. Bore 576, unlike bore 574 is further dimensioned to receive sleeve 590. Not identified is the step between bores 574 and 576 that forms the base of bore 576. Bore 576 is oval in shape and is centered on longitudinal axis of the hub body 570. While the major and minor axes through bore 576 are slightly greater than, respectively the cross sectional height and width of the body of dilator 588. A notch 578 extends inwardly from one side of hub body 570. The notch 578 extends into and is contiguous with bore 574. The distal end of notch 578 is spaced slightly proximally from the step between bores 574 and 576. Notch 578 is formed to have an undercut, (not identified) that extends proximally such that the undercut is located within the shell body 572. This undercut is contiguous with the proximal portion of bore 574. A number of closed end bores 577 extend rearward inward from the proximally directed face of sleeve hub body 572. Bores 577 are present for manufacturing reasons only.

Sleeve hub 570 is further formed to have a foot 578 that extends proximally rearward from the proximal face of the hub. Foot 578 is located inwardly from the outer perimeter of the hub 570. The sleeve hub 570 is shaped so that, when the hub 570 abuts the dilator hub 552, foot 578 extends into the open end of the dilator hub bore 564. The seating of foot 578 in bore 564 inhibits the relative rotation of the dilator and sleeve hubs 552 and 570, respectively. The sleeve hub 570 is further formed to have a groove 580, shown only in cross section in FIG. 48. When dilator hub 552 and sleeve hub 570 are fitted together, dilator hub bore groove 565 and sleeve hub groove 580 are located on the same side of the introducer 550.

A steering tab 581 is moveably mounted to the sleeve hub 570. Steering tab 581 is seated in hub notch 576. The steering tab 581 has a finger like bar 582 that is disposed in the undercut of notch 576. A tab 582 extends outwardly from bar 581 out of hub notch 576. The tab has a base, not identified, that rests on the inner wall of hub body 572 that define the distal end of notch 576.

A lock plate 583 is removably mounted to both dilator hub 552 and sleeve hub 570. In one version of the invention, the lock plate 583 is provided with pins (not identified). One lock plate pin seats in dilator hub groove 565, the second pin seats in sleeve hub groove 580.

Sleeve 590, like dilator 596 is oval in cross sectional shape. The sleeve is formed from stainless steel braid reinforced polyether block amide such one sold under the trademark Pebax by Arkema of Colombes, France and has a wall thickness of approximately 0.25 mm. Not illustrated are the braids internal to sleeve 590. Wires 591 extend longitudinally through the sleeve 590. The lumen that extends through the sleeve (lumen not identified) is dimensioned to slidably receive the sheath encased electrode array 30. The proximal end of the sleeve 586 is adhesively secured to the inner wall of the sleeve hub 570 that defines bore 576. The distal end of the sleeve 590 abuts the step between bores 574 and 576. In the illustrated version of the invention, a reinforcing collar 593 is seated in hub bore 576. Collar 593 extends over the proximal section of sleeve 590 adjacent sleeve hub 570. When the introducer 550 is assembled, sleeve 590 extends over dilator 590. The sleeve 590 does not extend over the whole of the dilator 590. The sleeve 590 is dimensioned so that the sleeve distal end is located slightly proximal to where the dilator tip 598 tapers inwardly from the rest of the dilator body. The most distal end section of sleeve 590 has a taper, illustrated but not identified in FIG. 44, that extends over the underlying tapered portion of the dilator tip 598.

One or two of the wire strands 591 are connected steering tab 581 (connection not shown). The displacement of the steering tab 581 results in the like displacement of the attached wire strands 591. The displacement of the wire strands 591 results in the flexure of the sleeve 590.

VI. Operation

One step in implanting an electrical array 30 using system 50 of this invention is the initial determination of the general location of the target tissue over which the array is to be deployed. This step is performed using diagnostic techniques and equipment that are not part of this invention.

Figure 49:
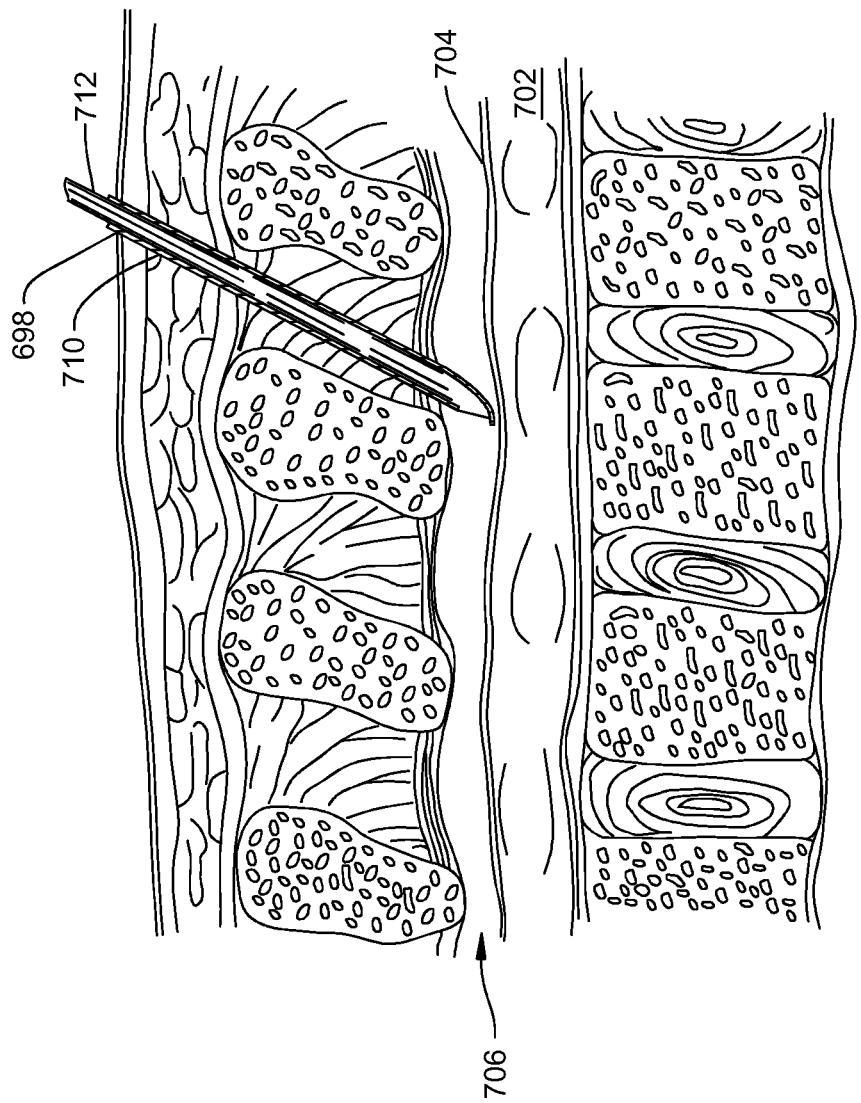
FIG. 49 is a cross sectional view illustrating how a portal is initially formed in tissue in order to insert and deploy an electrode array according to this invention.

After the general location of the target tissue is identified, a portal is formed in the body adjacent the target tissue. FIG. 49 illustrates how a portal 698 is formed when the array 30 is to be deployed over the spinal cord 702. When the array 30 is employed to flow current through the neurological tissue forming the spinal cord, the array is disposed over the dura 704 in the epidural space 706. The dura 704 is the protective tissue that surrounds the CSF, the arachnoid, the subarachnoid space and the nerves forming the spinal cord. The epidural space is the potential space within the spinal column between the dura 704 and the ligamentum flavum, the tissue that connects the individual vertebrae together that forms the spine. This process starts with the insertion of an epidural needle 710 between two vertebrae. A stylet 712 is typically seated in the needle 710 during this process. The puncture formed by the epidural needle 710 defines the portal 698 in the patient through which the other components of system 50 are inserted into the patient. It will be noted from the Figures that the distal end of the epidural needle is curved. The opening out of the needle is on the side of the needle 710. During this process, the epidural needle 710 is inserted into the patient so that the open end of the needle is directed towards the target tissue.

Once the portal is initially formed, stylet 712 is removed from the needle. (step not illustrated).

Figure 50:
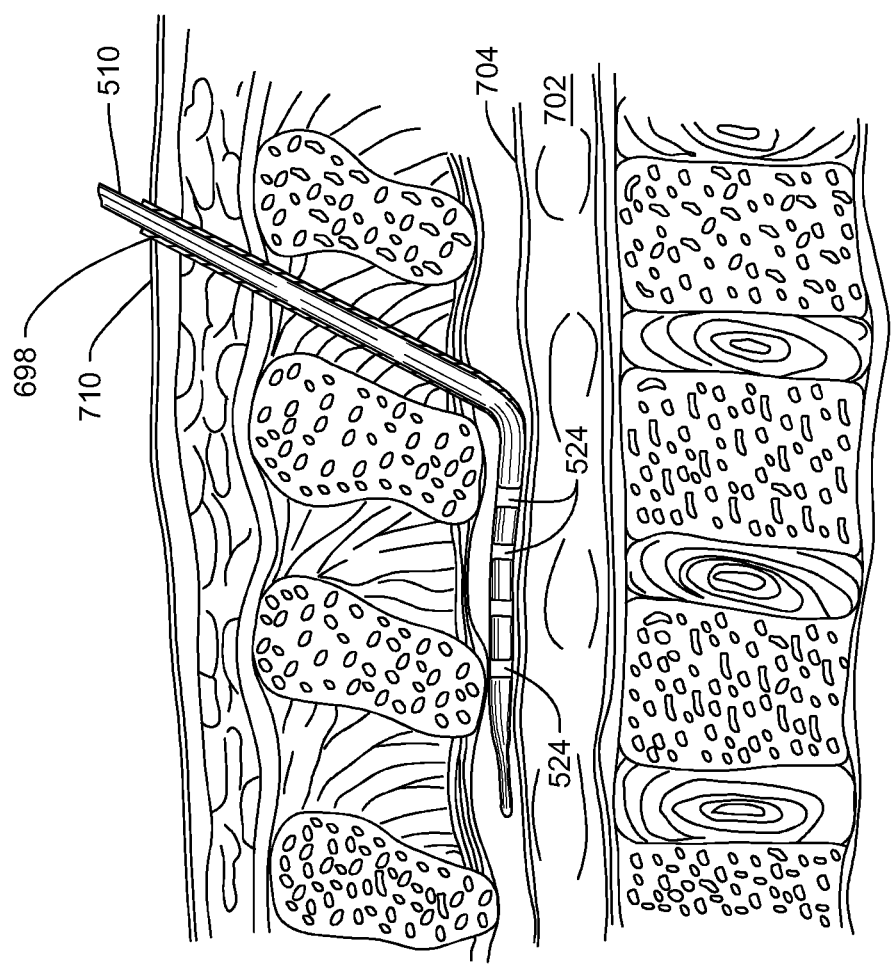
FIG. 50 is a cross sectional view depicting the insertion of the guidewire of this invention.

The guidewire 510 is then fed through the cannula of needle 710 as seen in FIG. 50. Owing to the curvature at the distal end of the needle 710 it is observed that as the guidewire 510 exits the needle, the guidewire curves away from the dura 704. As the guidewire 510 continues to be discharged from the epidural needle 710, the guidewire travels over the dura 704. A fluoroscope may be used to track the position of the guidewire 510.

During the procedure, straight and curved stylets may be sequentially fitted in the guidewire 510. This facilitates the steering of the guidewire towards the vicinity region in which it is believed the implantable medical device, array 30, should be deployed.

When the guidewire conductive sleeves 524 are in the vicinity of the target tissue, the advancement of the guidewire is terminated. The guidewire conductors 526 are connected to the external test module. This step may be performed before the guidewire 510 is inserted in the epidural space. Currents are sourced from/sunk to the sleeves 524 to cause flows through various sections of the target tissue. The response of the patient to these current flows is monitored. This testing is performed to determine if the current flow through the target tissue shows some indications of the intended beneficial effects of the flow the array 30 will provide and/or does not cause intolerable side effects.

As a result of this process there may be some readjustment of the position of the guidewire 510 to find the location where the current flow results in the optimal combination of beneficial therapy and tolerable side effects. A fluoroscope or other device may be used to mark the location over the spinal cord 702 over which the guidewire sleeves 524 (electrodes) are positioned when this further defined target tissue is identified.

The epidural needle 710 is then removed from the patient. (Step not illustrated). To perform this sub-procedure, it is often necessary to first disconnect the test module from the guidewire conductors 524. At the conclusion of this process, the guidewire 510 remains in the patient. More specifically, the proximal end of the guidewire 510 extends out of the portal 698.

Figure 51:
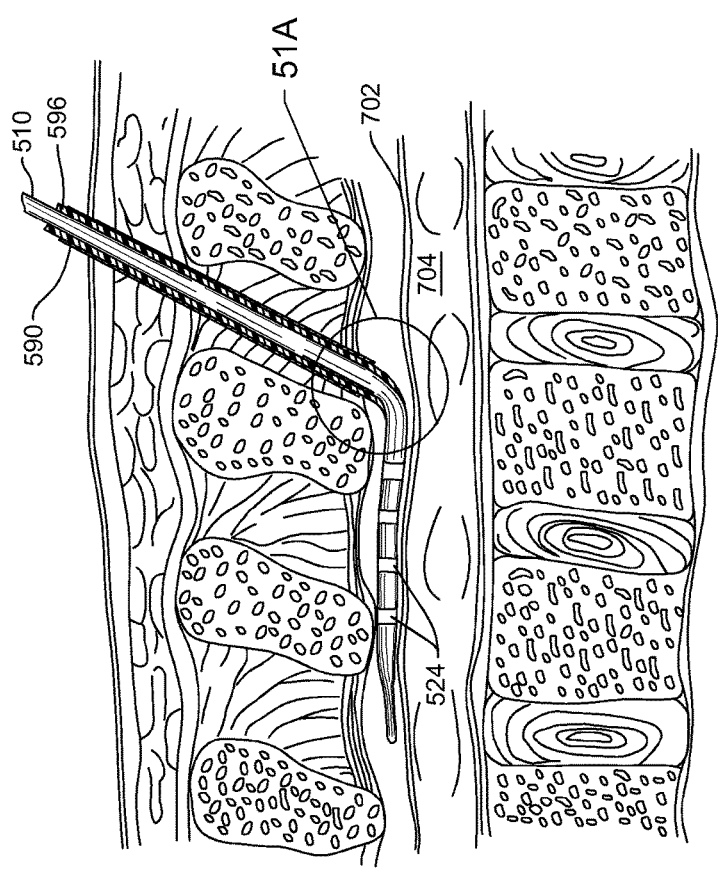
FIG. 51 depicts the positioning of the of the inserter over the guidewire.

Introducer 550 is then inserted in the patient. In this process, dilator 596 is slid over the guidewire 510. The dilator 596 is threaded over the guidewire 510 so that the guidewire extends through dilator bore 602. The guidewire 510 extends proximally out of dilator hub bore 558. The practitioner then grasps and pushes forward on hubs 552 and 570 to advance the sleeve 590 and the dilator 596 through the portal 60 subcutaneous tissue as seen in FIG. 51. (In FIG. 51 and FIG. 53 for ease of illustration the proximal end of the hubs of the introducer 550 are not shown.) The cross sectional area of the dilator 596 is greater than the guidewire 510. Accordingly as the sleeve 590 and dilator 596 advance through the tissue, the dilator 596 expands the size the portal into the patient. In the presently described procedure, the sleeve and dilator are feed over the guidewire to at least the point where the guidewire curves and starts to extend linearly over the dura 704.

Figure 51A:
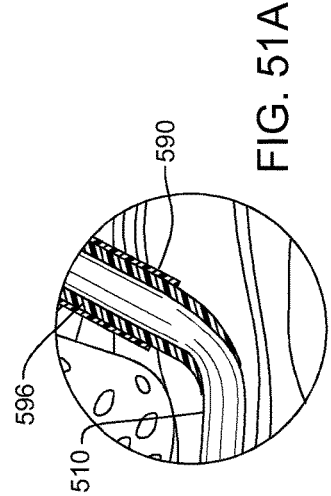
FIG. 51A is an enlarged portion of FIG. 51 depicting the distal end of the inserter over the guidewire.

Sleeve 590 and dilator 596 tend to be less flexible than guidewire 510. This stiffness of the sleeve 590 and dilator 596 are what enable the sleeve and dilator to expand the muscle, the inter vertebral ligaments and the ligamentum flavum through which they are inserted. This stiffness reduces the ability of the sleeve 590 and dilator 596 to turn when emerging from between the vertebral bodies into the epidural space. Accordingly, in the portion of the process in which the sleeve 590 and dilator 596 are so advanced, tab 581 is manipulated to place a tension of sleeve strand 591. This tension flexes the sleeve 590 and encased dilator 596. The flexing of the sleeve 590 and dilator 596 causes them, when further advanced to advance the guidewire 510, to turn towards the target tissue, as seen in FIGS. 51 and 51A.

Once the sleeve 590 and dilator 596 are positioned, the guidewire 510 and dilator 596 are withdrawn (steps not illustrated). Initially, the guidewire 510 is pulled out of the dilator bore 602 and the dilator and sleeve hubs 552 and 570, respectively. Dilator 596 is then withdrawn from sleeve 590. This process starts with uncoupling of the lock plate 582. At a minimum, the lock plate 582 is decoupled from at least one of the dilator hub 552 or the sleeve hub 570. In some procedures, the lock plate 582 is decoupled from both hubs 552 and 570. The practitioner then pulls proximally on the dilator hub 552 so as to extract the dilator 596 from sleeve 590. In some procedures, the practitioner holds sleeve hub 570 to prevent proximal displacement of the sleeve 590. At this time, the sleeve 590 remains in the portal and is ready to accept the sheath-encased electrode array 30.

Figure 52:
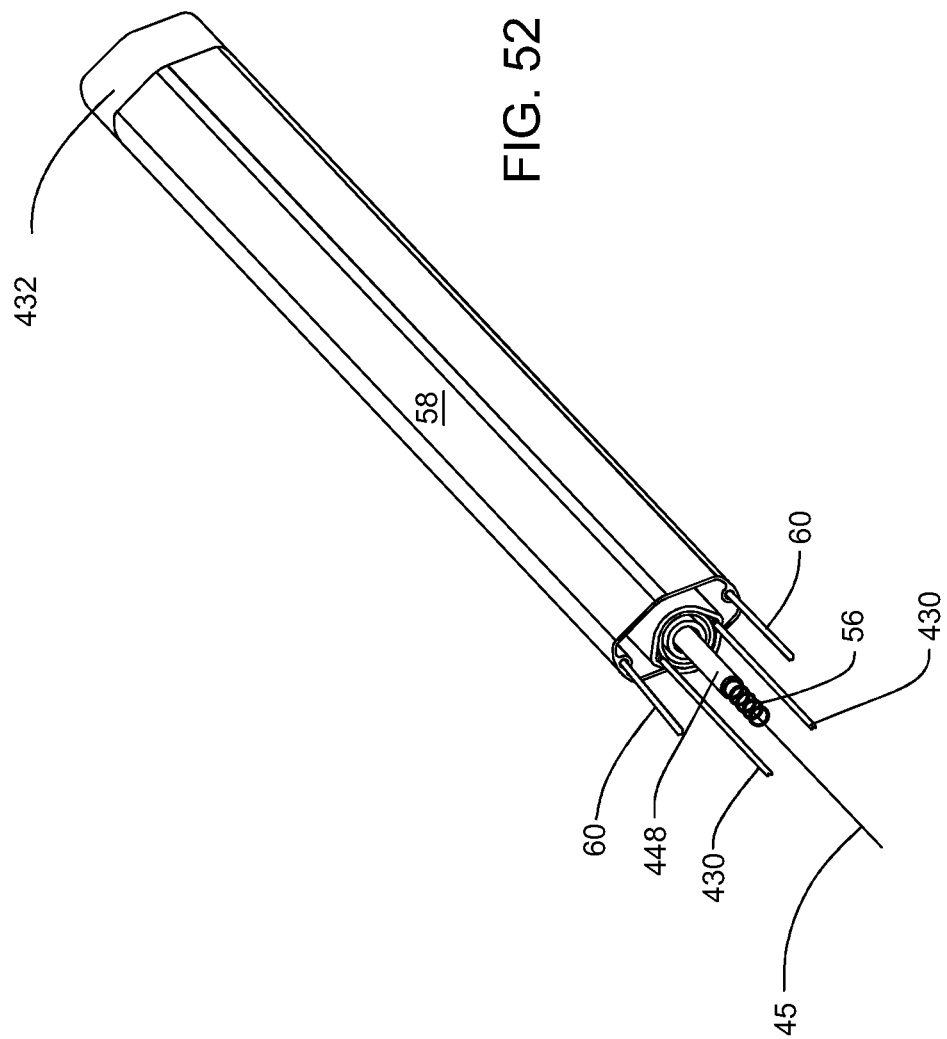
FIG. 52 is a perspective view depicting the components contained in the sheath proximal to the folded over electrode array.
Figure 53:
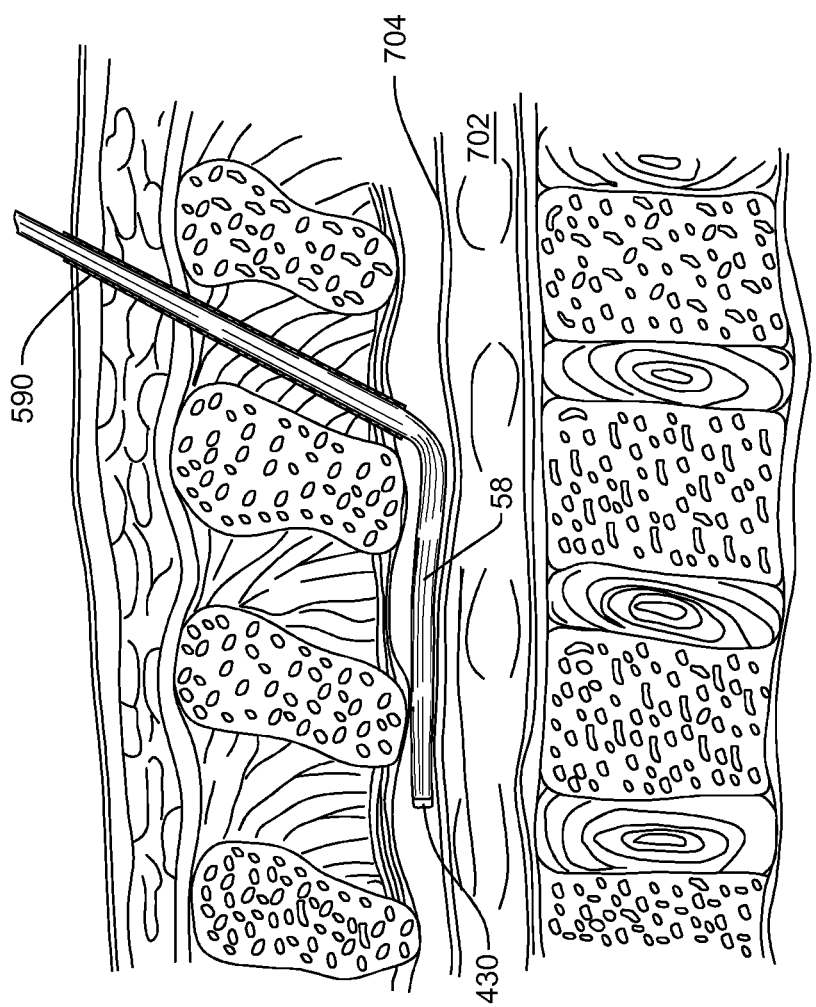
FIG. 53 depicts the insertion of the sheath encased electrode array according to this invention.

The actual insertion of the array 30 into the patient begins with the threading of the sheath encased array into first the sleeve hub 570 and then sleeve 590. For ease of illustration, the sleeve 590 is shown in FIG. 53 having a greater thickness than as depicted in FIG. 51. At this time, as seen in FIG. 52, it should be appreciated that extending proximal back into the handpiece 52 are: cable 45 containing the wires that extend to the array 30; spring 56; steering cables 60; and the proximal portions of core forming wires 430. Spring 56, it will be recalled, is attached to tube 335 integral with the proximal slide 64. The array cable 45 extends out the distal end of the tube 335 and out of the proximal end of handpiece 54 through tail bore 110. Often, prior to the insertion of the sheath encased array 30 in the portal 698, set screw 115 is set to clamp the section of cable 45 disposed in handpiece tail 110.

Once the proximal end of the sheath 58, the end in which the array 30 is disposed, is disposed in the sleeve 590, the practitioner with one hand, holds handpiece 52 and, with the other hand, the section of the sheath 56 immediately adjacent the introducer sleeve hub 570. The pushing forward of the handpiece 52 results in a like forward displacement of the array 30 and sheath 58. Spring 56 resists some axial loading. Accordingly, the spring 56 as well as the electrode array 30 disposed in front of the spring are axially advanced with the sheath 58.

As a result of the prior removal of dilator 596 from sleeve 590, some of the tissue surrounding the sleeve may have compressed the sleeve inwardly. The braids internal to sleeve 590 resist at least some of the compression of the sleeve. Accordingly, the lumen internal to sleeve 590 has a cross sectional area that if not equal to that of sheath 58 is not appreciably smaller than that of the sheath. Further the tissue surrounding the sleeve 590, having previously expanded away once from the portal, has a compliancy that was not previously present. This compliancy reduces the force needed to, when threading sheath 58 through the sleeve 590, expand the tissue outwardly in order to advance the sheath. Thus, during the initial part of the array insertion process, large amounts of manual force are not required in order to introduce the array 30 into the patient.

During this process of advancing array 30 towards the target tissue, handpiece ratchet 68 is seated in handpiece slot section 86. Release button 408 is set so the button head 412 seats in ratchet opening 386. The engagement of the release button 408 with the ratchet 68 holds the ratchet in the retracted state in which it is partially disposed within the handpiece 52. Also at this time, the distal slide 62 is in its forwardmost position. Release button toe 422 is seated in distalmost handpiece notch 96. Owing to the positioning of the distal slide 62, each steering block 172 is disposed under a separate one of the steering button bosses 290. More particularly, each steering button boss 290 is disposed immediately above a separate one of the steering boss steps 268. The slide spring loaded ball 234 is seated between two of the ridges 149 in lip rib 146. This engagement of the ball 234 with ribs 146 holds the distal slide 62 in its distalmost position. Cam lock 340 is disposed between lid ribs 142 and 146. The cam lock 340 thus holds the proximal slide in a fixed position forward of handpiece proximal panel 82.

As the sheath encased electrode array exits the sleeve 590, the array moves along the dura 704. During this and other movement of the array, the array may encounter tissue that resists this motion. Spring 56 prevents the axial buckling of the array and sheath 58 that can occur in response to this resistance. The position of the sheath 58, more particularly the distal end in which the array 30 is encased, may be tracked with a fluoroscope.

As the sheath 58 is advanced to over the target tissue, it may be necessary to steer the sheath. The practitioner performs this act by pressing downwardly on the appropriate one of the wings 288 of button 282. The practitioner performs this action with the thumb or finger of the hand holding handpiece 52. This displacement of the button 282 results in the boss 290 integral with the depressed wing 288 pressing against the step 268 of the adjacent steering block 172. The steering block 172 is therefore displaced downwardly relative to the distal slide 62. The downward displacement of the steering block 172 results in a like displacement of the section of the steering cable 60 threaded to the block. It will be recalled that, owing to the adjustment of nut 265, the steering cable 60 already is in tension. Consequently, the displacement of steering cable 60 by the steering block causes the distal end of the cable to move towards the handpiece 52. It is recalled that the distal end of the steering cable 60 is anchored in the distal end of the sheath bore 470 in which the cable is seated. The retraction of the distal end of the steering cable 60 causes the side of sheath 58 through which the cable extends to flex towards the handpiece 52. The sleeve 476 through which the cable 60 extends limits the extent to which the retracting cable is able to flex the sheath. Specifically, the sheath flexure primarily occurs where the sleeve 476 is not present; the distal end of the sheath 58, the section of the sheath in which the array 30 is encased. This flexure of the sheath thus allows the sheath to, as it is advanced towards the target position, be steered around obstructions that inhibit linear advancement of the sheath.

As a consequence of the depression of steering button 282, steering cable 60 may be subjected to a significant amount of force. This can occur for example, if the tissue adjacent the distal end of the sleeve 58 opposes the flexure, the turning, of the sleeve. If the cable is subjected to more than a specific amount of force, the force on the cable will be greater than the force spring 270 imposes on sleeve 258. Should this event occur, instead of the cable 60 continuing to pull its distal end rearwardly, the cable, through anchor 264 and nut 265, pulls the tensioner 258 distally, towards the front end of handpiece 52. This feature of the invention reduces the likelihood that so much force will be placed on the steering cable distal to the handpiece that the cable will either separate or damage other components of the insertion system 50 of this invention. In some versions of the invention, each tensioner assembly 168 is designed so that the spring 270 will begin to compress when the cable 60 through connected components places 5 pounds (22.25 Newtons) force on the spring.

Eventually, the distal end of the sheath 58 is disposed over the target tissue, the tissue against which the electrode array 30 is to be deployed. Once the practitioner is in this stage of the procedure, it is necessary to both deploy the electrode array 30 and retract the core 54 and sheath 58 away from the array and out of the patient. This process begins by the release of ratchet 68 from the retracted state. This step is performed by the manual displacement of release button 408 proximally. Specifically, button 408 is retracted so that button toe 422 seats in the more proximal two of the notches 96 internal to the handpiece base 72. The retraction of button 408 allows the release of the potential energy stored in spring 402. The spring 402 pushes pawl 390 upwardly so as to result in the opposed downward pivoting movement of ratchet 68.

The practitioner then, with the fingers of the hand holding handpiece 52, repeatedly pulls upwardly on the ratchet 68. This manual force overcomes the force spring 408 outputs in holding the ratchet 68 in the extended state. This displacement of ratchet 68 causes the free end of the pawl 390, the end associated with face 392, to engage against one of the teeth of distal slide rack 212. The motion of the pawl 390 against the rack 212 pushes the distal slide 62 rearwardly, towards handpiece proximal panel 82. This manual force the practitioner exerts against through the ratchet 68 and pawl 390 on the distal slide 62 is enough to overcome the force of the spring that holds ball detent 234 against the handpiece rib 146. Therefore the distal slide 62 is displaced rearwardly, towards the handpiece proximal panel 82. The proximal movement of the distal slide 62 results in a like movement of the attached sheath 56. The rearward movement of distal slide 62 displaces the steering blocks 172 so the blocks are out of registration with bosses 290 integral with button 282. Once the steering blocks 172 are so displaced, the displacement of the button 282 therefore will not force the like movement of the steering blocks 172 and resultant tensioning/slackening of the steering cables 60.

During this initial rearward displacement of the distal slide 62, the distal slide 62 is spaced from the proximal slide 64. As the distal slide 62 continues to move rearward, the distal slide 62 moves under the proximal slide 64 so as to not have any contact with the slide or any components attached to the slide 64. Consequently, the rearward movement of the distal slide 62 has no effect on the proximal slide 64.

During this stage of the sheath and core retraction sub-steps, cam latch 340 is seated between lid rib faces 144 and 148. Leaf spring 358 prevents rotation of the cam latch 340 away from ribs 142 and 146. Spring 358 prevents the movement of the cam latch 340 and the cam latch prevents movement of the proximal slide 64. Core 54 is connected to the proximal slide 64. Given that, during this phase of the sleeve retraction step, the proximal slide 64 is in a static position within the handpiece 52, a fixed length section of core 54 remains extended out from the handpiece 52.

After each phase of a ratchet pivoting cycle in which the ratchet 68 is manually displaced towards the handpiece 52, the practitioner releases the grasp on the ratchet. Spring 402 returns the ratchet 68 to the extended state.

Figure 54:
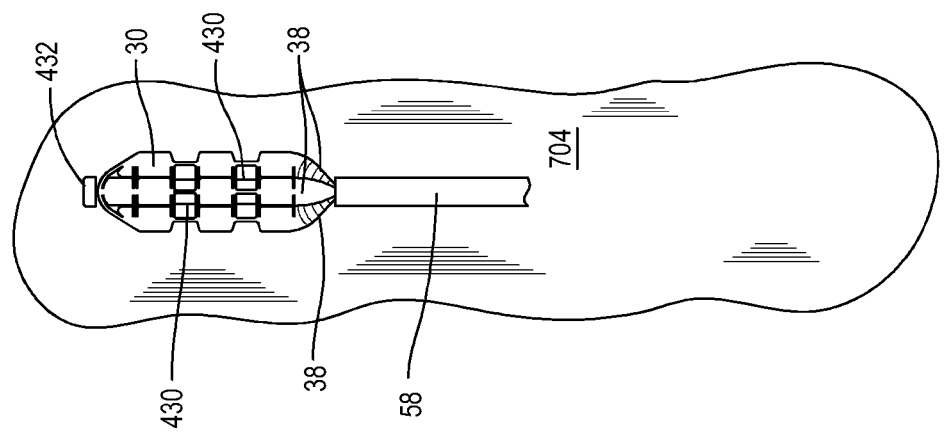
FIG. 54 depicts the partial retraction of the sheath away from the electrode array and the partial deployment of the array.

As a result of this rearward displacement of the sheath 58, the sheath moves proximally away from the distal end of the core 54, the end over which the electrode array 30 is folded. The movement of the sheath 58 away from the folded over array 30 allows the potential energy stored in the folded over/bent away frame 32 to be released. This energy unfolds/unbends the array 30 so that the sections of the array folded over/under the core 54 unfold/unbend away from the core as seen in FIG. 54. When the electrode array 30 is so unfolded/unbent, the array is considered in the deployed state. When the array 30 is in the deployed state, the electrodes 34 face the target tissue, the tissue through which current is to be flowed.

Figure 55:
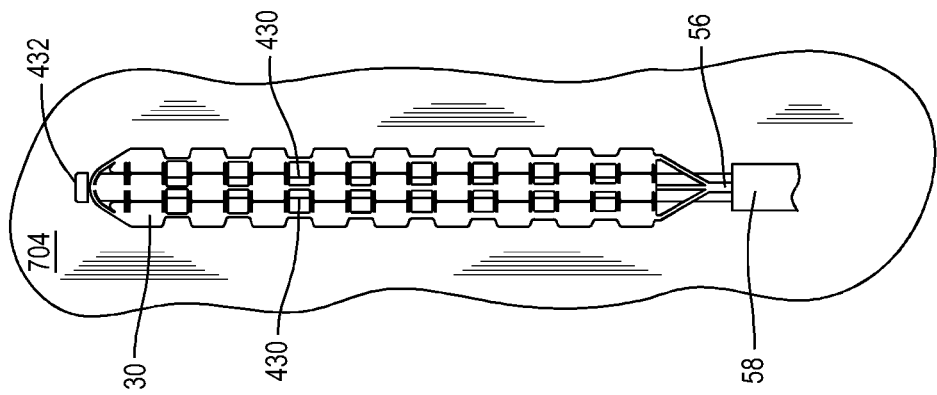
FIG. 55 depicts the electrode array upon the full retraction of the sheath.

As seen by FIG. 55, immediately after the full retraction of sheath 58 away from the electrode array, the core 54 remains disposed between the array and the target tissue. Core 54 is retracted away from the array 30 by the continued pivoting of ratchet 68. As a consequence of the resultant further displacement of the distal slide 62, the proximal facing edge of plate 170 abuts cam latch tabs 350. Since spring 358 inhibits the rotation of the cam latch 340, tabs 350 likewise resist displacement. This resistive force the spring 358 places on the cam latch 340 causes the latch to initially resist the further rearward displacement of the distal slide 62. The tactile feedback the practitioner feels in overcoming this resistance provides an indication that any additional pivoting of ratchet 68 will result in the retraction of core 54.

To actually retract the core 54, the practitioner initially applies a slightly stronger manual force of the ratchet 68 to cause the continued displacement of the distal slide 62 than was required to simply retract the sheath 58. As a result of this displacement of the distal slide, the proximal end of the attached plate 170 is moved against the cam latch tabs 350 with sufficient force to overcome the force spring 358 places on the cam latch 340 to hold the latch in position. The cam latch tabs 350 are rotated upwardly. More particularly, each tab rotates into one of the slots 135 formed in handpiece lid 74. This causes a corresponding downward rotation of the cam beam 342 away from the space between lid ribs 142 and 146. As a result of this displacement of cam latch 340, distal slide 62 is able to move underneath proximal slide 64.

Figure 56:
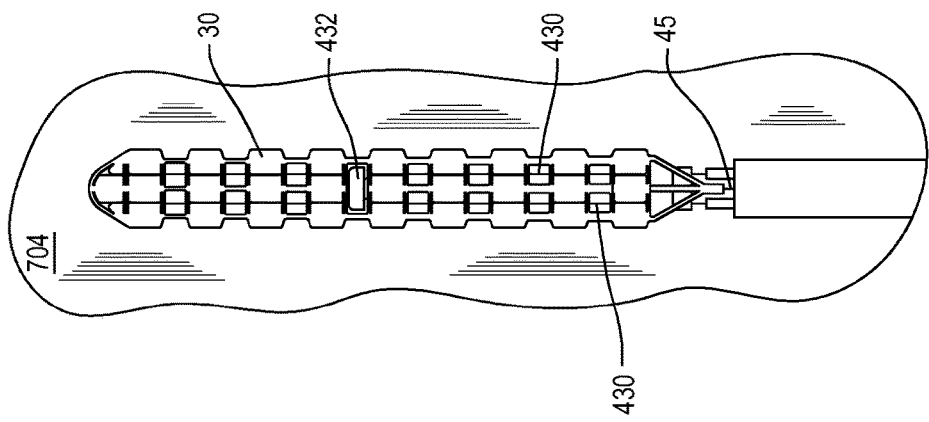
FIG. 56 depicts the partial retraction of the core from underneath the electrode array.

As a result of the movement of the distal slide 62 underneath the proximal slide 64, the proximal end of the distal top panel 170 abuts, engages, proximal slide shoe 330. When the ratchet 68 is actuated to force the distal slide 62 further rearwardly, distal slide 62 now pushes proximal slide 64 in the same direction. The proximal slide 64 moves over handpiece ribs 106. The wire sections 430 forming core 54 are attached to the proximal slide 64. This during the simultaneous rearward displacement of slides 62 and 64 in handpiece 52, both the core 54 and the sheath 58 are retracted rearwardly away from the proximal end of the deployed electrode array 30. As seen in FIG. 56, the core 54 is retracted away from its position between the electrode array 30 and the target tissue. In FIG. 56, a section of the center-located frame bridge 38 is removed to show the presence of the core head 432 below the deployed electrode array 30.

During the process of retracting the proximal slide 64 it should be understood that both spring 58 and tube 335 are simultaneously retracted. The electrode array cable 45 extends through both spring 56 and tube 335. The clamping of the cable 45 by set screw 115 in the handpiece tail 110 inhibits the rearward movement of the cable. The blocking of cable 45 from rearward movement inhibits similar rearward movement of the array 30 away from over the target tissue. Since cable 45 is disposed within spring 56, the spring prevents the cable from buckling.

Figure 57:
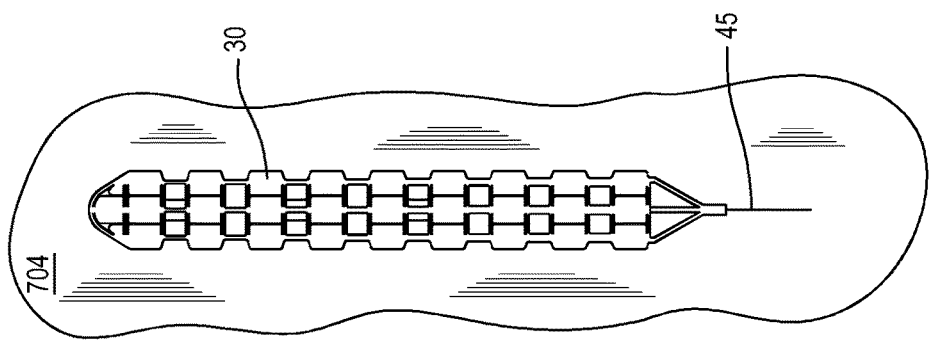
FIG. 57 depicts the deployment of the electrode array over the target tissue upon the complete retraction of the core.

Slides 62 and 64 are simultaneously retracted in the same direction, towards the handpiece proximal panel 78. Eventually the proximal slide pin detent 360 moves into registration with bore 140 internal to handpiece lid 74. The pin integral with detent 360 moves into lid bore 145. The seating of the pin in bore 140 blocks further movement of the proximal slide 64 and, by extension distal slide 62. The perception of the absence of this resistance when the ratchet is further pressed to retract the slides 62 and 64 functions as tactile feedback to the practitioner that the core 54 and sheath 58 have been retracted as far away as possible from the electrode array 30 with the handpiece. FIG. 57 represents the array 30 disposed over the target tissue, dura 704, once the core is fully retracted away from the array.

The process of retracting the core 54 and sheath 58 completely out of the patient then proceeds with the loosening of screw 115 in the handpiece tail 110. This allows the handpiece 52 and attached components to be passed over cable 45. The handpiece is then so moved away from the patient while the cable is held stationary relative to the target tissue. This retraction of the handpiece away from the patient results in a like withdrawal of the core 54 and sheath 58 from out of portal 698.

Once the handpiece 52, core 54 and sheath 58 are completely removed from the patient, sleeve 590 is removed from the patient by the practitioner pulling the sleeve hub 570 away from the patient. It should be appreciated that in this process, the sleeve hub 570 and sleeve 590 are passed over the whole of the portion of cable 45 that extends out of the patient.

Once hub 570 and sleeve 586 are removed, cable 45 is trimmed to length. Cable 45 is then tunnel connected to the IDC 46. This assumes the IDC 46 is already implanted in the patient. Current can then be flowed through the electrodes in order to obtain the desired therapeutic effect System 50 of this invention thus functions as an assembly useful for initially providing an indication if the current flowed through the target tissue will offer a benefit to the patient and/or ensuring that the side effects are tolerable. The system 50 then provides a means to define an initial portal 698 into the patient that is directed towards the target tissue. Once the system provides the portal, the handpiece 52 of system 50 is used to both advance the electrode array 30 towards the target tissue and steer the array towards the tissue. Handpiece 52 is designed so that the practitioner can with a single hand both hold the handpiece to advance the electrode array, and with the thumb or a finger of that hand depress button 282 that steers the array. Once the electrode array is over the target tissue, again using the hand holding handpiece 52, the practitioner depresses ratchet 68. The depression of the ratchet 68 results first in the retraction of the sheath 58 from around the array 30 and then the retraction of the core 54 from underneath the array.

Thus, system 50 of this invention provides a convenient means for both accurately percutaneously positioning an electrode array 30 over target tissue and, once the array is so positioned, deploying the array. As part of the deployment process, the components of the system used to position the array are retracted out of the patient without appreciably disturbing the deployed array.

VII. Alternative Embodiments

The above is directed to one specific version of this invention as well as one specific method of use. Alternative versions of this invention may have alternative structures and uses in alternative surgical procedures.

For example, there is no requirement that all versions of this invention be used with the described electrode array 30.

Other versions of this invention may be used with electrode arrays that have features different from what has been described. Thus, it may be desirable to use this invention in order to position an electrode array that, once positioned over the target tissue does not unfold or unbend. In these versions of the invention, the electrode array may simply rest on the core. The invention may be used to insert and deploy medical devices that offer therapeutic benefits or diagnostic information other than electrode arrays and stents.

Likewise, there is no requirement that all versions of the invention include both a core and a sheath for positioning the electrode array over the target tissue. In some versions of the invention, it may not be necessary to provide a core for supporting the electrode array. In these versions of the invention the electrode array is simply encapsulated inside the sheath. Using a modified handpiece of this invention, the sheath and electrode are steered to the target tissue. Once the electrode is over the target tissue, the single slide internal to the handpiece, the slide to which the sheath is attached, is retracted. This retraction of the sheath exposes the electrode array to the target tissue.

Still other versions of the invention may not include a sheath that is disposed over the implantable medical device. In these versions of the invention, the core functions as a support that is advanced in order to seat the overlying implantable device over the target tissue.

Alternatively, in some versions of this embodiment of the invention, the wires forming the core may be the wires that are steered. In these versions of the invention, a portion of the core proximal to the array may be encased in a sleeve or sleeves that inhibit flexure of the core-forming wires. In this version of the invention, when a steering tension is imposed of one of the core wires, only the distal end of the wire is flexed, steered.

Likewise there is no requirement that all versions of this invention include an assembly for steering the electrode array.

In some versions of the invention, the core 54 that serves as the carrier for the electrode array 30 may not be separate from the system components proximal to the core that advance the core to over the target tissue and then retract the core. For example, in some versions of the invention, the wire forming the core may be a distal end extension of the wire forming the spring that extends proximally from the core. Alternatively, instead of being formed from metal, the electrode carrying core and structure extending distally therefrom may be formed from other materials. Thus, in some versions of the invention, the core may be formed from a section of plastic. The system component that extends distally from the core may be plastic tube constructed to be both flexible and resist axial buckling. These two components may be formed from a common piece section of plastic or formed from two different pieces of plastic that are bonded together. Similarly, one of these components can be plastic and the other metal.

The steering unit may likewise take other forms. For example, it may be desirable to provide a steering unit either attached to the sheath or the core that has three or more steering cables. At least one of steering cable is not linearly aligned with at least two of the cables. This version of the invention would thus allow the core to be steered not just left or right but also up or down. Similarly, the tensioners of the steering units that selectively tension or slack the steering cables may be different from the above described steering blocks. In some versions of the invention, the steering unit tensioners may be a rotating pair of opposed arms. Each steering cable, assuming two such cables, is attached to the free end of a separate one of the arms. The rotating of the arms tensions/slacks the steering cable. A knob mounted to handpiece 52 is rotated to cause a like rotation of the arms. Alternatively, the steering cables may be mounted to slides that function as the steering unit tensioners. Buttons mounted to the handpiece to slide along the handpiece are displaced to tension and slack the steering cables.

If components of the steering unit are attached to the slide, in some versions of the invention, these components may be attached to the slide that retracts the core 54. Some steering units of this invention may not have components attached to either slide.

The retraction units that retract the core 54 and sheath 58 need not always each be slides. For example, one or more of these retraction units may be spindles. This type of The core or sheath is attached to the spindle. The actuator, when activated, rotates the spindle. The rotation of the spindle results in the attached core or sheath wrapping around the spindle.

An actuator other than the disclosed ratchet system may be employed to retract the core 54 and/or sheath 58. Thus one retraction system may simply be some sort of finger hold that extends from the slide, through the handpiece. The practitioner grasps and retracts the finger hold to displace the slide to which the finger hold is attached.

Versions of the invention with two retraction units may have two control members, one for each retraction unit. This arrangement allows the practitioner to independently control the actuation of each retraction unit. This would allow the practitioner to independently control the extent to which the core and sleeve are retracted away from the medical device being implanted. If this construction of the invention, both control members would be acceptable by a thumb or finger of the hand holding handpiece 52. One construction of this version of the invention, the control members are triggers. Each trigger is repetitively pulled to cause the retraction of the associated core 54 or sheath 58. Alternatively, independently displaced slide buttons function as the control members for the individual retraction units.

Depending on the device the handpiece 50 is employed to implant, the retraction units may be configured so that, when first actuated, both units are simultaneously actuated. Alternatively, the retraction unit may be configured to first retract the core and then retract the sheath.

Devices other than a set screw may releasably hold the cable 50 to handpiece 52. For example, in one version of the invention a camming device may hold the cable 50 in place. In these versions of the invention, the camming device may normally hold the cable to the handpiece 52. The rearward movement of the proximal slide 64 may move the cam from the locked state to the unlocked state. This transitioning of the cam unlocks the grip the cam imposes on the cable. A benefit of this version of the invention is that it eliminates the need for the practitioner to have to adjust a screw or similar locking component when it is time to withdraw the cable.

The other components of system 50 of this invention may also be different. For example, the guidewire of this invention may be provided with one or more steering cables. This would allow the guidewire to be selectively steered past obstructions between where the guidewire is introduced and the target tissue. Likewise, in some versions of the invention, the dilator and insertion sleeve may have sufficient length so as to extend over the whole of the guidewire. Using the components of this version of the invention, once the guidewire is properly positioned, the inserter is then moved distally forward to extend over substantially all of the guidewire. The inserter thus extends over the target tissue. The guidewire and dilator are then removed. The sheath and/or core are then advanced through the inserter sleeve to the section of the sleeve over or adjacent to the target tissue. The introducer sleeve is then removed from the patient. This type of introducer system could be useful for inserting paddle type arrays. These versions are the invention are useful when it is desired to provide a path that is unobstructed as possible from the portal through which the electrode array is introduced to the location over the target tissue where the electrode array is to be deployed.

Also, while the components of this invention are designed to facilitate the percutaneously insertion of electrode arrays, the components of this invention may find utility in procedures in which large incisions are made in order to implant and deploy an electrode array.

The stated dimensions, unless recited in the claims, are for purposes of example only.

Therefore it is an object of the appended claims to cover all such modifications and variations that come within the true spirit and scope of this invention.

What is claimed is:

1. An assembly for percutaneously inserting an implantable medical device, said assembly including:
   a handpiece including a housing shaped to be held in a single hand;
   a sheath formed from material that can be placed in a living being, said sheath having a distal portion in which the implantable medical device can be disposed so the implantable medical device and the sheath distal portion can be disposed in a living being and a proximal portion that extends rearwardly from the distal portion to said handpiece housing;
   a first slide moveably disposed in said handpiece housing to move between a first position and a second position in said handpiece housing wherein, the proximal portion of said sheath is attached to said first slide so that movement of said first slide results in a like movement of said sheath;
   a steering unit, said steering unit including: at least one cable that extends to said sheath; at least one steering tensioner moveably mounted to said first slide wherein said at least one cable is connected to said steering tensioner so that movement of said steering tensioner results in selective tensioning/slackening of said at least one cable that causes said at least one cable to steer said sheath; and a control member moveably mounted to said handpiece housing, wherein said control member is positioned so that: when said first slide is in the first position in said handpiece housing, movement of said control member results in said control member engaging and moving said at least one steering tensioner so that said at least one steering tensioner tensions/slackens said at least one steering cable; and wherein, when said slide is in the second position, said steering tensioner is out of registration with said control member; and
   a displacement member attached to said first slide that is manually actuatable for moving said first slide from the first position towards the second position so that the movement of said first slide moves said at least one steering tensioner out of registration with said control member.

2. The assembly of claim 1, wherein said steering unit includes: plural said cables that extend from said first slide to said sheath; and plural said steering tensioners that are mounted to said first slide to which said cables are attached, wherein each said steering tensioner tensions/slackens a separate one of said steering cables.

3. The assembly of claim 1, wherein said steering unit includes: plural said cables that extend from said first slide to said sheath; plural said steering tensioners that are mounted to said first slide to which said cables are connected, wherein each said steering tensioner tensions/slackens a separate one of said steering cables; and a single said control member that is mounted to said handpiece housing is configured to engage and move each said steering tensioner.

4. The assembly of claim 1, wherein said displacement member is a ratchet that is moveably mounted to said handpiece housing that is connected to said first slide to, upon the movement of said ratchet, move said first slide from the first position towards the second position.

5. The assembly of claim 1, wherein:
   said first slide is formed with at least one opening:
   said at least one steering tensioner is a block that is moveably mounted in the at least one opening of said first slide.

6. The assembly of claim 1, wherein said control member of said steering unit is pivotally mounted to said handpiece housing.

7. The assembly of claim 1, wherein said at least one cable extends from a cable tensioner that is mounted to said first slide, wherein said cable tensioner is separate from said at least one steering tensioner and is configured to, independent of tension said steering tensioner places of said at least one cable, place a tension of said at least one cable.

8. The assembly of claim 1,
   wherein: at least one cable tensioner separate from said at least one steering tensioner is moveably mounted to said first slide;
   said at least one cable has a proximal end that is attached to said at least one cable tensioner so that said at least one cable extends distally forward from said cable tensioner; and
   said cable tensioner is configured to: place a tension on said at least one cable independent of tension said steering tensioner places on said cable and to, upon the application of a specific amount of force placed on said at least one cable, move relative to said first slide so as to cause a like movement of the proximal end of said at least one cable.

9. The assembly of claim 1, wherein within said handpiece housing, the second position of said first slide is located proximal to the first position of said first slide.

10. The assembly of claim 1, further including a core separate from said sheath that extends forward from said handpiece housing through said sheath, said core configured to support the medical device when the medical device is in said sheath.

11. The assembly of claim 1, further including a core separate from said sheath that extends forward from said handpiece housing through said sheath, said core configured to support the medical device when the medical device is in said sheath and, wherein, said core is moveably attached to said handpiece housing so that movement of said core relative to said housing results in retraction of said core away from said medical device.

12. The assembly of claim 1, further including a core separate from said sheath that extends forward from said handpiece housing through said sheath, said core configured to support the medical device when the medical device is in said sheath and, wherein, said core is connected to said first slide so that the movement of said first slide from the first position to the second position results in retraction of said core from the medical device.

13. The assembly of claim 1, further including:
   a core that is moveably mounted to said handpiece housing and that extends forward from said handpiece housing said sheath, said core configured to support the medical device when the medical device is in said sheath; and
   a second slide separate from said first slide is moveably disposed in said handpiece housing and wherein said core is connected to said second slide for displacement by said second slide and said first and second slides are collectively positioned so that, as the first slide moves from the first position to the second position, said first slide engages and displaces said second slide so that the movement of said first slide results in displacement of said second slide and retraction of said core from the medical device.

14. An assembly for percutaneously inserting an implantable medical device, said assembly including:
   a handpiece including a housing shaped to be held in a single hand;
   a sheath formed from material that can be placed in a living being, said sheath having a distal portion in which the implantable medical device can be disposed so the implantable medical device and the sheath distal portion can be disposed in a living being and a proximal portion that extends rearwardly from the distal portion to said handpiece housing;
   a core for supporting the implantable medical device when the device is disposed in said sheath wherein said core extends through said sheath to said handpiece housing;
   a first slide moveably disposed in said handpiece wherein, the proximal portion of said sheath is attached to said first slide so that movement of said first slide results in a like movement of said sheath;
   a second slide moveably disposed in said handpiece housing to, when engaged with said first slide, move in a same direction as said first slide in said handpiece housing wherein, said core is attached to said second slide so that movement of said second slide results in a like movement of said core and wherein said first and second slides are disposed in said handpiece housing so as to be initially spaced apart from each other and so that an initial movement of one of said first slide or said second slide causes the said slide to move towards and engage the other one of said second slide or said first slide so that continued movement of said first slide or said second slide results in subsequent simultaneous movement of both said slides in the same direction in said handpiece housing.

15. The assembly of claim 14, wherein a displacement member that is manually actuatable is attached to the one of said first slide or said second slide for, upon actuation, moving the said slide towards the other one of said second slide or said first slide.

16. The assembly of claim 15, wherein said displacement member is a ratchet that is moveably mounted to said handpiece housing and that is connected to the one of said first slide or said second slide to, upon movement of said ratchet, move the said slide to which said ratchet is connected to towards the other one of said second slide or said first slide.

17. The assembly of claim 15, wherein said displacement member is connected to said first slide.

18. The assembly of claim 15, further including a first latch that extends between the said slide to which said displacement member is connected and said handpiece housing, said first latch configured to, in the absence of a force applied by said displacement member, hold said slide to which said first latch is connected static relative to said handpiece housing.

19. The assembly of claim 14, further including a moveable second latch that extends between said handpiece housing and the one of said second slide or said first slide that is engaged by and moved by the other of said first slide or said second slide wherein, said second latch releasably holds said second slide or first slide in a static position within said handpiece housing prior to said second slide or said first slide being moved by the other of said first slide or said second slide.

20. The assembly of claim 19, wherein said second latch is moveably mounted to the said slide that said latch releasably holds static.

21. The assembly of claim 19, wherein said slides and said second latch are positioned in said handpiece housing so that, when the one of said first slide or said second slide moves towards the other of said second slide or said first slide, the said first slide or the said second slide abuts said second latch so as to move said second latch to a disengaged position in which said second latch no longer holds the said second slide or the said first slide in the static position within said handpiece housing.

22. The assembly of claim 14, wherein said slides, within said handpiece housing, are arranged so that said first slide moves towards said second slide and the continued movement of said first slide results in the subsequent simultaneous movement of both said slides.

23. The assembly of claim 14 further including:
   at least one steering cable attached to one of said sheath or said core that extends to said handpiece housing; and
   a steering unit attached to said handpiece housing that is connected to said at least one steering cable to selectively tension/slack said steering cable.

24. The assembly of claim 23, wherein said at least one steering cable is attached to said sheath.

25. The assembly of claim 14, wherein said slides are disposed in said handpiece housing so that when said slides move simultaneously in said handpiece housing, said slides move from distal positions in said handpiece housing to proximal positions in said handpiece housing.

26. The assembly of claim 14, further including a lock attached to said handpiece housing that releasably engages a cable that can extend to the implantable device so as to hold said cable static relative to said handpiece housing.

* * * * *